US011827681B2

(12) United States Patent
Skerra et al.

(10) Patent No.: US 11,827,681 B2
(45) Date of Patent: *Nov. 28, 2023

(54) MUTEINS OF HUMAN LIPOCALIN 2 (LCN2, HNGAL) WITH AFFINITY FOR A GIVEN TARGET

(71) Applicant: Pieris Pharmaceuticals GmbH, Freising (DE)

(72) Inventors: Arne Skerra, Freising (DE); Michaela Gebauer, Leipzig (DE); Dominik Hinz, Freising-Weihenstephan (DE); Sabine Rauth, Munich (DE); Gabriele Matschiner, Munich (DE); Martin Huelsmeyer, Roemerberg (DE)

(73) Assignee: PIERIS PHARMACEUTICALS GMBH

( * ) Notice: Subject to any disclaimer, the term of this patent is extended or adjusted under 35 U.S.C. 154(b) by 705 days.

This patent is subject to a terminal disclaimer.

(21) Appl. No.: 16/812,069

(22) Filed: Mar. 6, 2020

(65) Prior Publication Data

US 2020/0308237 A1   Oct. 1, 2020

Related U.S. Application Data

(63) Continuation of application No. 15/380,168, filed on Dec. 15, 2016, now Pat. No. 10,618,941, which is a continuation of application No. 13/514,133, filed as application No. PCT/EP2010/069028 on Dec. 7, 2010, now Pat. No. 9,549,968.

(60) Provisional application No. 61/267,098, filed on Dec. 7, 2009.

(51) Int. Cl.
| C07K 14/47 | (2006.01) |
| C07K 14/775 | (2006.01) |
| G01N 33/566 | (2006.01) |
| A61K 47/60 | (2017.01) |
| A61K 38/17 | (2006.01) |
| A61K 38/00 | (2006.01) |

(52) U.S. Cl.
CPC .......... *C07K 14/47* (2013.01); *A61K 38/1709* (2013.01); *A61K 47/60* (2017.08); *C07K 14/775* (2013.01); *G01N 33/566* (2013.01); *A61K 38/00* (2013.01); *C07K 2319/30* (2013.01)

(58) Field of Classification Search
CPC .... A61K 38/00; A61K 38/1709; A61K 47/60; C07K 14/47; C07K 14/775; C07K 2319/30; G01N 33/566; A61P 25/28; A61P 29/00; A61P 35/00; C12N 15/63; C12N 2795/00041
USPC ........ 435/188, 252.3, 254.2, 320.1; 530/350, 530/402
See application file for complete search history.

(56) References Cited

U.S. PATENT DOCUMENTS

| 4,376,110 A | 3/1983 | David et al. |
| 5,728,553 A | 3/1998 | Goodey et al. |
| 5,849,576 A | 12/1998 | Skerra et al. |
| 6,020,163 A | 2/2000 | Conklin |
| 6,099,517 A | 8/2000 | Daugherty |
| 6,103,493 A | 8/2000 | Skerra et al. |
| 6,123,936 A | 9/2000 | Platz et al. |
| 6,177,074 B1 | 1/2001 | Glue et al. |
| 6,403,564 B1 | 6/2002 | Ganguly et al. |
| 6,500,930 B2 | 12/2002 | Adamson |
| 6,566,073 B1 | 5/2003 | Rivera et al. |
| 6,620,413 B1 | 9/2003 | De Sauvage et al. |
| 6,696,245 B2 | 2/2004 | Winter et al. |
| 7,118,915 B2 | 10/2006 | Vogt et al. |
| 7,250,297 B1 | 7/2007 | Beste et al. |
| 7,252,998 B2 | 8/2007 | Skerra et al. |
| 7,723,476 B2 | 5/2010 | Skerra et al. |
| 8,158,753 B2 | 4/2012 | Skerra et al. |
| 8,420,051 B2 | 4/2013 | Skerra et al. |
| 8,536,307 B2 | 9/2013 | Skerra et al. |
| 9,040,020 B2 | 5/2015 | Skerra et al. |
| 9,051,382 B2 * | 6/2015 | Trentmann ............... A61P 3/00 |
| 9,260,492 B2 | 2/2016 | Matschiner et al. |
| 9,549,968 B2 * | 1/2017 | Skerra .................... A61P 35/00 |

(Continued)

FOREIGN PATENT DOCUMENTS

| DE | 4417598 A1 | 12/1995 |
| DE | 19641876 A1 | 4/1998 |

(Continued)

OTHER PUBLICATIONS

Gebauer, M. et al., Combinatorial Design of an Anticalin Directed against the Extra-Domain B for the Specific Targeting of Oncofetal Fibronectin, J. Mol. Biol., 425: 780-802 (2013).
"Chain A Crystal Structure of Siderocalin (Ngal, Lipocalin 2) Complexed With Trencam-3,2-Hopo, A Cepabactin Analogue," GenBank Accession No. 1X71_A, Sep. 24, 2008.
Altschul et al., Gapped BLAST and PSI-BLAST: a new generation of protein database search programs, Nucleic Acids Res., 25(17):3389-3402 (1997).

(Continued)

Primary Examiner — Janet L Epps-Smith
(74) Attorney, Agent, or Firm — Honigman LLP; Douglas H. Siegel; Kelly T. Murphy

(57) ABSTRACT

The present invention relates to a novel library for the generation of muteins and to novel muteins derived from human lipocalin 2 (Lcn2, hNGAL) and related proteins that bind a given target with detectable affinity. The invention also relates to corresponding nucleic acid molecules encoding such a mutein and to a method for their generation. The invention further relates to a method for producing such a mutein. For example, such muteins may serve to bind and deplete pathological forms of natural biomolecules such as the amyloid beta peptide in Alzheimer's disease or may target the fibronectin extra-domain B, which is associated with tumor neovasculature.

21 Claims, 30 Drawing Sheets

Figure 3:
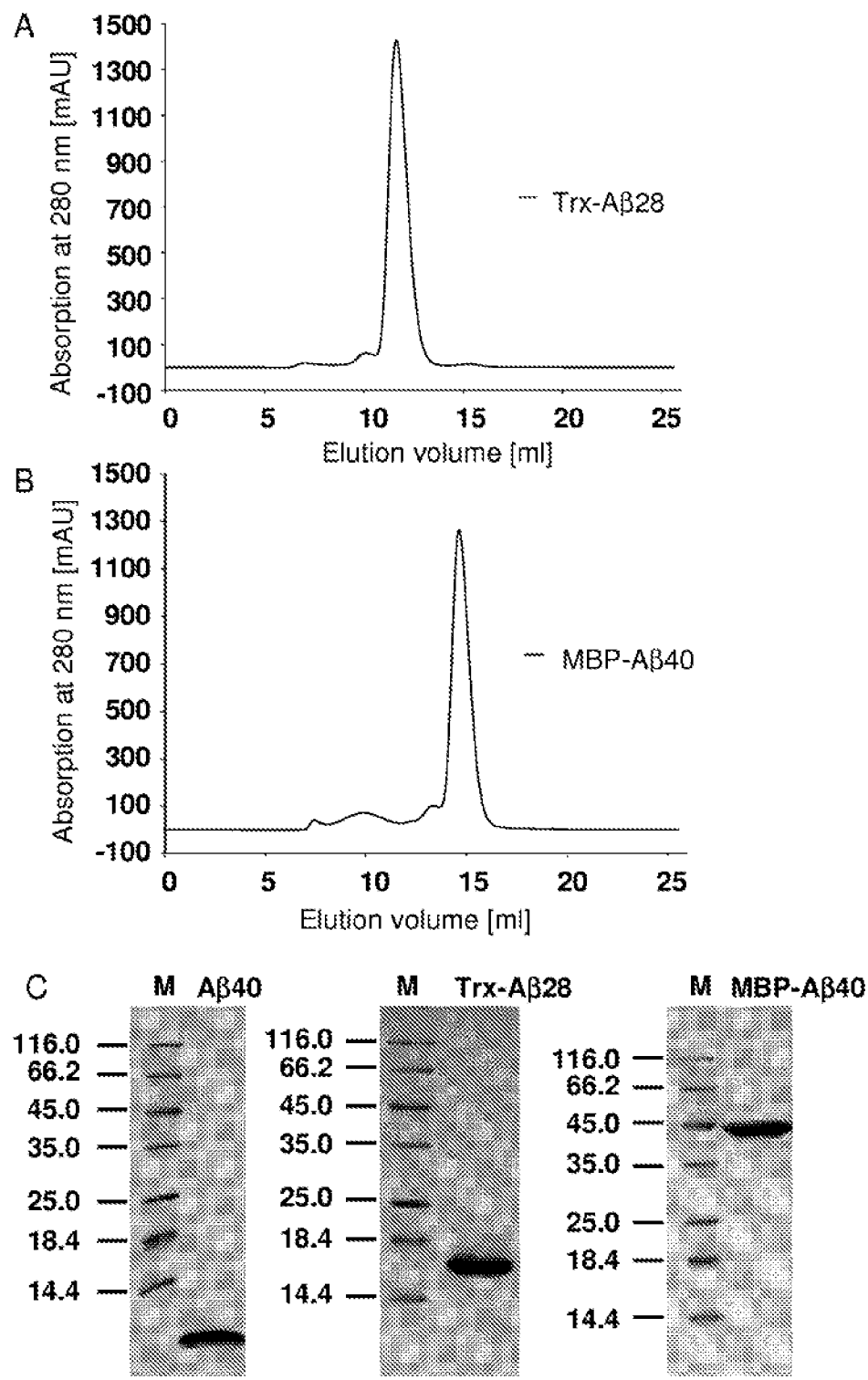

Specification includes a Sequence Listing.

(56) References Cited

U.S. PATENT DOCUMENTS

| | | | |
|---|---|---|---|
| 9,884,898 | B2 | 2/2018 | Corvey et al. |
| 10,273,275 | B2 | 4/2019 | Hinner et al. |
| 10,618,941 | B2 * | 4/2020 | Skerra .................. C07K 14/775 |
| 2003/0069395 | A1 | 4/2003 | Sato et al. |
| 2006/0058510 | A1 | 3/2006 | Skerra et al. |
| 2006/0088908 | A1 | 4/2006 | Skerra et al. |
| 2009/0042785 | A1 | 2/2009 | Matschiner et al. |
| 2010/0285564 | A1 | 11/2010 | Skerra et al. |
| 2011/0262353 | A1 | 10/2011 | Skerra et al. |
| 2012/0244596 | A1 | 9/2012 | Skerra et al. |
| 2013/0079286 | A1 | 3/2013 | Skerra et al. |
| 2013/0316962 | A1 | 11/2013 | Skerra et al. |
| 2014/0080177 | A1 | 3/2014 | Skerra et al. |
| 2017/0114109 | A1 | 4/2017 | Skerra et al. |
| 2017/0166615 | A1 | 6/2017 | Matschiner et al. |
| 2017/0369542 | A1 | 12/2017 | Trentmann et al. |
| 2018/0016312 | A1 | 1/2018 | Bel Aiba et al. |
| 2018/0141988 | A1 | 5/2018 | Hinner et al. |
| 2018/0148484 | A1 | 5/2018 | Hinner et al. |

FOREIGN PATENT DOCUMENTS

| | | | |
|---|---|---|---|
| DE | 19742706 | A1 | 4/1999 |
| DE | 19926068 | C1 | 1/2001 |
| EP | 0 330 451 | A2 | 8/1989 |
| EP | 0 361 991 | A2 | 4/1990 |
| JP | 2005503829 | A | 2/2005 |
| JP | 2007284351 | A | 11/2007 |
| WO | WO-96/23879 | A1 | 8/1996 |
| WO | WO-98/16873 | A1 | 4/1998 |
| WO | WO-99/16873 | A1 | 4/1999 |
| WO | WO-99/064016 | A1 | 12/1999 |
| WO | WO-00/075308 | A1 | 12/2000 |
| WO | WO-03/029462 | A1 | 4/2003 |
| WO | WO-03/029463 | A2 | 4/2003 |
| WO | WO-03/029471 | A1 | 4/2003 |
| WO | WO-03029462 | A1 * | 4/2003 ............. C07K 14/47 |
| WO | WO-2005/019254 | A1 | 3/2005 |
| WO | WO-2005/019255 | A1 | 3/2005 |
| WO | WO-2005/019256 | A2 | 3/2005 |
| WO | WO-2006/056464 | A2 | 6/2006 |
| WO | WO-2007/038619 | A2 | 4/2007 |
| WO | WO-2009/052390 | A1 | 4/2009 |
| WO | WO-2009052390 | A1 * | 4/2009 ............. C07K 14/47 |
| WO | WO-2009/156456 | A1 | 12/2009 |
| WO | WO-2012/022742 | A1 | 2/2012 |
| WO | WO-2012/065978 | A1 | 5/2012 |

OTHER PUBLICATIONS

Altschul, S. et al., Basic Local Alignment Search Tool; J. Mol. Biol., 215:403-410 (1990).

Amstutz, P. et al., In vitro display technologies: novel developments and applications, Curr. Opin. Biotechnol., 2001, 12:400-405.

Bachmann, Barbara J., Linkage Map of *Escherichia coli* K-12. Edition 8, Microbial. Rev., Jun. 1990, 54(2):130-197.

Beck, et al., Nucleotide Sequence and Genome Organisation of Filamentous Bacteriophages f1 and fd, Gene, vol. 16, pp. 35-58, 1981.

Beste, G. et al., Small antibody-like proteins with prescribed ligand specificities derived from the lipocalin fold, Proc. Natl. Acad. Sci. USA, Mar. 1999, 96:1898-1903.

Bittker, J. et al., Nucleic acid evolution and minimization by nonhomologous random recombination, Nat. Biotechnol., Oct. 2002, 20:1024-1029.

Bos et al., OctoDEX.TM.—Controlled Release of Pharmaceutical Proteins from Hydrogels, Business Briefing: Pharmatech, 2003:1-6.

Breustedt, D. et al., Comparative ligand-binding analysis of ten human lipocalins, Biochim. Biophys. Acta, 2006, 1764:161-173.

Broders, O et al., Hyperphage. Improving antibody presentation in phage display, Methods Mol. Biol., 2003, 205:295-302.

Brody et al., Active and Passive Immunotherapy for Neurodegenerative Disorders, Annu. Rev. Neurosci., 2008, 31:175-193.

Bruckdorfer, T., et al., From Production of Peptides in Milligram Amounts for Research to Multi-Tons Quantities for Drugs of the Future, Curr. Pharm. Biotechnol., 2004, 5:29-43.

Bullock, W. et al., XL1-Blue: A High Efficiency Plasmid Transforming recA *Escherichia coli* Strain with Beta-Galactosidase Selection, Biotechniques, 1987, 5(4):376-378.

Bundgaard, J.R. et al., Molecular Cloning and Expression of A cDNA Encode NGAL: A Lipocalin Expressed in Human Neutrophils, Biochemical and Biophysical Research Communications, Aug. 15, 1994, pp. 1468-1475, vol. 202, No. 3, XP002036694.

Carnemolla et al., Phage Antibodies with PAN-Species Recognition of the Oncofoetal Angiogenesis Marker Fibronectin ED-B Domain, Int. J. Cancer, 1996, 68:397-405.

Chan et al., The primary structure of rat $\alpha$ 2$\mu$ globulin-related protein, Nucleic Acids Research, vol. 16, No. 23, p. 11368, 1988.

Coles, et al., The Solution Structure and Dynamics of Human Neutrophil Gelatinase-associated Lipocalin, J. Mol. Biol., vol. 289, pp. 139-157, 1999.

Communication Pursuant to Article 94(3) EPC dated Jan. 5, 2015 issued in European Patent Application No. 09 769 304.8.

Corneillie et al., Irreversibly binding anti-metal chelate antibodies: Artificial receptors for pretargeting, Journal of Inorganic Biochemistry, May 1, 2006, 100(5-6):882-890.

Dennis, M. et al., Albumin Binding as a General Strategy for Improving the Pharmacokinetics of Proteins, J. Biol. Chem., Sep. 20, 2002, 277(38):35035-35043.

Dodel et al., Immunotherapy for Alzheimer's disease, Lancet Neurology, Apr. 2003, 2:215-220.

Ebbinghaus et al., Diagnostic and Therapeutic Applications of Recombinant Antibodies: Targeting the Extra-Domain B of Fibronectin, A Marker of Tumor Angiogenesis, Curr. Pharm. Des., 2004, 10:1537-1549.

Fitzgerald, Kevin, In Vitro Display Technologies—New Tools for Drug Discovery, Reviews, vol. 5, No. 6, pp. 253-258, Jun. 2000.

Fling, S. and Gregerson, D., Peptide and Protein Molecular Weight Determination by Electrophoresis Using a High-Molarity Tris Buffer System without Urea, Anal. Biochem., 1986, 155:83-88.

Flower, Darren R., Multiple Molecular Recognition Properties of the Lipocalin Protein Family, Journal of Molecular Recognition, 1995, 8:185-195.

Flower, Darren R., The lipocalin protein family: structure and function, Biochem. J., 1996, 318:1-14.

Frank, Ronald, The SPOT-synthesis technique Synthetic Peptide arrays on membrane supports—principles and applications, J. Immunol. Methods, 2002, 267:13-26.

Fuerteges, F. and Abuchowski, A., The Clinical Efficacy of Poly(Ethylene Glycol)-Modified Proteins,: J. Control. Release, 1990, 11:139-148.

Fujii, Phage display and beyond antibody-molecular target by antibody molecule, Seikagaku, 2010, vol. 82, No. 8, pp. 710-726, Abstract.

Gaillard, P. et al., Diphtheria toxin receptor-targeted brain drug delivery, International Congress Series., 2005, 1277:185-198.

Gaillard, P. et al., Targeted delivery across the blood-brain barrier, Expert Opin Drug Deliv., 2005, 2(2):299-309.

Gasteiger et al., ExPASy: the proteomics server for in-depth protein knowledge and analysis, Nucleic Acids Res., 2003, 31(13):3784-3788.

Gill, D. et al., Biopharmaceutical drug discovery using novel protein scaffolds, Curr. Opin. Biotechnol., 2006, 17(6):653-658.

Godovac-Zimmermann, Jasminka, The structural motif of $\beta$-lactoglobulin and retinol-binding protein: a basic framework for binding and transport of small hydrophobic molecules?, TIBS, Feb. 1988, vol. 13, pp. 64-66.

Goetz, D. et al., Ligand Preference Inferred from the Structure of Neutrophil Gelatinase Associated Lipocalin, Biochemistry, 2000, 39:1935-1941.

Gronwall et al., Selection and characterization of Affibody ligands binding to Alzheimer amyloid $\beta$ peptides, J. Biotechnol., 2007, 128:162-183.

(56) References Cited

OTHER PUBLICATIONS

Haass et al., Soluble protein oligomers in neurodegeneration: lessons from the Alzheimer's amyloid β-peptide, Nat. Rev. Mol. Cell. Biol., Feb. 2007, 8:101-112.
Hengen, Paul N., Methods and Reagents, Trends Biochem. Sci., vol. 21, pp. 75-76, 1996.
Hoess, Ronald H., Phage Display of Peptides and Protein Domains, Structural Biology, vol. 3, pp. 572-579, 1993.
Holzfeind, P. et al., Structural Organization of the Gene Encoding the Human Lipocalin Tear Prealbumin and Synthesis of the Recombinant Protein in *Escherichia coli*, Gene, vol. 139, pp. 177-183, 1994.
Hortschansky et al., The aggregation Kinetics of Alzheimer's β-amyloid peptide is controlled by stochastic nucleation, Protein Sci., 2005, 14:1753-1759.
Hoyer, W. et al., Stabilization of a β-hairpin in monomeric Alzheimer's amyloid-β peptide inhibits amyloid formation, Proc. Natl. Acad. Sci. USA, Apr. 1, 2008, 105(13):5099-5104.
Huber et al., Molecular Structure of the Bilin Binding Protein (BBP) from Pieris brassicae After Refinement at 2•0 Å Resolution, J. Mol. Biol., 1987, vol. 198, pp. 499-513.
International Search Report dated Nov. 27, 2009 in PCT/EP2009/057925, 3 pages.
Karlsson et al., Kinetic analysis of monoclonal antibody-antigen interactions with a new biosensor based analytical system, J. Immunol. Methods, 1991, 145:229-240.
Kaspar et al., Fibronectin as target for tumor therapy, Int. J. Cancer, 2006, 118:1331-1339.
Kaufman et al., Transgenic Analysis of 100-kb Human beta-Globin Cluster-Containing DNA Fragment Propagated as a Bacterial Artificial Chromosome, Blood, 1999, 94:3178-3184.
Khurana et al., Mechanism of thioflavin T binding to amyloid fibrils, J. Struct. Biol., 2005, 151:229-238.
Kim, H. et al., High-Affinity Recognition of Lanthanide(III) Chelate Complexes by a Reprogrammed Human Lipocalin 2, J. Am. Chem. Soc., 2009, 131:3565-3576.
Kjelsden, L. et al., Human Neutrophil Gelatinase-Associated Lipocalin and Homologous Proteins in Rat and Mouse, Biochimica et Biophysica Acta, vol. 1482, pp. 272-283, 2000.
Konig, T. and Skerra, A., Use of an albumin-binding domain for the selective immobilization of recombinant capture antibody fragments on ELISA plates, J. Immunol. Methods, 1998, 218:73-83.
Korean Office Action issued in corresponding application No. 10-2012-7017730 dated Jul. 28, 2018 with English translation.
Korndoerfer et al., "Crystallographic Analysis of an Anticalin" with Tailored Specificity for Fluorescein Reveals High Structural Plasticity of the Lipocalin Loop Region, Proteins: Structure, Function and Bioinformatics, 2003, vol. 53, pp. 121-129.
Korndoerfer et al., Structural Mechanism of Specific Ligand Recognition by a Lipocalin Tailored for the Complexation of Digoxigenin, J. Mol. Biol., 2003, vol. 330, pp. 385-396.
Kraulis, et al., The Serum Albumin-Binding Domain of Streptococcal Protein G is a Three-Helical Bundle: A Heteronuclear NMR Study, FEBS Letters, vol. 378, pp. 190-194, 1996.
Lazar et al. Transforming Growth Factor α: Mutation of Aspartic Acid 47 and Leucine 48 Results in Different Biological Activities, Molecular and Cellular Biology, Mar. 1988, 8(3):1247-1252.
Leahy et al., Crystallization of a Fragment of Human Fibronectin: Introduction of Methionine by Site-Directed Mutagenesis to Allow Phasing via Selenomethionine, Proteins, 1994, 19:48-54.
Lichtlen et al., Antibody-based approaches in Alzheimer's research: safety, pharmacokinetics, metabolism, and analytical tools, J. Neurochem., 2007, 104:859-874.
Lohrengel, B. et al., Expression and Purification of Woodchuck Tumour Necrosis Factor Alpha, Cytokine, vol. 12, No. 6, pp. 573-577, Jun. 2000.
Low, N. et al., Mimicking Somatic Hypermutation: Affinity Maturation of Antibodies Displayed on Bacteriophage Using a Bacterial Mutator Strain, J. Mol. Biol., vol. 260, pp. 359-368, 1996.
Lowman, H.B. Bacteriophage display and discovery of peptides leads for drug development, Annu. Rev. Biophys. Biomol. Struct., 1997, 26:401-424.
Mateo, C. et al., Removal of Amphipathic Epitopes from Genetically Engineered Antibodies: Production of Modified Immunoglobulins with Reduced Immunogenicity, Hybridoma, 2000, 19(6):463-471.
Meidan et al., Emerging Technologies in Transdermal Therapeutics, Am. J. Ther., 2004, 11(4):312-316.
Mercader et al., Generation of anticalins with specificity for a nonsymmetric phthalic acid ester, Analytical Biochemistry, 2002, vol. 308, 269-277.
Moretto et al., Conformation-sensitive Antibodies against Alzheimer Amyloid-β by Immunization with a Thioredoxin-constrained B-cell Epitope Peptide, J. Biol. Chem., 2007, 282(15):11436-11445.
Muller, H. et al. Functional Expression of the Uncomplexed Serum Retinol-binding Protein in *Escherichia coli*, J. Mol. Biol., 1993, vol. 230, pp. 725-732.
Muller, H. et al., Grafting of a High-Affinity Zn(II)-Binding Site on the β-Barrel of Retinol-Binding Protein Results in Enhanced Folding Stability and Enables Simplified Purification, Biochemistry, 1994, vol. 33, pp. 14126-14135.
Murakami, H. et al., Random insertion and deletion of arbitrary number of bases for codon-based random mutation of DNAs, Nat. Biotechnol., Jan. 2002, 20:76-81.
Ngo, T. et al., Computational Complexity, Protein Structure Prediction, and the Levinthal Paradox, The Protein Folding Problem and Tertiary Structure Prediction, pp. 492-495 (1994).
Notice of Reasons for Rejections dated Jan. 20, 2015 issued in Japanese Application No. 2012-542505, with English translation.
Osborn, B. et al., Pharmacokinetic and Pharmacodynamic Studies of a Human Serum Albumin-Interferon-α Fusion Protein in Cynomolgus Monkeys, J. Pharmacol. Exp. Ther., 2002, 303(2):540-548.
Paine et al., The Lipocalin website, Elsevier Science B.V., Biochimica et Biophysica Acta 1482, pp. 351-352, 2000.
Papiz, et al., The Structure of Beta-Lactoglobulin and Its Similarity to Plasma Retinol-Binding Protein, Nature, vol. 324, pp. 383-385, 1986.
Pervaiz, et al., Homology and Structure-Function Correlations Between α1-Acid Glycoprotein and Serum Retinol-Binding Protein and Its Relatives, 1987, The FASEB journal 1.3 (1987):209-214.
Pini et al., Design and Use of a Phage Display Library, J. Biol. Chem., Aug. 21, 1998, 273(34):21769-21776.
Pini, A. et al., Phage Display and Colony Filter Screening for High-Throughput Selection of Antibody Libraries, Comb. Chem. High Throughput Screen., 2002, 5:503-510.
Pujuguet et al., Expression of Fibronectin ED-A+ and ED-B+ Isoforms by Human and Experimental Colorectal Cancer, Am. J. Pathol., Feb. 1996, 148(2):579-592.
Ramoni, R. et al., The protein scaffold of the lipocalin odorant-binding protein is suitable for the design of new biosensors for the detection of explosive components, J. Phys. Condens. Matter, 19: 8 pages (2007).
Redl, Bernhard, Human tear lipocalin, Biochim. Biophys. Acta, 2000, 1482:241-248.
Roberts, Richard W., Totally In Vitro Protein Selection Using mRNA-Protein Fusions and Ribosome Display, Current Opinion in Chemical Biology, vol. 3, pp. 268-273, 1999.
Rodi, D. and Makowski, L., Phage-display technology—finding a needle in a vast molecular haystack, Curr. Opin. Biotechnol., 1999, 10:87-93.
Schlehuber et al., Lipocalins in drug discovery: from natural ligand-binding proteins to 'anticalins', Drug Discovery Today, 10(1):23-33 (2005).
Schlehuber, S. and Skerra, A. et al., Duocalins, engineered ligand-binding proteins with dual specificity derived from the lipocalin fold, Biol. Chem., Sep. 2001, 382:1335-1342.
Schlehuber, S. and Skerra, A., Tuning ligand affinity, specificity, and folding stability of an engineered lipocalin variant—a so-called 'anticalin'—using a molecular random approach, Biophysical Chemistry 96 (2002) 213-228.

(56) References Cited

OTHER PUBLICATIONS

Schlehuber, S. et al., A Novel Type of Receptor Protein, Based on the Lipocalin Scaffold, with Specificity for Digoxigenin, J. Mol. Biol., 2000, 297:1105-1120.
Schliemann et al., Antibody-based targeting of the tumor vasculature, Biochim. Biophys. Acta, 2007, 1776:175-192.
Schmidt et al., The Strep-tag system for one-step purification and high-affinity detection of capturing of proteins, Nat. Protoc., 2007, 2(6):1528-1535.
Schmidt, F. et al., The bilin-binding protein of Pieris brassicae cDNA sequence and regulation of expression reveal distinct features of this insect pigment protein, Eur. J. Biochem., 1994, 219:855-863.
Schmidt, T. et al., Molecular Interaction Between the Strep-tag Affinity Peptide and its Cognate Target, Streptavidin, J. Mol. Biol., 1996, 255:753-766.
Schoepfer, Ralf, The pRSET Family of T7 Promoter Expression Vectors for *Escherichia coli*, Gene, vol. 124, pp. 83-85, 1993.
Schonfeld, D. et al. An engineered lipocalin specific for CTLA-4 reveals a combining site with structural and conformational features similar to antibodies, PNAS, 106(20): 8198-8203 (2009).
Sivaprasadarao, A. et al., Lipocalin structure and function, Biochemical Society Transactions, 1990. pp. 619-622.
Skerra et al., 'Anticalins': a new class of engineered ligand-binding proteins with antibody-like properties, Reviews in Molecular Biotechnology, 2001, 74:257-275.
Skerra, A., Engineered protein scaffolds for molecular recognition, J. Mol. Recognit., 2000; 13:167-187.
Skerra, A., et al., Lipocalins as a scaffold, Elsevier Science B.V., Biochimica et Biophysica Acta 1482, pp. 337-350, 2000.
Skerra, Alternative binding proteins: Anticalins—harnessing the structural plasticity of the lipocalin ligand pocket to engineer novel binding activities; FEBS Journal, 275(11): 2677-2683 (Jun. 2008).
Skerra, Anticalins as alternative binding proteins for therapeutic use; Current Opinion in Molecular Therapeutics, 9(4): 336-344 (Aug. 2007).
Skerra, Arne, Use of the tetracycline promoter for the tightly regulated production of a murine antibody fragment in *Escherichia coli*, Gene, 1994, 151:131-135.
Skerra, et al., Filter Screening of Antibody Fab Fragments Secreted From Individual Bacterial Colonies: Specific Detection of Antigen Binding with a Two-Membrane System, Anal. Biochem., vol. 196, pp. 151-155, 1991.
Stoesz, S. et al., Overexpression of neu-related lipocalin (NRL) in neu-initiated but not ras or chemically initiated rat mammary carcinomas, Oncogene (1995), 11, pp. 2233-2241.
Studier, F.W., and Moffatt, B.A., Use of Bacteriophage T7 RNA Polymerase to Direct Selective High-level Expression of Cloned Genes, J. Mol. Biol., 1986, 189:113-130.
Stump et al., Site-directed Mutagenesis of Rat Cellular Retinol-binding Protein, J. Biol. Chem., Mar. 1991, 266(7):4622-4630.
Tartof et al., Improved Media for Growing Plasmid and Cosmid Clones, Focus, Bethesda Research Laboratory, 1987, 9(2):12.
Tulasne, D. et al., C-Terminal Peptide of Thrombospondin-1 Includes Platelet Aggregation Through the Fc Receptor γ-Chain-Associated Signaling Pathway and by Agglutination, Blood, vol. 98, No. 12, pp. 3346-3352, Dec. 1, 2001.
Vajo, Z. and Duckworth, W., Genetically Engineered Insulin Analogs: Diabetes in the New Millennium, Pharmacol. Rev., 2000, 52(1):1-9.
Venturi, M. et al., High Level Production of Functional Antibody Fab Fragments in an Oxidizing Bacterial Cytoplasm, J. Mol. Biol., 2002, 315:1-8.
Virnekas et al., Trinucleotide phosphoramidites: ideal reagents for the synthesis of mixed oligonucleotides for random mutagenesis, Nucleic Acids Res, 1994, 22(25):5600-5607.
Vogt, M. and Skerra, A., Construction of an Artificial Receptor Protein ("Anticalin") Based on the Human Apolipoprotein D, ChemBioChem, 5: 191-199 (2004).
Voss, et al., Mutagenesis of a Flexible Loop in Streptavidin Leads to Higher Affinity for the Strep-Tag II Peptide and Improved Performance in Recombinant Protein Purification, Protein Engineering, vol. 10, No. 8, pp. 975-982, 1997.
Wang et al., Expanding the Genetic Code of *Escherichia coli*, Science, Apr. 20, 2001, 292:498-500.
Wang et al., Expanding the genetic code, Chem. Comm., 2002, 1:1-11.
Wang et al., Rapid analysis of gene expression (RAGE) facilitates universal expression profiling, Nucleic Acids Research, 1999, 27(23):4609-4618.
Wang, A. M. et al., Molecular Cloning of the Complementary DNA for Human Tumor Necrosis Factor, Science, vol. 228, pp. 149-154, 1985 (Abstract).
Wells, J. et al., Rapid Evolution of Peptide and Protein Binding Properties In Vitro, Current Opinion in Structural Biology, vol. 2, pp. 597-604, 1992.
Wells, James A., Additivity of Mutational Effects in Proteins, Biochemistry, Sep. 18, 1990, 29(37):8509-8517.
Wilson, D. et al., The use of mRNA display to select high-affinity protein-binding peptides, Proc. Natl. Acad. Sci. USA, Mar. 27, 2001, 98(7):3750-3755.
Wu et al., Construction of phage-displayed library based on the lipocalin scaffold and screening anticalins with specificity for carbofuran, Gaodeng Xuexiao Huaxue Xuebao (2008), 29(3), 528-532; abstract only.
Yanisch-Perron, C. et al., Improved M13 phage cloning vectors and host strains: nucleotide sequences of the M13mp18 and pUC19 vectors, Gene, 1985, 33:103-119.
Zaccolo, M. et al., An Approach to Random Mutagenesis of DNA Using Mixtures of Triphosphate Derivatives of Nucleoside Analogues, J. Mal. Biol., 1996, 255:589-603.
Zardi, L. et al., Transformed human cells produce a new fibronectin isoform by preferential alternative splicing of a previously unobserved exon, EMBO J, 6(8):2337-42 (1987).

\* cited by examiner

FIG. 1

```
  1 CCAATTCCATGGGAAATGGTATGTCGTGGGCnnnGCCGGAAATnnnnnnCTGCGTGAGGATAAGGATCCGnnnAAAATGnnnGCCGACCAT  90
    +---------+---------+---------+---------+---------+---------+---------+---------+---------+
    GGTTAAGGTACCCTTTACCATACAGCACCCGGACCCGGACGCACCGGCCTTTACGGTAAGACGCACTCCTATTCCTAGGCGTCTTTACATACGCTGGTA
    GlnPheHisGlyLysTrpTyrValGlyXaaAlaGlyAsnXaaXaaLeuArgGluAspLysAsnXaaXaaMetXaaAlaThrIle
                        8                     12 13                          21       24

91 TTACGAGTTGAAAGAAGAGATAAATCATATATAACGTCACCnnnGTGnnnTTTnnnnnnAAGAAATGCnnnTACnnnATTnnnACCTTTGTGCC 180
    +---------+---------+---------+---------+---------+---------+---------+---------+---------+
    AATGCTCAACTTTCTTCTATTTAGTATATTGCAGTGGAGGCACAACAAAGCGTTTTCTTTACGCTGATGACCTAAGCATGAAACACGG
    TyrGluLeuLysGluAspLysSerTyrAsnValThrXaaValXaaPheXaaAlaXaaLysCysXaaLysXaaIleXaaThrPheValPro
                    40       42   44 45                              49      51     53

181 GGGGAGCCAGCCCGGCCGAGTTTACTTTAGGCnnnATTAAAAGTnnnACATCAnnnTTGGTCCCGGTCGTGAGCACCAACTA 270
    +---------+---------+---------+---------+---------+---------+---------+---------+
    CCCCTCGGTCGGGCCGGCGCTCAAATGAAATTCCGTTGTAATTTTCAATGGGCCGGACTGTAGTATGAACCAGGCGCAGCACTCGTGGTTGAT
    GlySerGlnProGlyGluPheThrLeuGlyXaaIleLysSerXaaProGlyXaaThrSerXaaLeuValArgValValSerThrAsnTyr
                    68                     72    75                      78

271 CAACCAGCAGCCATGGTGTTCTTCAAGnnnGTGnnnCAGAACCGGCGAGnnnTTTnnnATCACACTGTACGGGCGCACGAAAGAACTGAC 360
    +---------+---------+---------+---------+---------+---------+---------+---------+
    GTTGGTCGTCGGTACCACAAGAAGTTCTTTCACAGGGTCTTGGCCGCTCATGAAATTCTAGTGTGACATGCCCGCGTGCTTTCTTGACTG
    AsnGlnHisAlaMetValPhePheLysXaaValXaaArgGlnAsnArgXaaPheXaaIleThrLeuTyrGlyArgThrLysGluLeuThr
                        97  99                        104   106

361 AAGCGAGCTGAAGGAAAAATTTATCCGCTTTTCCAAATCTCTGG 404
    +---------+---------+---------+---------+---
    TTCGCTCGACTTCCTTTTTAAAATAGGCGAAAAGGTTTAGAGACC
    SerGluLeuLysGluAsnPheIleArgPheSerLysSerLeu
```

FIG. 2

```
            1         10        20        30        40        50        60        70        80        90
Lcn2        QDSTSDLIPAPPLSKVPLQQNFQDNQFQGKWYVVGLAGNAILREDKDPQKMYATIYELKEDKSYNVTSVLFRKKKCDYWIRTFVPGCQPG
Lib         ..................................h...........x...x.....x...........x..xx....x.x.x...s
S1-A4(Abeta)..................................h.........V..YT....L.Y..........S.G.RL..N.K.R...s
US7(Abeta)  ..................................h.........V..KS....W.Y..........S.G.GT..H.K.R...s
H1-G1(Abeta)..................................h.........C..VL....L.Y..........S.G.DD..L.K.R...s
N7A(ED-B)   ..................................h.........K..HD....R.Q..........N.R.VH..N.R.W...s
N7E(ED-B)   ..................................h.........E..SL....R.Y..........S.R.RS..H.L.R...s
N9B(ED-B)   ..................................h.........R..MR....A.V..........K.M.QR..K.M.N...s
N10D(ED-B)  ..................................h.........A..TW....Y.Q..........N.L.MS..R.M.H...s
                                              ===A=======#1=======B====      ===C====#2=======D===

100       110       120       130       140       150       160       170
Lcn2        EFTLGNIKSYPGLTSYLVRVVSTNYNQHAMVFFKKVSQNREYFKITLYGRTKELTSELKENFIRFSKSLGLPENHIVFPVFIDQCIDG
Lib         ...x...x.x.x.........x..x..x...x.x.........................
S1-A4       ...I...Q..M.Y........T.G..M.N..............................
US7         ...R...R..R.A........V.Q..S.N..............................
H1-G1       ...R...E..G.W........E.A..T.N..............................
N7A         ...N...W..L.W........R.Y..L.E.........N....................
N7E         ...L...K..H.F........T.A..Y.F..............................
N9B         ...A...P..P.T........H.F..Y.H..............................
N10D        ...S...W..L.W........R.Y..F.G..............................
            ===E=====#3===F===   ===G=====#4======H===
```

FIG. 17

FIG. 18
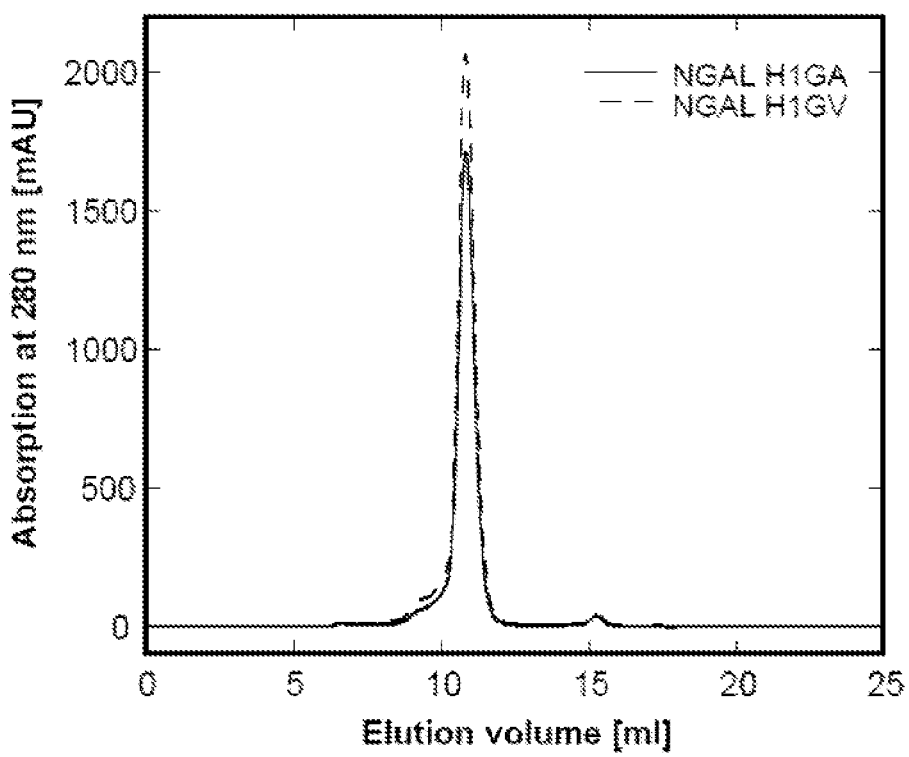
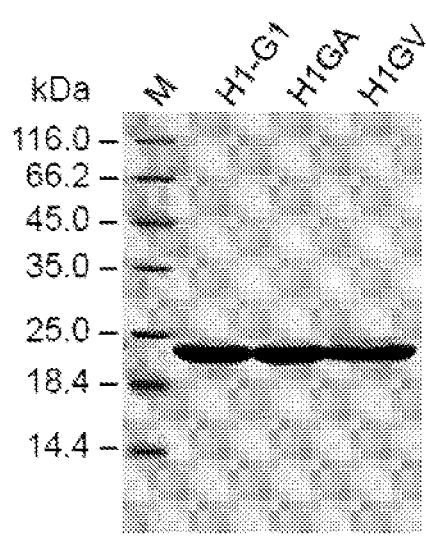

FIG. 20
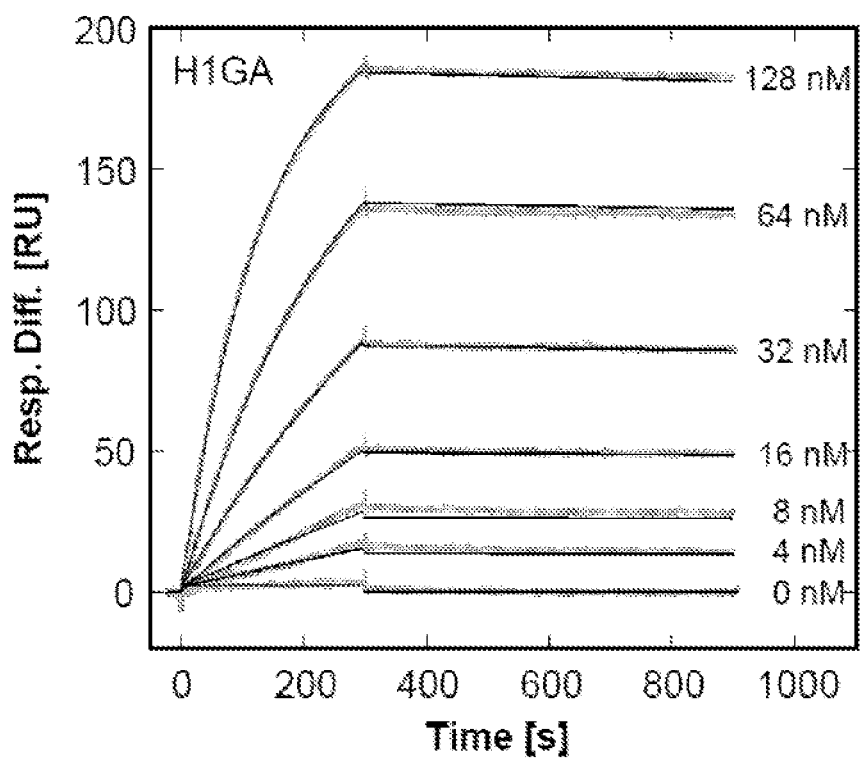
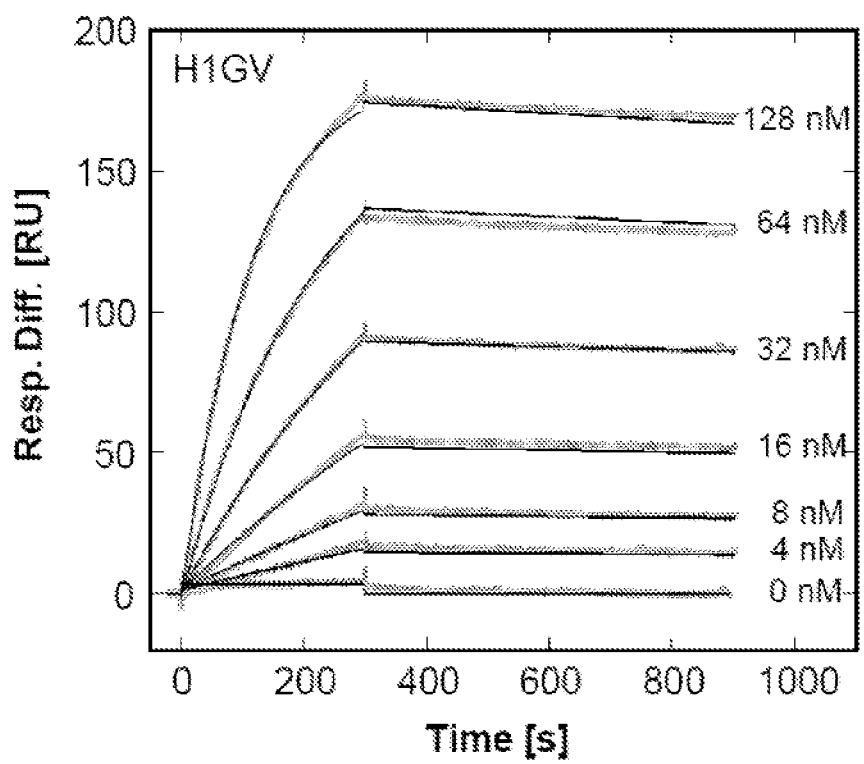

FIG. 22
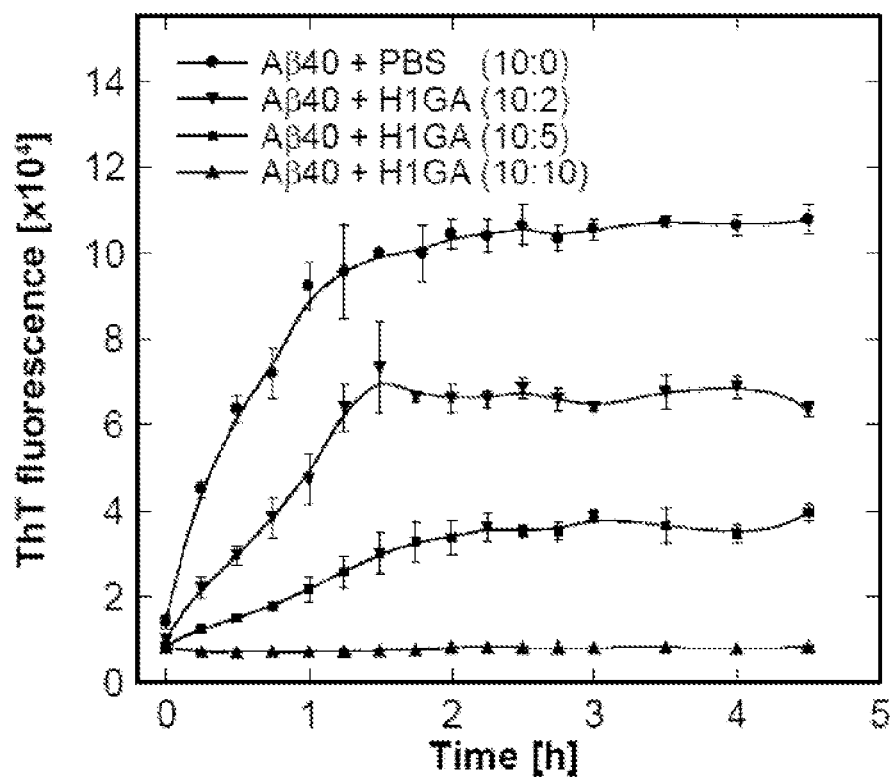
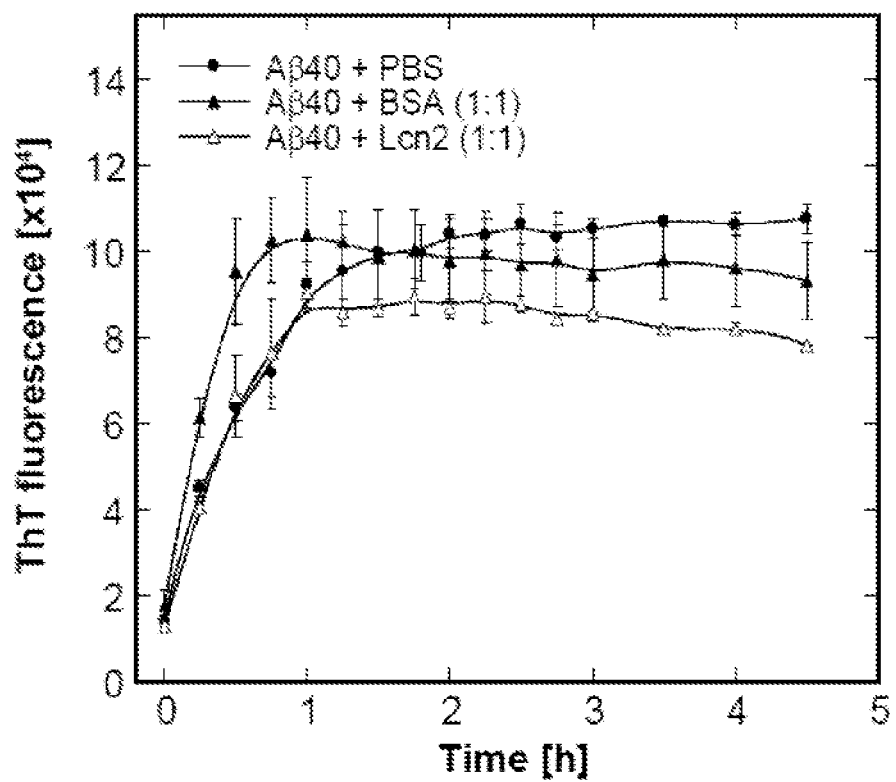

FIG. 23

|  | $K_D$ [nM] | |
| --- | --- | --- |
|  | H1GA | H1GV |
| Aβ40 (Capture ELISA, Fig 19) | 4.2 ± 0.3 | 4.9 ± 0.3 |
| Trx-Aβ28 (Capture ELISA, Fig 19) | 3.8 ± 0.4 | 4.2 ± 0.4 |
| MBP-Aβ40 (SPR, Fig 20) * | 0.48 | 1.1 |
| Aβ40 (SPR, Fig 21) ** | 0.095 | - |

\* dissociation time not sufficiently long
\*\* value more reliable since dissociation time long enough

FIG. 24

```
              1            10        20        30        40        50        60        70        80      90
Lcn2    QDSTSDLIPAPPLSKVPLQQNFQDNQFQGKWYVVGLAGNAILREDKDPQKMYATIYELKEDKSYNVTSVLFRKKKCDYWIRTFVPGCQPG
Lib     .................................h.......x..xx....x.x..........x.xx....x.x..x........s
S1-A4   .................................h.......V..YT....L.Y..........S.G.RL..N.K.R........s
US7     .................................h.......V..KS....W.Y..........S.G.GT..H.K.R........s
H1-G1   .................................h.......C..VL....L.Y..........S.G.DD..L.K.R........s
H1GA    .................................h.......A..VL....L.Y..........S.G.DD..L.K.R........s
H1GV    .................................h.......V..VL....L.Y..........S.G.DD..L.K.R........s
N7A     .................................h.......K..HD....R.Q..........N.R.VH..N.R.W........s
N7E     .................................h.......E..SL....R.Y..........S.R.RS..H.L.R........s
N9B     .................................h.......R..MR....A.V..........K.M.QR..K.M.N........s
N10D    .................................h.......A..TW....Y.Q..........N.L.MS..R.M.H........s
                                        ====A=========#1---------=B===                ===C=====#2------=D===

100       110       120       130       140       150       160       170
Lcn2    EFTLGNIKSYPGLTSYLVRVVSTNYNQHAMVFFKKVSQNREYFKITLYGRTKELTSELKENFIRFSKSLGLPENHIVFPVPIDQCIDG
Lib     ....x..x.x.x....x................x.x....x.x............................N.............
S1-A4   ....I..Q..M.Y....................T.G..M.N............................................
US7     ....R..R.R.A.....................V.Q..S.N............................................
H1-G1   ....R..E.G..W....................E.A..T.N............................................
H1GA    ....R..E.G..W....................E.A..T.N............................................
H1GV    ....R..E.G..W....................E.A..T.N............................................
N7A     ....N..W.L..W....................R.Y..L.E...........N................................
N7E     ....L..K.H.F.....................T.A..Y.F............................................
N9B     ....A..P.P.T.....................H.F..H.H............................................
N10D    ....S..W.L..W....................R.Y..G..............................................
        ===E-----#3---------=F====       ===G=======#4---==H===
                                                     Time (s)
```

FIG. 25

```
        1           10        20        30        40        50        60        70        80        90
Lcn2    QDSTSDLIPAPPLSKVPLQQNFQDNQFQGKWYVVGLAGNAILREDKDPQKMYATIYELKEDKSYNVTSVLFRKKKCDYWIRTFVPGCQPG
Lib     ...................................h........x....x.x........................x.x.xx........
H1-G1   ...................................h........C...VL.Y.........................S.G.DD..L.K.R....S
H1GA    ...................................h........A...VL.Y.........................S.G.DD..L.K.R....S
H1GV    ...................................h........V...VL.Y.........................S.G.DD..L.K.R....S
                                           ===A====----#1-----====B====----====C====----#2---====D===

100       110       120       130       140       150       160       170
Lcn2    EFTIGNIKSYPGLTSYLVRVVSTNYNQHAMVFFKKVSQNREYFKITLYGRTKELTSELKENFIRFSKSLGLPENHIVFPVPIDQCIDG
Lib     ....x....x..x..x......................x..x....
H1-G1   ....R..E..G..W................E.A...T.N........
H1GA    ....R..E..G..W................E.A...T.N........
H1GV    ....R..E..G..W................E.A...T.N........
        ===E=---#3----====F====    ===G====----#4---====H===
```

Figure 27:
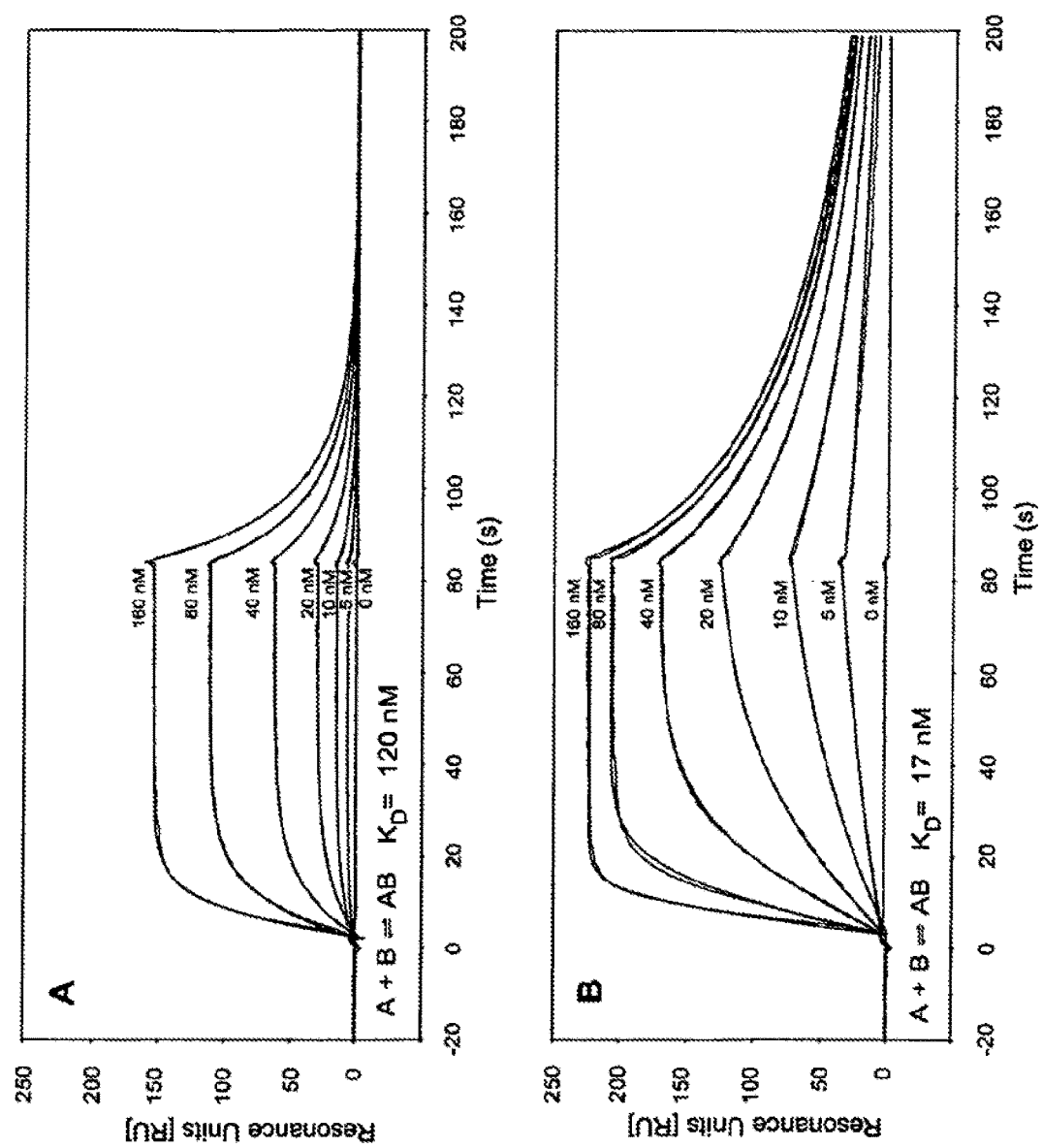

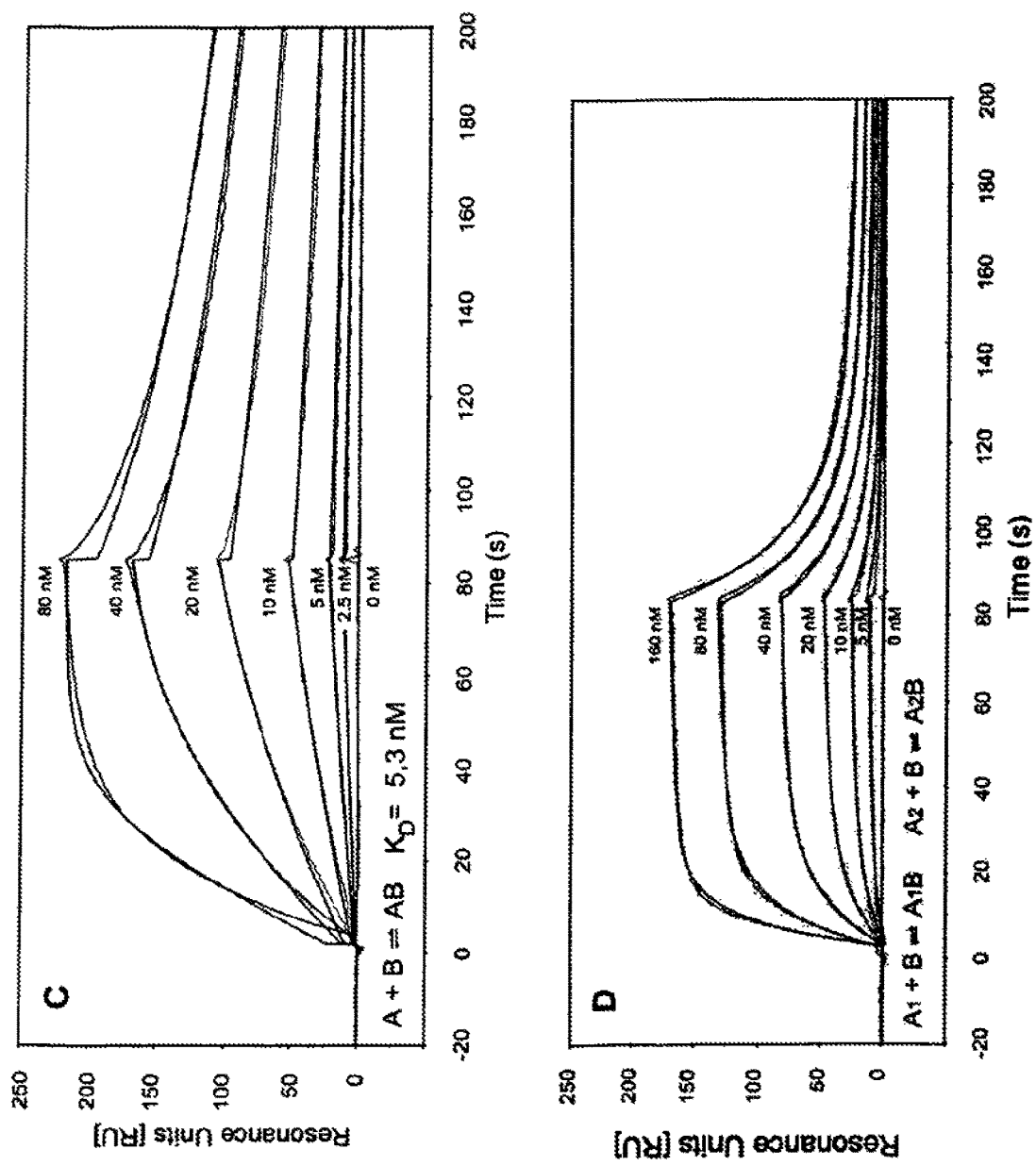
FIG. 27 (Contd)

Figure 28:
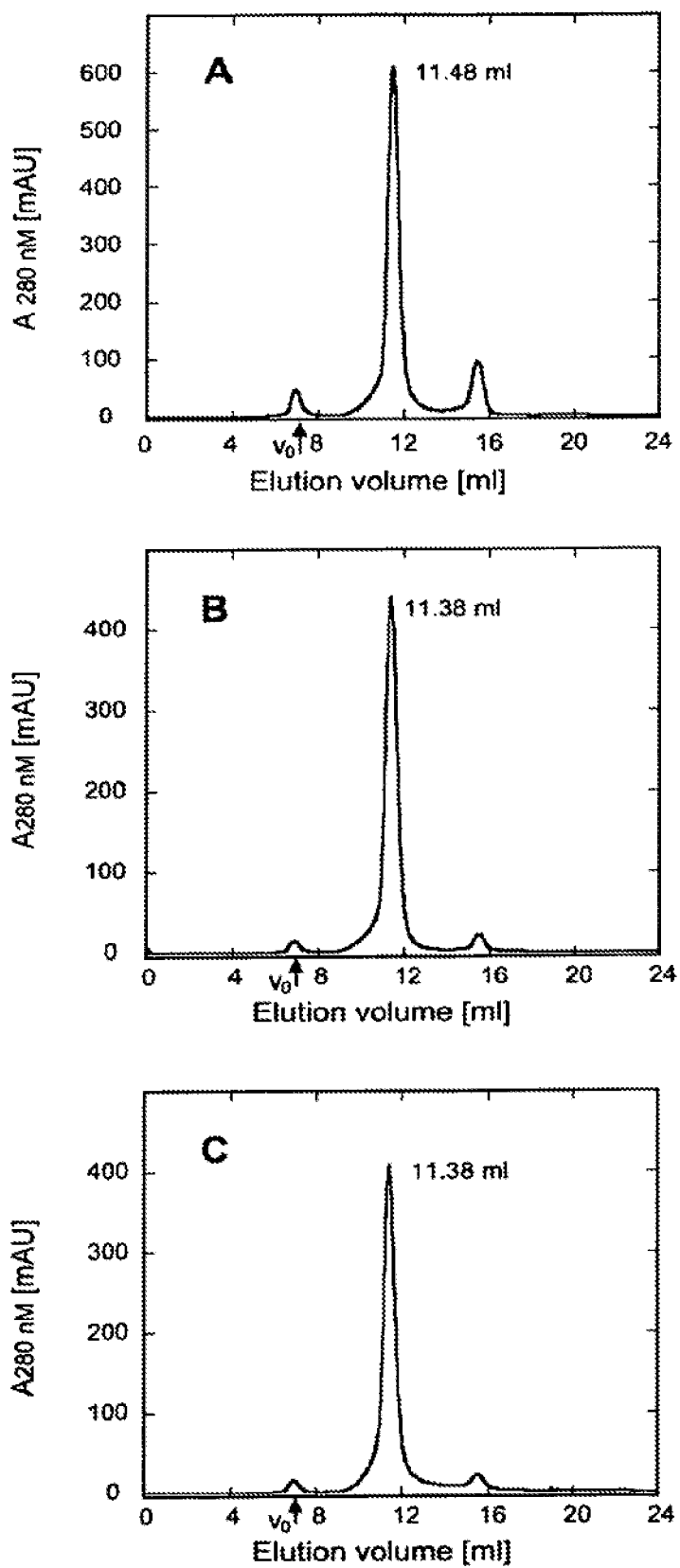

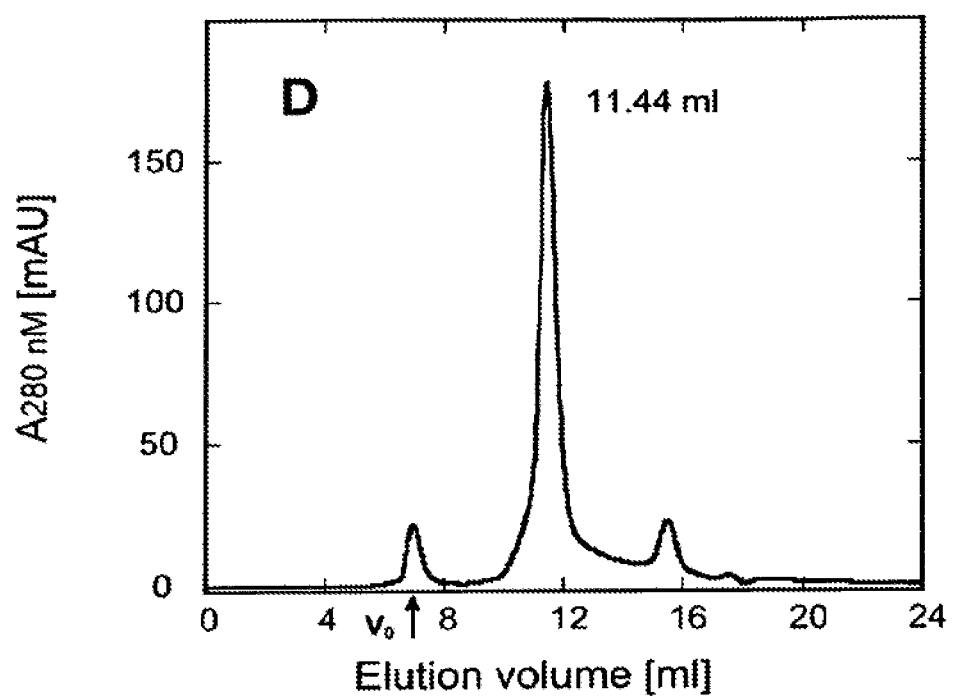
FIG. 28 (contd)

MUTEINS OF HUMAN LIPOCALIN 2 (LCN2, HNGAL) WITH AFFINITY FOR A GIVEN TARGET

CROSS-REFERENCE TO RELATED PATENT APPLICATIONS

This application is a Continuation of U.S. application Ser. No. 15/380,168, filed Dec. 15, 2016, which is a Continuation of U.S. application Ser. No. 13/514,133 filed Aug. 21, 2012, now U.S. Pat. No. 9,549,968, which is the U.S. National Stage of PCT/EP2010/069028, filed Dec. 7, 2010, which claims priority from Provisional U.S. Application 61/267,098, filed Dec. 7, 2009, all of which applications are incorporated herein by reference in its entirety.

The instant application contains a Sequence Listing which has been submitted in ASCII format via EFS-WEB and is hereby incorporated by reference in its entirety. Said ASCII copy, created on Nov. 20, 2012 is named sequence.txt and is 88 KB.

SUMMARY

The present invention relates to a novel library for the generation of muteins and to novel muteins derived from human lipocalin 2 (Lcn2, hNGAL) and related proteins that bind a given target with detectable affinity. The invention also relates to corresponding nucleic acid molecules encoding such a mutein and to a method for their generation. The invention further relates to a method for producing such a mutein. Furthermore, the invention is directed to a pharmaceutical composition comprising such a lipocalin mutein as well as to various uses of the mutein.

Lcn2 muteins according to this invention show potential as therapeutic and/or diagnostic reagents in several disease areas. For example, they may serve to bind and deplete pathological forms of natural biomolecules such as the amyloid beta peptide in Alzheimer's disease. In another example they may be employed for the specific targeting of various labels or toxins to disease-related cell surface markers such as the fibronectin extra-domain B, which is associated with tumor neovasculature. Due to the particular benefits of the Lcn2 muteins that can be generated according to this invention various other applications or examples are possible.

BACKGROUND

Alzheimer's disease (AD) is the most common form of dementia in the elderly population. Associated with AD is the defective processing of the amyloid precursor protein giving rise to the potentially neurotoxic, 40-42 residues encompassing amyloid beta peptide (Aβ). Subsequent aggregation of Aβ to oligomers and long fibrils plays a pivotal role in the course of the disease, culminating in the formation of senile plaques (Haass and Selkoe (2007) *Nat. Rev. Mol. Cell. Biol.* 8, 101-112). Despite the increasing significance of AD there is still an unmet need for effective therapies to prevent, cure or decelerate this dementia.

Current anti-amyloid approaches aim at (i) the prevention of Aβ formation, (ii) blocking of its aggregation, (iii) reduction of soluble Aβ levels in the brain, and (iv) disassembly of existing amyloid plaques. So far, immunotherapies, comprising both active and passive immunization of AD patients, have been most promising in this field (Dodel et al. (2003) *Lancet Neurology* 2, 215-220; Lichtlen and Mohajeri (2007) *J. Neurochem.* 104, 859-874; Brody and Holtzmann (2008) *Annu. Rev. Neurosci.* 31, 175-193). However, recent clinical trials with active immunization of AD patients were ceased due to the incidence of meningoencephalitis in 6% of the patients. Due to these potential adverse side effects of Fc-mediated immunological functions, non-Ig binding reagents, such as Anticalins, provide an alternative. The identification of an Affibody molecule with specificity for amyloid beta is one example to illustrate the potential of engineered non-Ig binding proteins (Grönwall et al (2007) *J. Biotechnol.* 128, 162-183; Hoyer et al. (2008) *Proc. Natl. Acad. Sci. USA* 105, 5099-5104).

However, the bacterial origin of Affibodies may cause problems with immunogenicity in human patients.

Fibronectin (FN) plays an essential role in cell adhesion, migration, proliferation, and differentiation. FN is a large, modular, dimeric glycoprotein comprising multiple domains of type I, II, and II. Alternative splice variants of FN such as its extra-domain B (ED-B), which is incorporated between the $FN^{III}7$ and $FN^{III}8$ domains, are expressed in a tissue-specific and developmental stage-dependent manner (Zardi et al. (1987) *EMBO J* 6, 2337-2342).

ED-B is absent from normal adult tissue except during wound healing and neoplastic vascularization. Consequently, ED-B containing fibronectin is abundantly expressed in many different tumor types that attract neovascularization and undergo aberrant angiogenesis. While the actual biological function of ED-B in angiogenesis remains elusive, its incorporation into FN serves as excellent marker for tumorgenesis. Generally, discrimination between malignant tissues and healthy organs is an advantageous therapeutic strategy as the selective targeting of drugs directly to the tumor tissue leads to an increased local drug concentration.

In order to specifically detect and target ED-B, recombinant antibody fragments were raised using phage display antibody technology. One of the isolated antibody fragments is the L19 single chain Fv (Carnemolla et al. (1996) *Int. J. Cancer* 68, 397-405; Ebbinghaus et al. (2004) *Curr. Pharm. Des.* 10, 1537-1549). Addressing ED-B by L19 in combination with an effective cytotoxic agent currently shows prospects for cancer therapy and diagnostics (Schliemann and Neri (2007) *Biochim. Biophys. Acta* 1776, 175-192; Kaspar et al. (2006) *Int. J Cancer* 118, 1331-1339).

However, the L19 scFv fragment is prone to oligomerization.

Due to the above remaining problems in the treatment of Alzheimer's disease and the diagnosis or therapy of tumors, it is an object of the present invention to provide alternative methods and compounds which can be used in the treatment of Alzheimer's disease and the diagnosis or therapy of tumors.

DETAILED DESCRIPTION OF THE INVENTION

The inventors found that specific muteins of proteins derived from Lipocalin 2 are attractive compounds due to their greater stability and even smaller size. The inventors identified a specific group of Lipocalin 2 muteins with mutations at specific positions which show high affinity and specificity for example for ED-B. Such Lcn2 muteins specifically recognize ED-B containing fibronectin on human cells with high sensitivity and thus show prospects as therapeutic reagents for the diagnosis and treatment of tumor diseases.

The inventors were also able to identify specific Lcn2 muteins with high affinity and specificity for the Aβ peptide.

Such Lcn2 muteins can even inhibit Aβ aggregation and thus show prospects, possibly after further improvement and modification, as therapeutic reagents to treat AD.

Furthermore, the present invention also describes new random libraries based on the human Lcn2 scaffold which permit the efficient generation of muteins, such as the muteins of the present invention, with high affinity and specificity for a given target in general. Examples for such libraries or sections thereof are shown in FIGS. 1 and 2.

In one aspect at least at 1, 2, 3, 4, 5, 6, 7, 8, 9, 10, 11, 12, 13, 14, 15, 16, 17, 18, 19, 20 nucleotide triplet(s) encoding for any of the sequence positions 36, 40, 41, 49, 52, 68, 70, 72, 73, 77, 79, 81, 96, 100, 103, 106, 125, 127, 132, and 134 of the linear polypeptide sequence of hLcn2 a random mutagenesis was carried out by allowing substitution at this positions by a subset of nucleotide triplets. A subset of nucleotide triples can refer to, but is not limited to (a) less than the 64 possible triplets encoded by the nucleotides NNN (if N=A, T, G, C that means 4×4×4=64 possible triplets), (b) less than the 32 possible triplets encoded by the nucleotides NNK or NNS, (c) less than the necessary triplets to encode all 20 natural proteinogenic amino acids. In another embodiment, nucleotide triplets coding for cystein are not used for substitution during the mutagenesis. That means that the mutagenesis does not lead to muteins carrying new cysteins which were not already included in the original not mutagenized sequenze. Thus, in this aspect it is specified how the nucleotide triplets look like which are to be introduced into the positions which are to be mutagenised as specified in this paragraph (see also Example 1 and FIG. 2).

Thus, in a first aspect the present invention is directed to a method of generating a mutein derived from human Lipocalin 2 (Lcn2; also known as human neutrophil gelatinase-associated lipocalin, hNGAL, or as siderocalin). The muteins obtained with this method can bind to a non-natural target with detectable affinity. The method comprises subjecting a nucleic acid molecule encoding for human Lipocalin 2 (Lcn2, hNGAL) to mutagenesis at a nucleotide triplet coding for at least one of any one of the sequence positions corresponding to the sequence positions 96, 100, and 106, of the linear polypeptide sequence of human Lipocalin 2, resulting in one or more mutein nucleic acid molecule(s).

In accordance with the above, the term "human Lipocalin 2" or "human neutrophil gelatinase-associated lipocalin (hNGAL)" includes structural homologues, already identified or yet to be isolated, from other species which have an amino acid sequence homology or sequence identity of more than about 60%. It is preferred that these human lipocalins described above comprise 1, 2, 3, 4, 5, 6, 7, 8, 9, 10, 11, 12, 13, 14, 15, 16, or 17 mutated amino acid residues at any of the sequence positions corresponding to the sequence positions 33, 36, 40, 41, 42, 43, 44, 46, 47, 48, 49, 50, 51, 52, 54, 55, 59, 65, 68, 70, 72, 73, 75, 77, 78, 79, 80, 81, 86, 87, 98, 96, 99, 100, 103, 106, 107, 110, 111, 125, 127, 132, 134, 136 and 138 of the linear polypeptide sequence of hNGAL. The term "homology" as used herein in its usual meaning and includes identical amino acids as well as amino acids which are regarded to be conservative substitutions (for example, exchange of a glutamate residue by a aspartate residue) at equivalent positions in the linear amino acid sequence of two proteins that are compared with each other. The term "sequence identity" or "identity" as used in the present invention means the percentage of pair-wise identical residues—following homology alignment of a sequence of a polypeptide of the present invention with a sequence in question—with respect to the number of residues in the longer of these two sequences.

The percentage of sequence homology or sequence identity is determined herein using the program BLASTP, version blastp 2.2.5 (Nov. 16, 2002; cf. Altschul, S. F. et al. (1997) *Nucl. Acids Res.* 25, 3389-3402). The percentage of homology is based on the alignment of the entire polypeptide sequences (matrix: BLOSUM 62: gap costs: 11.1; cutoff value set to $10^{-3}$) including the propeptide sequences, using the human Lipocalin 2 as reference in a pairwise comparison. It is calculated as the percentage of numbers of "positives" (homologous amino acids) indicated as result in the BLASTP program output divided by the total number of amino acids selected by the program for the alignment. It is noted in this connection that this total number of selected amino acids can differ from the length of the human Lipocalin 2.

In case a protein other that human Lipocalin 2 is used in the present invention, the definition of the mutated sequence positions given for human Lipocalin 2 can be assigned to the other lipocalin with the help of published sequence alignments or alignments methods which are available to the skilled artisan. A sequence alignment can, for example, be carried out as explained in WO 99/16873 (cf. FIG. 3 therein), using an published alignment such as the one in FIG. 1 of Redl, B. (2000) *Biochim. Biophys. Acta* 1482, 241-248. If the three-dimensional structure of the lipocalins is available structural superpositions can also be used for the determination of those sequence positions that are to be subjected to mutagenesis in the present invention. Other methods of structural analysis such as multidimensional nuclear magnetic resonance spectroscopy can also be employed for this purpose.

The homologue of human Lipocalin 2 can also be a mutein protein of human Lipocalin 2 itself, in which amino acid substitutions are introduced at positions other than the positions selected in the present invention. For example, such a mutein can be a protein in which positions at the solvent exposed surface of the 1-barrel are mutated compared to the wild type sequence of the human Lipocalin 2 in order to increase the solubility or the stability of the protein.

In general, the term "human Lipocalin 2" includes all proteins that have a sequence homology or sequence identity of more than 60%, 70% 80%, 85%, 90%, or 95% in relation to the human Lipocalin 2. It is preferred that these human lipocalins described above comprise 1, 2, 3, 4, 5, 6, 7, 8, 9, 10, 11, 12, 13, 14, 15, 16, or 17 mutated amino acid residues at any of the sequence positions corresponding to the sequence positions 33, 36, 40, 41, 42, 43, 44, 46, 47, 48, 49, 50, 51, 52, 54, 55, 59, 65, 68, 70, 72, 73, 75, 77, 78, 79, 80, 81, 86, 87, 98, 96, 99, 100, 103, 106, 107, 110, 111, 125, 127, 132, 134, 136 and 138 of the linear polypeptide sequence of hNGAL.

Thus, in a further aspect, the present invention provides a mutein derived from human Lipocalin 2 (i.e., human lipocalin mutein or a mutated human lipocalin, preferably a mutated mature hNGAL, wherein said mature hNGAL has the SWISS-PROT Data Bank Accession Number P80188, more preferably said mature hNGAL has the amino acid sequence shown in SEQ ID NO:44). This mutein includes at least one or two mutated amino acid residue at any of the sequence positions corresponding to the sequence positions 96, 100 and 106 of the linear polypeptide sequence of human Lcn2, and wherein the mutein binds a given non-natural target with detectable affinity.

As used herein, a "mutein," a "mutated" entity (whether protein or nucleic acid) or "mutant" refers to the exchange, deletion, or insertion of one or more nucleotides or amino acids, respectively, compared to the naturally occurring (wild-type) nucleic acid or protein "reference" scaffold. Preferably, the number of nucleotides or amino acids, respectively, that is exchanged, deleted or inserted is 1, 2, 3, 4, 5, 6, 7, 8, 9, 10, 11, 12, 13, 14, 15, 16, 17, 18, 19, 20 or more such as 25, 30, 35, 40, 45 or 50.

The term "human neutrophil gelatinase-associated lipocalin" or "hNGAL" or "lipocalin 2" or "Lcn2" as used herein to refer to the mature hNGAL with the SWISS-PROT Data Bank Accession Number P80188 (exemplified herein as SEQ ID NO:44).

In this context, it s noted that the invention is based on the surprising finding that subjecting human Lipocalin 2, rat $\alpha_2$-microglobulin-related protein (A2m) and mouse 24p3/uterocalin (24p3) to mutagenesis at one or more of these above-mentioned 3 sequence position provides for muteins that have a sufficiently affine binding to pre-defined target which can include, but is not limited to a peptide, a protein, a fragment or a domain of a protein, and a small organic molecule.

The given target may be any desired non-natural target/ligand. In one embodiment, the term "non-natural ligand" refers to a compound, which does not bind to native mature hNGAL under physiological conditions.

The term "organic molecule" or "small organic molecule" as used herein for the non-natural target denotes an organic molecule comprising at least two carbon atoms, but preferably not more than 7 or 12 rotatable carbon bonds, having a molecular weight in the range between 100 and 2000 Dalton, preferably between 100 and 1000 Dalton, and optionally including one or two metal atoms.

The term "peptide" as used herein for the non-natural target refers to a dipeptide or an oligopeptide with 2 to 45 amino acids. In one embodiment, the peptide has 2-40, 2-35, 2-30, 2-25, 2-20, 2-15 or 2-10 amino acid residues. The peptide may be a naturally occurring or synthetic peptide and may comprise—besides the 20 naturally occurring L-amino acids—D-amino acids, non-naturally occurring amino acids and amino acid analogs. In one embodiment, the peptide is an amyloid beta peptide (Abeta or Aβ). In another embodiment, the amyloid beta peptide is an Aβ40 peptide or an Aβ42 peptide.

In one embodiment, the small organic molecule is a compound showing the features of an immunological hapten.

In one embodiment, the non-natural target which is a protein is fibronection or a domain thereof, such as the EB-domain or a fragment of the EB-domain.

A human Lipocalin 2 mutein of the invention may comprise the wild type (natural) amino acid sequence outside the mutated amino acid sequence positions. On the other hand, the lipocalin muteins disclosed herein may also contain amino acid mutations outside the sequence positions subjected to mutagenesis as long as those mutations do not interfere with the binding activity and the folding of the mutein. Such mutations can be accomplished very easily on DNA level using established standard methods (Sambrook, J. et al. (1989) *Molecular Cloning: A Laboratory Manual*, 2nd Ed., Cold Spring Harbor Laboratory Press, Cold Spring Harbor, NY). Possible alterations of the amino acid sequence are insertions or deletions as well as amino acid substitutions. Such substitutions may be conservative, i.e. an amino acid residue is replaced with a chemically similar amino acid residue. Examples of conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan. One the other hand, it is also possible to introduce non-conservative alterations in the amino acid sequence. In addition, instead of replacing single amino acid residues, it is also possible to either insert or delete one or more continuous amino acids of the primary structure of human Lipocalin 2 as long as these deletions or insertion result in a stable folded/functional mutein.

As an overview, such modifications of the amino acid sequence include directed mutagenesis of single amino acid positions in order to simplify sub-cloning of the mutated lipocalin gene or its parts by incorporating cleavage sites for certain restriction enzymes. In addition, these mutations can also be incorporated to further improve the affinity of a lipocalin mutein for a given target. Furthermore, mutations can be introduced in order to modulate certain characteristics of the mutein such as to improve folding stability, serum stability, protein resistance or water solubility or to reduce aggregation tendency, if necessary. For example, naturally occurring cysteine residues may be mutated to other amino acids to prevent disulphide bridge formation. However, it is also possible to deliberately mutate other amino acid sequence position to cysteine in order to introduce new reactive groups, for example for the conjugation to other compounds, such as polyethylene glycol (PEG), hydroxyethyl starch (HES), biotin, peptides or proteins, or for the formation of non-naturally occurring disulphide linkages. Exemplary possibilities of such a mutation to introduce a cysteine residue into the amino acid sequence of a human Lipocalin 2 mutein include the introduction of a cysteine (Cys) residue at least at one of the sequence positions that correspond to sequence positions 14, 21, 60, 84, 88, 116, 141, 145, 143, 146 or 158 of the wild type sequence of hNGAL. The generated thiol moiety at the side of any of the amino acid positions 14, 21, 60, 84, 88, 116, 141, 145, 143, 146 and/or 158 may be used to PEGylate or HESylate the mutein, for example, in order to increase the serum half-life of a respective human Lipocalin 2 mutein.

In one embodiment, the mutein of the present invention includes mutated amino acid residues at least at any 2 or all 3 of the sequence positions corresponding to the sequence positions 96, 100 and 106 of the linear polypeptide sequence of human Lipocalin 2.

In a further embodiment of the invention, the mutein includes at least 1, 2, 3, 4, 5, 6, 7, 8, 9, 10, 11, 12, 13, 14, 15, 16, or 17 mutated amino acid residues at any of the sequence positions corresponding to the sequence positions 33, 36, 40, 41, 42, 43, 44, 46, 47, 48, 49, 50, 51, 52, 54, 55, 59, 65, 68, 70, 72, 73, 75, 77, 78, 79, 80, 81, 86, 87, 98, 96, 99, 100, 103, 106, 107, 110, 111, 125, 127, 132, 134, 136 and 138 of the linear polypeptide sequence of hNGAL. In a further embodiment, the mutein includes at least 2, 3, 4, 5, 6, 7, 8, 9, 10, 11, 12, 13, 14, 15, 16, 17 mutated amino acid residues at any one of the sequence positions 33, 36, 40, 41, 42, 43, 44, 46, 47, 48, 49, 50, 51, 52, 54, 55, 59, 65, 68, 70, 72, 73, 75, 77, 78, 79, 80, 81, 86, 87, 98, 96, 99, 100, 103, 106, 107, 110, 111, 125, 127, 132, 134, 136 and 138 of the linear polypeptide sequence of hNGAL. In still a further embodiment, the mutein includes 18, 19 or 20 mutated amino acid residues at any one of the sequence positions 33, 36, 40, 41, 42, 43, 44, 46, 47, 48, 49, 50, 51, 52, 54, 55, 59, 65, 68, 70, 72, 73, 75, 77, 78, 79, 80, 81, 86, 87, 98, 96, 99, 100, 103, 106, 107, 110, 111, 125, 127, 132, 134, 136 and 138 of the linear polypeptide sequence of human Lipocalin 2.

In one embodiment of the present invention, the mutein includes mutated amino acid residues at at least any 10, 14, 15, 20, 22, 24, 26, 28, 29, 30, 31, 32, 33, 35 or all 45 of the above-listed sequence positions.

A mutein of the invention which binds to an amyloid beta peptide, such as Aβ40 peptide or an Aβ42 peptide, can comprise with respect to the mature human Lipocalin 2 wild type amino acid sequence illustrated in FIG. 17 (Lcn2) at least 2, 3, 4, 5, 6, 7, 8, 9, 10, 11, or 12 amino acid replacements which include, but are not limited to Leu36→Val or Cys; Ala40→Tyr or Lys or Val; Ile41→Thr or Ser or Leu; Gln49→Leu or Trp: Leu70→Gly; Arg72→Gly or Asp; Lys73→Leu or Thr or Asp; Asp77→Asn or His or Leu: Trp79→Lys; Asn96→Ile or Arg; Tyr100→Gln or Arg or Glu; Leu103→Met or Arg or Gly; Tyr106→Tyr or Ala or Trp; Lys125→Thr or Val or Glu; Ser127→Gly or Gln or Ala; Tyr132→Met or Ser or Thr; and Lys134→Asn. It was found that such muteins can diminish Aβ aggregation in vitro or in vivo. It is preferred that the mutein described herein binds to and inhibits aggregation of Aβ, preferably Aβ40, more preferably under assay conditions as specified in Example 11 (preferably including the ratio 1:10 mutein: Aβ40). The present invention also relates to muteins as described above having a comparable biological function when compared with mutein US7. "Comparable biological function" means that these muteins are able to bind to and inhibit Aβ, preferably Aβ40, with a deviation of the aggregation inhibiting activity in respect to US7 of not more than about 40%, 30%, 20%, 15%, 10%, 5%, 2.5%, 2% or 1%, for example under conditions which equate to or are identical with those set out in Example 11 (preferably including the ratio 1:10 mutein: Aβ40). The present invention also relates to the muteins described herein for use in the treatment or prevention of neurodegenerative diseases such as Alzheimer's disease.

In one embodiment, a mutein of the invention which binds to an amyloid beta peptide, such as Aβ40 peptide or an Aβ42 peptide comprises the following amino acid replacements Leu36→Val; Ala40→Tyr; Ile41→Thr: Gln49→Leu: Leu70→Gly; Lys73→Leu; Asp77→Asn; Trp79→Lys; Asn96→Ile; Tyr100→Gln; Leu103→Met; Lys125→Thr; Ser127→Gly; Tyr132→Met; and Lys134→Asn. An example of a mutein including such amino acid replacements is S1-A4 illustrated in FIG. 17 (SEQ ID NO: 39).

In a further embodiment, a mutein of the invention which binds to an amyloid beta peptide, such as Aβ40 peptide or an Aβ42 peptide comprises the following amino acid replacements Leu36→Val; Ala40→Lys; Ile41→Ser; Gln49→Trp; Leu70→Gly; Arg72→Gly; Lys73→Thr; Asp77→His; Trp79→Lys; Asn96→Arg; Tyr100→Arg; Leu103→Arg; Tyr106→Ala; Lys125→Val; Ser127→Gln; Tyr132→Ser; and Lys134→Asn. An example of a mutein including such amino acid replacements is US-7 illustrated in FIG. 17 (SEQ ID NO: 41).

The invention also envisages a mutated mature hNGAL lipocalin (as deposited in SWISS-PROT Data Bank under Accession Number P80188, preferably having the amino acid sequence shown in SEQ ID NO:40) comprising at a position corresponding to a position 36, 40, 41, 49, 70, 72, 73, 77, 79, 96, 100, 103, 106, 125, 127, 132, 134 of the linear polypeptide sequence of wild type hNGAL one or more mutated amino acids as described herein.

In another embodiment, a mutein of the invention which binds to an amyloid beta peptide, such as Aβ40 peptide or an Aβ42 peptide comprises the following amino acid replacements Leu36→Cys; Ala40→Val; Ile41→Leu; Gln49→Leu; Leu70→Gly; Arg72→Asp; Lys73→Asp; Asp77→Leu; Trp79→Lys; Asn96→Arg; Tyr100→Glu; Leu103→Gly; Tyr106→Trp; Lys125→Glu: Ser127→Ala: Tyr132→Thr; and Lys134→Asn. An example of a mutein including such amino acid replacements is H1-G1 illustrated in FIG. 17 (SEQ ID NO: 43).

In another embodiment, a mutein of the invention which binds to an amyloid beta peptide, such as Aβ40 peptide or an Aβ42 peptide comprises the following amino acid replacements Leu36→Ala; Ala40→Val; Ile41→Leu; Gln49→Leu: Leu70→Gly; Arg72→Asp; Lys73→Asp; Asp77→Leu; Trp79→Lys; Asn96→Arg: Tyr100→Glu; Leu103→Gly; Tyr106→Trp; Lys125→Glu: Ser127→Ala; Tyr132→Thr; and Lys134→Asn. An example of a mutein including such amino acid replacements is H1GA illustrated SEQ ID NO: 50.

It is preferred that the mutein described herein above binds to and inhibits aggregation of AP, preferably Aβ40, more preferably under assay conditions as specified in Example 23 (preferably in a ratio of 10:2 Aβ40: H1GA). The present invention also relates to muteins as described above having a comparable biological function when compared with mutein H1GA. "Comparable biological function" means that these muteins are able to bind to and inhibit Aβ, preferably Aβ40 with a deviation of the aggregation inhibiting activity in respect to H1GA of not more than about 40%, 30%, 20%, 15%, 10%, 5%, 2.5%, 2% or 1%, for example under conditions which equate to or are identical with those set out in Example 23 (preferably in a ratio of 10:2 Aβ40: H1GA). The present invention also relates to the muteins described herein for use in the treatment or prevention of neurodegenerative diseases such as Alzheimer's disease.

In another embodiment, a mutein of the invention which binds to an amyloid beta peptide, such as Aβ40 peptide or an Aβ42 peptide comprises the following amino acid replacements Leu36→Val; Ala40→Val; Ile41→Leu; Gln49→Leu: Leu70→Gly; Arg72→Asp; Lys73→Asp; Asp77→Leu; Trp79→Lys; Asn96→Arg: Tyr100→Glu; Leu103→Gly: Tyr106→Trp; Lys125→Glu: Ser127→Ala; Tyr132→Thr; and Lys134→Asn. An example of a mutein including such amino acid replacements is H1GV illustrated SEQ ID NO: 52.

It is preferred that the mutein described herein above binds to Aβ40 under assay conditions as specified in Example 21. The present invention also relates to muteins as described above having a comparable biological function when compared with mutein H1GV. "Comparable biological function" means that these muteins are able to bind to Aβ, preferably Aβ40 with a deviation of the aggregation inhibiting activity in respect to H1GV of not more than about 40%, 30%, 20%, 15%, 10%, 5%, 2.5%, 2% or 1%, for example under conditions which equate to or are identical with those set out in Example 21. The present invention also relates to the muteins described herein for use in the treatment or prevention of neurodegenerative diseases such as Alzheimer's disease.

In a further embodiment, a mutein of the invention which bind to extra-domain B or a fragment thereof comprises the following amino acid replacements Leu36→Lys; Ala40→His: Ile41→Asp: Gln49→Arg; Tyr52→Gln; Ser68→Asn; Leu70→Arg; Arg72→Val; Lys73→His; Asp77→Asn; Trp79→Arg; Arg81→Trp; Tyr100→Trp: Tyr106→Trp; Lys125→Arg; Ser127→Tyr; Tyr132→Leu; Lys1134→Glu and Ser146→Asn. An example of a mutein including such amino acid replacements is N7A illustrated in FIG. 17 (SEQ ID NO: 20).

In another embodiment, a mutein of the invention which binds to extra-domain B or a fragment thereof comprises the following amino acid replacements Leu36→Arg; Ala40→Met; Ile41→Arg; Gln49→Ala; Tyr52→Val; Ser68→Lys; Leu70→Met; Arg72→Gln; Lys73→Arg; Asp77→Lys; Trp79→Met; Arg81→Asn; Asn96→Ala; Tyr100→Pro; Leu103→Pro; Tyr106→Thr; Lys125→His; Ser127→Phe; and Lys134→His. An example of a mutein including such amino acid replacements is N9B illustrated in FIG. 17 (SEQ ID NO: 24).

In another embodiment, a mutein of the invention which binds to extra-domain B or a fragment thereof comprises the following amino acid replacements Leu36→Ala; Ala40→Thr; Ile41→Trp; Gln49→Tyr; Tyr52→Gln; Ser68→Asn; Arg72→Met; Lys73→Ser; Asp77→Arg; Trp79→Met; Arg81→His; Asn96→Ser: Tyr100→Trp; Tyr106→Trp; Lys125→Arg; Ser127→Tyr: Tyr132→Phe; and Lys134→Gly. An example of a mutein including such amino acid replacements is N10D illustrated in FIG. 17 (SEQ ID NO: 26).

In a further embodiment, a mutein of the invention which bind to extra-domain B or a fragment thereof comprises the following amino acid replacements Leu36→Glu; Ala40→Ser; Ile41→Leu; Gln49→Arg; Leu70→Arg; Lys73→Ser; Asp77→His; Trp79→Leu; Asn96→Leu; Tyr100→Lys; Leu103→His: Tyr106→Phe: Lys125→Thr; Ser127→Ala; and Lys134→Phe. An example of a mutein including such amino acid replacements is N7E illustrated in FIG. 17 (SEQ ID NO: 22).

The above muteins described with reference to FIG. 17 can include further amino acid replacements. The muteins can further comprise amino acid replacements which can include, but are not limited to Gln28→His or Cys87→Ser. Other possible amino acid replacements include, but are not limited to Tyr52→Gln or Val; Ser68→Lys or Asn; or Arg81→Trp or Asn or His.

The lipocalin muteins of the invention are able to bind the desired non-natural target with detectable affinity, i.e. with a dissociation constant ($K_D$) of at least 200 nM. In another embodiment, the mutein binds the given non-natural target with a $K_D$ of 1 µM or less, or 100 µM or less, or 1 µM or less, or 500 nM, or 200 nM or less, or 100, nM or less, or 50 nM or less, or 10 nM or less, or 1 nM or less. In another embodiment, lipocalin muteins bind the desired target with a dissociation constant for a given target of at least 100, 20, 1 nM or even less. The binding affinity of a mutein to the desired target can be measured by a multitude of methods such as fluorescence titration, competition ELISA or surface plasmon resonance (Biacore).

It is readily apparent to the skilled person that complex formation with the target is dependent on many factors such as concentration of the binding partners, the presence of competitors, ionic strength of the buffer system etc. Selection and enrichment is generally performed under conditions allowing the isolation of lipocalin muteins having, in complex with the desired target, a dissociation constant as indicated above. However, the washing and elution steps can be carried out under varying stringency. A selection with respect to the kinetic characteristics is possible as well. For example, the selection can be performed under conditions, which favor complex formation of the target with muteins that show a slow dissociation from the target, or in other words a low $k_{off}$ rate. Alternatively, selection can be performed under conditions, which favor fast formation of the complex between the mutein and the target, or in other words a high $k_{on}$ rate.

A mutein of the invention typically exists as monomeric protein. However, it is also possible that an inventive lipocalin mutein is able to spontaneously dimerise or oligomerise. Although the use of lipocalin muteins that form stable monomers may be preferred for some applications, e.g. because of faster diffusion and better tissue penetration, the use of lipocalin muteins that form stable homodimers or multimers may be advantageous in other instances, since such multimers can provide for a (further) increased affinity and/or avidity to a given target. Furthermore, oligomeric forms of the lipocalin mutein may have slower dissociation rates or prolonged serum half-life.

It is also noted that the complex formation between the respective mutein and its ligand is influenced by many different factors such as the concentrations of the respective binding partners, the presence of competitors, pH and the ionic strength of the buffer system used, and the experimental method used for determination of the dissociation constant $K_D$ (for example fluorescence titration, competition ELISA or surface plasmon resonance, just to name a few) or even the mathematical algorithm which is used for evaluation of the experimental data.

Therefore, it is also clear to the skilled person that the $K_D$ values (dissociation constant of the complex formed between the respective mutein and its target/ligand) may vary within a certain experimental range, depending on the method and experimental setup that is used for determining the affinity of a particular lipocalin mutein for a given ligand. This means, there may be a slight deviation in the measured $K_D$ values or a tolerance range depending, for example, on whether the $K_D$ value was determined by surface plasmon resonance (Biacore) or by competition ELISA.

In one embodiment, the muteins disclosed herein can be linked, either N- or C-terminal to an affinity tag such as pentahistidine tag (SEQ ID NO: 53), a hexahistidine tag (SEQ ID NO: 54) or a Strep-Tag®. Thus, the present application encompasses also all explicitly and generic described muteins equipped with such tags.

The term "fragment" as used in the present invention in connection with the feature lipocalin mutein fragment relates to proteins or peptides derived from full-length mature Lcn2 that are N-terminally and/or C-terminally shortened, i.e. lacking at least one of the N-terminal and/or C-terminal amino acids. Such fragments comprise preferably at least 10, more preferably 20, most preferably 30 or more consecutive amino acids of the primary sequence of mature Lcn2 and are usually detectable in an immunoassay of mature Lcn2.

Also included in the scope of the present invention are the above muteins, which have been altered with respect to their immunogenicity.

Cytotoxic T-cells recognize peptide antigens on the cell surface of an antigen-presenting cell in association with a class I major histocompatibility complex (MHC) molecule. The ability of the peptides to bind to MHC molecules is allele specific and correlates with their immunogenicity. In order to reduce immunogenicity of a given protein, the ability to predict which peptides in a protein have the potential to bind to a given MHC molecule is of great value. Approaches that employ a computational threading approach to identify potential T-cell epitopes have been previously described to predict the binding of a given peptide sequence to MHC class I molecules (Altuvia et al. (1995) *J. Mol. Biol.* 249: 244-250).

Such an approach may also be utilized to identify potential T-cell epitopes in the muteins of the invention and to make depending on its intended use a selection of a specific mutein on the basis of its predicted immunogenicity. It may be furthermore possible to subject peptide regions which have been predicted to contain T-cell epitopes to additional mutagenesis to reduce or eliminate these T-cell epitopes and thus minimize immunogenicity. The removal of amphipatic epitopes from genetically engineered antibodies has been described (Mateo et al. (2000) *Hybridoma* 19(6):463-471) and may be adapted to the muteins of the present invention.

The muteins thus obtained may possess a minimized immunogenicity, which is desirable for their use in therapeutic and diagnostic applications, such as those described below.

For some applications, it is also useful to employ the muteins of the invention in a conjugated form. Accordingly, the invention is also directed to lipocalin muteins which are conjugated to a compound which can include, but is not limited to organic molecules, an enzyme label, a colored label, a cytostatic agent, a toxin, a label that can be photoactivated and which is suitable for use in photodynamic therapy, a fluorescent label, a radioactive label, a chromogenic label, a luminescent label, metal complexes, metal, such as colloidal gold, haptens, digoxigenin, biotin, a chemotherapeutic metal, or a chemotherapeutic metal, to name only a few evocative examples. The mutein may also be conjugated to an organic drug molecule. The conjugation can be carried out using any conventional coupling method known in the art.

In general, it is possible to label a Lcn2 mutein described herein with any appropriate chemical substance or enzyme, which directly or indirectly generates a detectable compound or signal in a chemical, physical, optical, or enzymatic reaction. An example for a physical reaction and at the same time optical reaction/marker is the emission of fluorescence upon irradiation. Alkaline phosphatase, horseradish peroxidase or β-galactosidase are examples of enzyme labels (and at the same time optical labels) which catalyze the formation of chromogenic reaction products. In general, all labels commonly used for antibodies (except those exclusively used with the sugar moiety in the Fc part of immunoglobulins) can also be used for conjugation to the muteins of the present invention. The muteins of the invention may also be conjugated with any suitable therapeutically active agent, e.g., for the targeted delivery of such agents to a given cell, tissue or organ or for the selective targeting of cells, e.g., of tumor cells without affecting the surrounding normal cells. Examples of such therapeutically active agents include radionuclides, toxins, small organic molecules, and therapeutic peptides (such as peptides acting as agonists/antagonists of a cell surface receptor or peptides competing for a protein binding site on a given cellular target). Examples of suitable toxins include, but are not limited to pertussis-toxin, diphtheria toxin, ricin, saporin, pseudomonas exotoxin, calicheamicin or a derivative thereof, a taxoid, a maytansinoid, a tubulysin or a dolastatin analogue. The dolastatin analogue may be auristatin E, monomethylauristatin E, auristatin PYE and auristatin PHE. Examples of cytostatic agent include, but are not limited to Cisplatin, Carboplatin. Oxaliplatin, 5-Fluorouracil. Taxotere (Docetaxel), Paclitaxel, Anthracycline (Doxorubicin), Methotrexate, Vinblastin, Vincristine, Vindesine, Vinorelbine, Dacarbazine, Cyclophosphamide, Etoposide, Adriamycine, Camptotecine, Combretatastin A-4 related compounds, sulfonamides, oxadiazolines, benzo[b]thiophenessynthetic spiroketal pyrans, monotetrahydrofuran compounds, curacin and curacin derivatives, methoxyestradiol derivatives and Leucovorin. The lipocalin muteins of the invention may also be conjugated with therapeutically active nucleic acids such as antisense nucleic acid molecules, small interfering RNAs, micro RNAs or ribozymes. Such conjugates can be produced by methods well known in the art.

In one embodiment, the muteins of the invention may also be coupled to a targeting moiety that targets a specific body region in order to deliver the inventive muteins to a desired region or area within the body. One example wherein such modification may be desirable is the crossing of the blood-brain-barrier. In order to cross the blood-brain barrier, the muteins of the invention may be coupled to moieties that facilitate the active transport across this barrier (see Gaillard P J, et al. (2005) *International Congress Series.* 1277, 185-198 or Gaillard P J, et al. (2005) *Expert Opin Drug Deliv.* 2(2), 299-309). Such compounds are for example available under the trade name 2B-Trans™ (to-BBB technologies BV, Leiden. NL). Other exemplary targeting molecules to which the muteins of the present invention may be coupled include antibodies, antibody fragments or lipocalin muteins with affinity for a desired target molecule. The target molecule of the targeting moieties may, for example, be a cell-surface antigen. Cell-surface antigens may be specific for a cell or tissue type, such as, for example, cancer cells. Illustrative examples of such cell surface proteins are HER-2 or proteoglycans such as NEU-2.

As indicated above, a mutein of the invention may in some embodiments be conjugated to a compound that extends the serum half-life of the mutein (in this regard see also PCT publication WO 2006/56464 where such conjugation strategies are described with references to muteins of human neutrophil gelatinase-associated lipocalin with binding affinity for CTLA-4). The compound that extends the serum half-life may be a polyalkylene glycol molecule, such as polyethylene (PEG) or an activated derivative thereof; hydroxyethyl starch, fatty acid molecules, such as palmitic acid (Vajo & Duckworth (2000) *Pharmacol. Rev.* 52, 1-9), an Fc part of an immunoglobulin, a CH3 domain of an immunoglobulin, a CH4 domain of an immunoglobulin, albumin or a fragment thereof, an albumin binding peptide, or an albumin binding protein, transferrin to name only a few. The albumin binding protein may be a bacterial albumin binding protein, an antibody, an antibody fragment including domain antibodies (see U.S. Pat. No. 6,696,245, for example), or a lipocalin mutein with binding activity for albumin. Accordingly, suitable conjugation compounds for extending the half-life of a lipocalin mutein of the invention include albumin (Osbom et al. (2002) *J. Pharmacol. Exp. Ther.* 303, 540-548), or an albumin binding protein, for example, a bacterial albumin binding domain, such as the one of streptococcal protein G (Konig, T. and Skerra. A. (1998) *J. Immunol. Methods* 218, 73-83). Other examples of albumin binding peptides that can be used as conjugation partner are, for instance, those having a Cys-$Xaa_1$-$Xaa_2$-$Xaa_3$-$Xaa_4$-Cys consensus sequence (SEQ ID NO: 55), wherein $Xaa_1$ is Asp, Asn, Ser, Thr, or Trp; $Xaa_2$ is Asn, Gin, His, Ile, Leu, or Lys; $Xaa_3$ is Ala, Asp, Phe, Trp, or Tyr; and $Xaa_4$ is Asp, Gly, Leu, Phe, Ser, or Thr as described in US patent application 2003/0069395 or Dennis et al. (Dennis et al. (2002) *J. Biol. Chem.* 277, 35035-35043).

In other embodiments, albumin itself or a biological active fragment of albumin can be used as compound of a lipocalin mutein of the invention that extends the serum half-life of the mutein. The term "albumin" comprises all mammal albumins such as human serum albumin or bovine serum albumin or rat albumin. The albumin or fragment thereof can be recombinantly produced as described in U.S. Pat. No. 5,728,553 or European patent applications EP 0 330 451 and EP 0 361 991. Recombinant human albumin (Recombumin®) for use as a protein stabilizer is for example available from Novozymes Delta Ltd. (Nottingham, UK).

If the albumin-binding protein is an antibody fragment it may be a domain antibody. Domain Antibodies (dAbs) are engineered to allow precise control over biophysical properties and in vivo half-life to create the optimal safety and efficacy product profile. Domain Antibodies are for example commercially available from Domantis Ltd. (Cambridge, UK and MA, USA).

Using transferrin as a moiety to extend the serum half-life of the muteins of the invention, the muteins can be genetically fused to the N or C terminus, or both, of non-glycosylated transferrin. Non-glycosylated transferrin has a half-life of 14-17 days, and a transferrin fusion protein will similarly have an extended half-life. The transferrin carrier also provides high bioavailability, biodistribution and circulating stability. This technology is commercially available from BioRexis (BioRexis Pharmaceutical Corporation, PA, USA). Recombinant human transferrin (DeltaFerrin™) for use as a protein stabilizer is also commercially available from Novozymes Delta Ltd. (Nottingham, UK).

If an Fc part of an immunoglobulin is used for the purpose to prolong the serum half-life of the muteins of the invention, the SynFusion™ technology, commercially available from Syntonix Pharmaceuticals, Inc (MA, USA), may be used. The use of this Fc-fusion technology allows the creation of longer-acting biopharmaceuticals and may for example consist of two copies of the mutein linked to the Fc region of an antibody to improve pharmacokinetics, solubility, and production efficiency.

Yet another alternative to prolong the half-life of a mutein of the invention is to fuse the N- or C-terminus of a mutein of the invention to long, unstructured, flexible glycine-rich sequences (for example poly-glycine with about 20 to 80 consecutive glycine residues). This approach disclosed in WO2007/038619, for example, has also been term "rPEG" (recombinant PEG).

If polyalkylene glycol is used as compound that extends the half-life of the mutein, the polyalkylene glycol can be substituted or unsubstituted. It can also be an activated polyalkylene derivative. Examples of suitable compounds are polyethylene glycol (PEG) molecules as described in WO 99/64016, in U.S. Pat. No. 6,177,074 or in U.S. Pat. No. 6,403,564 in relation to interferon, or as described for other proteins such as PEG-modified asparaginase, PEG-adenosine deaminase (PEG-ADA) or PEG-superoxide dismutase (see for example, Fuertges et al. (1990) The Clinical Efficacy of Poly(Ethylene Glycol)-Modified Proteins *J. Control. Release* 11, 139-148). The molecular weight of such a polymer, preferrably polyethylene glycol, may range from about 300 to about 70.000 Dalton, including, for example, polyethylene glycol with a molecular weight of about 10.000, of about 20.000, of about 30.000 or of about 40.000 Dalton. Moreover, as e.g. described in U.S. Pat. No. 6,500, 930 or 6,620,413, carbohydrate oligo- and polymers such as starch or hydroxyethyl starch (HES) can be conjugated to a mutein of the invention for the purpose of serum half-life extension.

In another embodiment, in order to provide suitable amino acid side chains for conjugating one of the above compounds to the muteins of the invention artificial amino acids may be introduced by mutagenesis. Generally, such artificial amino acids are designed to be more reactive and thus to facilitate the conjugation to the desired moiety. One example of such an artificial amino acid that may be introduced via an artificial tRNA is para-acetyl-phenylalanine.

For several applications of the muteins disclosed herein it may be advantageous to use them in the form of fusion proteins. In some embodiments, the inventive mutein is fused at its N-terminus and/or it's C-terminus to a protein, a protein domain or a peptide such as a signal sequence and/or an affinity tag.

For pharmaceutical applications a mutein of the invention may be fused to a fusion partner that extends the in vivo serum half-life of the mutein (see again PCT publication WO 2006/56464 where suitable fusion partner are described with references to muteins of human neutrophile gelatinase-associated lipocalin with binding affinity for CTLA-4). Similar to the conjugated compounds described above, the fusion partner may be an Fc part of an immunoglobulin, a CH3 domain of an immunoglobulin, a CH4 domain of an immungloubulin, albumin, an albumin binding peptide or an albumin binding protein, to name only a few. Again, the albumin binding protein may be a bacterial albumin binding protein or a lipocalin mutein with binding activity for albumin. Accordingly, suitable fusion partners for extending the half-life of a lipocalin mutein of the invention include albumin (Osbom, B. L. et al. (2002) supra *J. Pharmacol. Exp. Ther.* 303, 540-548), or an albumin binding protein, for example, a bacterial albumin binding domain, such as the one of streptococcal protein G (König, T. and Skerra, A. (1998) supra *J. Immunol. Methods* 218, 73-83). The albumin binding peptides described in Dennis et al, supra (2002) or US patent application 2003/0069395 having a Cys-$Xaa_1$-$Xaa_2$-$Xaa_3$-$Xaa_4$-Cys consensus sequence (SEQ ID NO: 55), wherein $Xaa_1$ is Asp, Asn, Ser, Thr, or Trp; $Xaa_2$ is Asn, Gin, His, Ile, Leu, or Lys; $Xaa_3$ is Ala, Asp, Phe, Trp, or Tyr; and $Xaa_4$ is Asp, Gly, Leu, Phe, Ser, or Thr can also be used as fusion partner. It is also possible to use albumin itself or a biological active fragment of albumin as fusion partner of a lipocalin mutein of the invention. The term "albumin" comprises all mammal albumins such as human serum albumin or bovine serum albumin or rat serum albumin. The recombinant production of albumin or fragments thereof is well known in the art and for example described in U.S. Pat. No. 5,728,553, European patent application EP 0 330 451 or EP 0 361 991.

The fusion partner may confer new characteristics to the inventive lipocalin mutein such as enzymatic activity or binding affinity for other molecules. Examples of suitable fusion proteins are alkaline phosphatase, horseradish peroxidase, gluthation-S-transferase, the albumin-binding domain of protein G, protein A, antibody fragments, oligomerization domains, lipocalin muteins of same or different binding specificity (which results in the formation of "duocalins", cf. Schlehuber, S., and Skerra, A. (2001), Duocalins, engineered ligand-binding proteins with dual specificity derived from the lipocalin fold (*Biol. Chem.* 382, 1335-1342), or toxins.

In particular, it may be possible to fuse a lipocalin mutein of the invention with a separate enzyme active site such that both "components" of the resulting fusion protein together act on a given therapeutic target. The binding domain of the lipocalin mutein attaches to the disease-causing target, allowing the enzyme domain to abolish the biological function of the target.

Affinity tags such as the Strep-Tag® or Strep-Tag® 11 (Schmidt, T. G. M. et al. (1996) J. Mol. Biol. 255, 753-766), the myc-tag, the FLAG-tag, the $His_6$-tag (SEQ ID NO: 54) or the HA-tag or proteins such as glutathione-S-transferase also allow easy detection and/or purification of recombinant proteins are further examples of preferred fusion partners. Finally, proteins with chromogenic or fluorescent properties such as the green fluorescent protein (GFP) or the yellow fluorescent protein (YFP) are suitable fusion partners for a lipocalin mutein of the invention as well.

The term "fusion protein" as used herein also comprises lipocalin muteins according to the invention containing a signal sequence. Signal sequences at the N-terminus of a polypeptide direct this polypeptide to a specific cellular compartment, for example the periplasm of E. coli or the endoplasmatic reticulum of eukaryotic cells. A large number of signal sequences is known in the art. A preferred signal sequence for secretion a polypeptide into the periplasm of E. coli is the OmpA-signal sequence.

The present invention also relates to nucleic acid molecules (DNA and RNA) comprising nucleotide sequences coding for muteins as described herein. Since the degeneracy of the genetic code permits substitutions of certain codons by other codons specifying the same amino acid, the invention is not limited to a specific nucleic acid molecule encoding a mutein of the invention but includes all nucleic acid molecules comprising nucleotide sequences encoding a functional mutein.

Therefore, the present invention also includes a nucleic acid sequence encoding a mutein according to the invention including a mutation at least at one codon of any of the amino acid sequence positions 96, 100 and 106 of the linear polypeptide sequence of Lcn2.

The invention as disclosed herein also includes nucleic acid molecules encoding Lcn2 muteins, which comprise additional mutations outside the indicated sequence positions of experimental mutagenesis. Such mutations are often tolerated or can even prove to be advantageous, for example if they contribute to an improved folding efficiency, serum stability, thermal stability or ligand binding affinity of the mutein.

A nucleic acid molecule disclosed in this application may be "operably linked" to a regulatory sequence (or regulatory sequences) to allow expression of this nucleic acid molecule.

A nucleic acid molecule, such as DNA, is referred to as "capable of expressing a nucleic acid molecule" or capable "to allow expression of a nucleotide sequence" if it comprises sequence elements which contain information regarding to transcriptional and/or translational regulation, and such sequences are "operably linked" to the nucleotide sequence encoding the polypeptide. An operable linkage is a linkage in which the regulatory sequence elements and the sequence to be expressed are connected in a way that enables gene expression. The precise nature of the regulatory regions necessary for gene expression may vary among species, but in general these regions comprise a promoter which, in prokaryotes, contains both the promoter per se, i.e. DNA elements directing the initiation of transcription, as well as DNA elements which, when transcribed into RNA, will signal the initiation of translation. Such promoter regions normally include 5' non-coding sequences involved in initiation of transcription and translation, such as the −35/−10 boxes and the Shine-Dalgarno element in prokaryotes or the TATA box, CAAT sequences, and 5'-capping elements in eukaryotes. These regions can also include enhancer or repressor elements as well as translated signal and leader sequences for targeting the native polypeptide to a specific compartment of a host cell.

In addition, the 3' non-coding sequences may contain regulatory elements involved in transcriptional termination, polyadenylation or the like. If, however, these termination sequences are not satisfactory functional in a particular host cell, then they may be substituted with signals functional in that cell.

Therefore, a nucleic acid molecule of the invention can include a regulatory sequence, preferably a promoter sequence. In another preferred embodiment, a nucleic acid molecule of the invention comprises a promoter sequence and a transcriptional termination sequence. Suitable prokaryotic promoters are, for example, the tet promoter, the lacUV5 promoter or the T7 promoter. Examples of promoters useful for expression in eukaryotic cells are the SV40 promoter or the CMV promoter.

The nucleic acid molecules of the invention can also be part of a vector or any other kind of cloning vehicle, such as a plasmid, a phagemid, a phage, a baculovirus, a cosmid or an artificial chromosome.

In one embodiment, the nucleic acid molecule is comprised in a phasmid. A phasmid vector denotes a vector encoding the intergenic region of a temperent phage, such as M13 or f1, or a functional part thereof fused to the cDNA of interest. After superinfection of the bacterial host cells with such an phagemid vector and an appropriate helper phage (e.g. M13K07, VCS-M13 or R408) intact phage particles are produced, thereby enabling physical coupling of the encoded heterologous cDNA to its corresponding polypeptide displayed on the phage surface (reviewed, e.g., in Kay, B. K. et al. (1996) *Phage Display of Peptides and Proteins—A Laboratory Manual*, 1st Ed., Academic Press, New York NY; Lowman, H. B. (1997) *Annu. Rev. Biophys. Biomol. Struct.* 26, 401-424, or Rodi. D. J., and Makowski, L. (1999) *Curr. Opin. Biotechnol.* 10, 87-93).

Such cloning vehicles can include, aside from the regulatory sequences described above and a nucleic acid sequence encoding a lipocalin mutein of the invention, replication and control sequences derived from a species compatible with the host cell that is used for expression as well as selection markers conferring a selectable phenotype on transformed or transfected cells. Large numbers of suitable cloning vectors are known in the art, and are commercially available.

The DNA molecule encoding lipocalin muteins of the invention, and in particular a cloning vector containing the coding sequence of such a lipocalin mutein can be transformed into a host cell capable of expressing the gene. Transformation can be performed using standard techniques (Sambrook, J. et al. (1989), supra).

Thus, the invention is also directed to a host cell containing a nucleic acid molecule as disclosed herein.

The transformed host cells are cultured under conditions suitable for expression of the nucleotide sequence encoding a fusion protein of the invention. Suitable host cells can be prokaryotic, such as *Escherichia coli* (*E. coli*) or *Bacillus subtilis*, or eukaryotic, such as *Saccharomyces cerevisiae, Pichia pastoris*, SF9 or High5 insect cells, immortalized mammalian cell lines (e.g. HeLa cells or CHO cells) or primary mammalian cells.

The invention also relates to a method for the production of a mutein of the invention, wherein the mutein, a fragment of the mutein or a fusion protein of the mutein and another polypeptide is produced starting from the nucleic acid coding for the mutein by means of genetic engineering methods. The method can be carried out in vivo, the mutein can for example be produced in a bacterial or eucaryotic host organism and then isolated from this host organism or its culture. It is also possible to produce a protein in vitro, for example by use of an in vitro translation system.

When producing the mutein in vivo a nucleic acid encoding a mutein of the invention is introduced into a suitable bacterial or eukaryotic host organism by means of recombinant DNA technology (as already outlined above). For this purpose, the host cell is first transformed with a cloning vector comprising a nucleic acid molecule encoding a mutein of the invention using established standard methods (Sambrook, J. et al. (1989), supra). The host cell is then cultured under conditions, which allow expression of the heterologous DNA and thus the synthesis of the corresponding polypeptide. Subsequently, the polypeptide is recovered either from the cell or from the cultivation medium.

In one aspect, the present invention relates to a method for the generation of a mutein of the invention, comprising:
(a) subjecting a nucleic acid molecule encoding a human Lipocalin 2 to mutagenesis at a nucleotide triplet coding for at least one of any one of the sequence positions corresponding to the sequence positions 96, 100, and 106 of the linear polypeptide sequence of Lcn2, resulting in one or more mutein nucleic acid molecule(s).

The method can further comprise:
(b) expressing the one more mutein nucleic acid molecule(s) obtained in (a) in a suitable expression system, and
(c) enriching the one or more mutein(s) having a detectable binding affinity for a given target by means of selection and/or isolation.

The term "mutagenesis" as used herein means that the experimental conditions are chosen such that the amino acid naturally occurring at a given sequence position of Lcn2 (hNGAL; Swiss-Prot data bank entry P80188) can be substituted by at least one amino acid that is not present at this specific position in the respective natural polypeptide sequence. The term "mutagenesis" also includes the (additional) modification of the length of sequence segments by deletion or insertion of one or more amino acids. Thus, it is within the scope of the invention that, for example, one amino acid at a chosen sequence position is replaced by a stretch of three random mutations, leading to an insertion of two amino acid residues compared to the length of the respective segment of the wild type protein. Such an insertion of deletion may be introduced independently from each other in any of the peptide segments that can be subjected to mutagenesis in the invention. In one exemplary embodiment of the invention, an insertion of several mutations may be introduced into the loop AB of the chosen lipocalin scaffold (cf. International Patent Application WO 2005/019256 which is incorporated by reference its entirety herein). The term "random mutagenesis" means that no predetermined single amino acid (mutation) is present at a certain sequence position but that at least two amino acids can be incorporated with a certain probability at a predefined sequence position during mutagenesis.

The coding sequence of human Lipocalin 2 is used as a starting point for the mutagenesis of the peptide segments selected in the present invention. For the mutagenesis of the recited amino acid positions, the person skilled in the art has at his disposal the various established standard methods for site-directed mutagenesis (Sambrook, J. et al. (1989), supra). A commonly used technique is the introduction of mutations by means of PCR (polymerase chain reaction) using mixtures of synthetic oligonucleotides, which bear a degenerate base composition at the desired sequence positions. For example, use of the codon NNK or NNS (wherein N=adenine, guanine or cytosine or thymine; K=guanine or thymine; S=adenine or cytosine) allows incorporation of all 20 amino acids plus the amber stop codon during mutagenesis, whereas the codon VVS limits the number of possibly incorporated amino acids to 12, since it excludes the amino acids Cys, Ile, Leu, Met, Phe, Trp, Tyr, Val from being incorporated into the selected position of the polypeptide sequence; use of the codon NMS (wherein M=adenine or cytosine), for example, restricts the number of possible amino acids to 11 at a selected sequence position since it excludes the amino acids Arg, Cys, Gly, Ile, Leu, Met, Phe, Trp, Val from being incorporated at a selected sequence position. In this respect it is noted that codons for other amino acids (than the regular 20 naturally occurring amino acids) such as selenocystein or pyrrolysine can also be incorporated into a nucleic acid of a mutein. It is also possible, as described by Wang, L., et al. (2001) Science 292, 498-500, or Wang, L., and Schultz. P. G. (2002) Chem. Comm. 1, 1-11, to use "artificial" codons such as UAG which are usually recognized as stop codons in order to insert other unusual amino acids, for example o-methyl-L-tyrosine or p-aminophenylalanine.

The use of nucleotide building blocks with reduced base pair specificity, as for example inosine, 8-oxo-2'deoxyguanosine or 6(2-deoxy-β-D-ribofuranosyl)-3,4-dihydro-8H-pyrimindo-1,2-oxazine-7-one (Zaccolo et al. (1996) J. Mol. Biol. 255, 589-603), is another option for the introduction of mutations into a chosen sequence segment.

A further possibility is the so-called triplet-mutagenesis. This method uses mixtures of different nucleotide triplets, each of which codes for one amino acid, for incorporation into the coding sequence (Virnekäs B, Ge L, Plückthun A. Schneider K C, Wellnhofer G, Moroney S E. 1994 Trinucleotide phosphoramidites: ideal reagents for the synthesis of mixed oligonucleotides for random mutagenesis. Nucleic Acids Res 22, 5600-5607).

One possible strategy for introducing mutations in the selected regions of the respective polypeptides is based on the use of four oligonucleotides, each of which is partially derived from one of the corresponding sequence segments to be mutated. When synthesizing these oligonucleotides, a person skilled in the art can employ mixtures of nucleic acid building blocks for the synthesis of those nucleotide triplets which correspond to the amino acid positions to be mutated so that codons encoding all natural amino acids randomly arise, which at last results in the generation of a lipocalin peptide library. For example, the first oligonucleotide corresponds in its sequence—apart from the mutated positions—to the coding strand for the peptide segment to be mutated at the most N-terminal position of the lipocalin polypeptide. Accordingly, the second oligonucleotide corresponds to the non-coding strand for the second sequence segment following in the polypeptide sequence. The third oligonucleotide corresponds in turn to the coding strand for the corresponding third sequence segment. Finally, the fourth oligonucleotide corresponds to the non-coding strand for the fourth sequence segment. A polymerase chain reaction can be performed with the respective first and second oligonucleotide and separately, if necessary, with the respective third and fourth oligonucleotide.

The amplification products of both of these reactions can be combined by various known methods into a single nucleic acid comprising the sequence from the first to the fourth sequence segments, in which mutations have been introduced at the selected positions. To this end, both of the products can for example be subjected to a new polymerase chain reaction using flanking oligonucleotides as well as one or more mediator nucleic acid molecules, which contribute the sequence between the second and the third sequence segment. In the choice of the number and arrangement within the sequence of the oligonucleotides used for the mutagenesis, the person skilled in the art has numerous alternatives at his disposal.

The nucleic acid molecules defined above can be connected by ligation with the missing 5'- and 3'-sequences of a nucleic acid encoding a lipocalin polypeptide and/or the vector, and can be cloned in a known host organism. A multitude of established procedures are available for ligation and cloning (Sambrook. J. et al. (1989), supra). For example, recognition sequences for restriction endonucleases also present in the sequence of the cloning vector can be engineered into the sequence of the synthetic oligonucleotides. Thus, after amplification of the respective PCR product and enzymatic cleavage the resulting fragment can be easily cloned using the corresponding recognition sequences.

Longer sequence segments within the gene coding for the protein selected for mutagenesis can also be subjected to random mutagenesis via known methods, for example by use of the polymerase chain reaction under conditions of increased error rate, by chemical mutagenesis or by using bacterial mutator strains. Such methods can also be used for further optimization of the target affinity or specificity of a lipocalin mutein. Mutations possibly occurring outside the segments of experimental mutagenesis are often tolerated or can even prove to be advantageous, for example if they contribute to an improved folding efficiency or folding stability of the lipocalin mutein.

According to one embodiment of the present invention, the above method includes subjecting the nucleic acid molecule encoding a human Lipocalin 2 protein to mutagenesis at least at 2 or 3 nucleotide triplets coding for any of the above indicated sequence positions of human Lipocalin 2.

In one further embodiment, the method further includes subjecting the nucleic acid molecule to mutagenesis at at least one nucleotide triplet coding for any of the sequence positions corresponding to the sequence positions 33, 36, 40, 41, 42, 43, 44, 46, 47, 48, 49, 50, 51, 52, 54, 55, 59, 65, 68, 70, 72, 73, 75, 77, 78, 79, 80, 81, 86, 87, 98, 96, 99, 100, 103, 106, 107, 110, 111, 125, 127, 132, 134, 136 and 138 of the linear polypeptide sequence of hNGAL.

In a still further embodiment, the method includes subjecting the nucleic acid molecule to mutagenesis at nucleotide triplets coding for at least any 2, 3, 4, 5, 6, 7, 8, 9, 10, 11, 12, 13, 14, 15, 16, 17, 18, 19 or 20 of the sequence positions corresponding to the sequence positions 33, 36, 40, 41, 42, 43, 44, 46, 47, 48, 49, 50, 51, 52, 54, 55, 59, 65, 68, 70, 72, 73, 75, 77, 78, 79, 80, 81, 86, 87, 98, 96, 99, 100, 103, 106, 107, 110, 111, 125, 127, 132, 134, 136 and 138 of the linear polypeptide sequence of human Lipocalin 2.

According to the method of the invention a mutein is obtained starting from a nucleic acid encoding hNGAL. Such a nucleic acid is subjected to mutagenesis and introduced into a suitable bacterial or eukaiyotic host organism by means of recombinant DNA technology. Obtaining a nucleic acid library of human Lipocalin 2 can be carried out using any suitable technique that is known in the art for generating lipocalin muteins with antibody-like properties, i.e. muteins that have affinity towards a given target. Examples of such combinatorial methods are described in detail in the international patent applications WO 99/16873, WO 00/75308, WO 03/029471, WO 03/029462, WO 03/029463, WO 2005/019254, WO 2005/019255, WO 2005/019256, or WO 2006/56464 for instance. The content of each of these patent applications is incorporated by reference herein in its entirety. After expression of the nucleic acid sequences that were subjected to mutagenesis in an appropriate host, the clones carrying the genetic information for the plurality of respective lipocalin muteins, which bind a given target can be selected from the library obtained. Well known techniques can be employed for the selection of these clones, such as phage display (reviewed in Kay, B. K. et al. (1996) supra; Lowman, H. B. (1997) supra or Rodi, D. J., and Makowski, L. (1999) supra), colony screening (reviewed in Pini, A. et al. (2002) *Comb. Chem. High Throughput Screen.* 5, 503-510), ribosome display (reviewed in Amstutz, P. et al. (2001) *Curr. Opin. Biotechnol.* 12, 400-405) or mRNA display as reported in Wilson. D. S. et al. (2001) *Proc. Natl. Acad. Sci. USA* 98, 3750-3755 or the methods specifically described in WO 99/16873, WO 00/75308, WO 03/029471, WO 03/029462, WO 03/029463, WO 2005/019254, WO 2005/019255, WO 2005/019256, or WO 2006/56464.

In accordance with this disclosure, step (c) further comprises in another embodiment of the above methods:
  (i) providing as a given target/ligand a compound selected from the group consisting of a chemical compound in free or conjugated form that exhibits features of an immunological hapten, a peptide, a protein or another macromolecule such as a polysaccharide, a nucleic acid molecule (DNA or RNA, for example) or an entire virus particle or viroid, for example,
  (ii) contacting the plurality of muteins with said target/ligand in order to allow formation of complexes between said ligand and muteins having binding affinity for said target/ligand, and
  (iii) removing muteins having no or no substantial binding affinity.

In specific embodiments of the invention, the target/ligand is a non-natural target which includes, but is not limited to a peptide, a protein, a fragment or a domain of a protein, or a small organic molecule. In one embodiment the small organic molecule is a compound showing the features of an immunological hapten. In a further embodiment, the peptide is an amyloid beta peptide, such as Aβ40 peptide or an Aβ42 peptide. In still another embodiment, the non-natural targe is fibronectin or a domain thereof, such as the EB-domain or a fragment of the EB-domain.

In one embodiment of the methods of the invention, the selection in step (c) is carried out under competitive conditions. Competitive conditions as used herein means that selection of muteins encompasses at least one step in which the muteins and the given non-natural ligand of human Lipocalin 2 (target) are brought in contact in the presence of an additional ligand, which competes with binding of the muteins to the target. This additional ligand may be a physiological ligand of the target, an excess of the target itself or any other non-physiological ligand of the target that binds at least an overlapping epitope to the epitope recognized by the muteins of the invention and thus interferes with target binding of the muteins. Alternatively, the additional ligand competes with binding of the muteins by complexing an epitope distinct from the binding site of the muteins to the target by allosteric effects.

An embodiment of the phage display technique (reviewed in Kay, B. K. et al. (1996), supra; Lowman, H. B. (1997) supra or Rodi, D. J., and Makowski, L. (1999), supra) using temperent M13 phage is given as an example of a selection method that can be employed in the present invention. Another embodiment of the phage display technology that can be used for selection of muteins of the invention is the hyperphage phage technology as described by Broders et al. (Broders et al. (2003) "Hyperphage. Improving antibody presentation in phage display." *Methods Mol. Biol.* 205:295-

302). Other temperent phage such as f1 or lytic phage such as T7 may be employed as well. For the exemplary selection method. M13 phagemids are produced which allow the expression of the mutated lipocalin nucleic acid sequence as a fusion protein with a signal sequence at the N-terminus, preferably the OmpA-signal sequence, and with the capsid protein pIII of the phage M13 or fragments thereof capable of being incorporated into the phage capsid at the C-terminus. The C-terminal fragment ΔpIII of the phage capsid protein comprising amino acids 217 to 406 of the wild type sequence is preferably used to produce the fusion proteins. Especially preferred in one embodiment is a C-terminal fragment of pIII, in which the cysteine residue at position 201 is missing or is replaced by another amino acid.

Accordingly, a further embodiment of the methods of the invention involves operably fusing a nucleic acid coding for the plurality of muteins of human Lipocalin 2 and resulting from mutagenesis at the 3' end with a gene coding for the coat protein pIII of a filamentous bacteriophage of the M13-family or for a fragment of this coat protein, in order to select at least one mutein for the binding of a given ligand.

The fusion protein may comprise additional components such as an affinity tag, which allows the immobilization, detection and/or purification of the fusion protein or its parts. Furthermore, a stop codon can be located between the sequence regions encoding the lipocalin or its muteins and the phage capsid gene or fragments thereof, wherein the stop codon, preferably an amber stop codon, is at least partially translated into an amino acid during translation in a suitable suppressor strain.

For example, the phasmid vector pTLPC27, now also called pTlc27 that is described here can be used for the preparation of a phagemid library encoding human Lipocalin 2 muteins. The inventive nucleic acid molecules coding for the hNGAL muteins are inserted into the vector using the two BstXI restriction sites. After ligation a suitable host strain such as *E. coli* XL1-Blue is transformed with the resulting nucleic acid mixture to yield a large number of independent clones. A respective vector can be generated for the preparation of a hyperphagemid library, if desired.

The resulting library is subsequently superinfected in liquid culture with an appropriate M13-helper phage or hyperphage in order to produce functional phagemids. The recombinant phagemid displays the lipocalin mutein on its surface as a fusion with the coat protein pIII or a fragment thereof, while the N-terminal signal sequence of the fusion protein is normally cleaved off. On the other hand, it also bears one or more copies of the native capsid protein pIII supplied by the helper phage and is thus capable of infecting a recipient, in general a bacterial strain carrying an F- or F'-plasmid. In case of hyperphage display, the hyperphagemids display the lipocalin muteins on their surface as a fusion with the infective coat protein pIII but no native capsid protein. During or after infection with helper phage or hyperphage, gene expression of the fusion protein between the lipocalin mutein and the capsid protein pIII can be induced, for example by addition of anhydrotetracycline. The induction conditions are chosen such that a substantial fraction of the phagemids obtained displays at least one lipocalin mutein on their surface. In case of hyperphage display induction conditions result in a population of hyperphagemids carrying between three and five fusion proteins consisting of the lipocalin mutein and the capsid protein pIII. Various methods are known for isolating the phagemids, such as precipitation with polyethylene glycol. Isolation typically occurs after an incubation period of 6-8 hours.

The isolated phasmids can then be subjected to selection by incubation with the desired target, wherein the target is presented in a form allowing at least temporary immobilization of those phagemids which carry muteins with the desired binding activity as fusion proteins in their coat. Among the various embodiments known to the person skilled in the art, the target can, for example, be conjugated with a carrier protein such as serum albumin and be bound via this carrier protein to a protein binding surface, for example polystyrene. Microtiter plates suitable for ELISA techniques or so-called "immuno-sticks" can preferably be used for such an immobilization of the target. Alternatively, conjugates of the target with other binding groups, such as biotin, can be used. The target can then be immobilized on a surface which selectively binds this group, for example microtiter plates or paramagnetic particles coated with streptavidin, neutravidin or avidin. If the target is fused to an Fc portion of an immunoglobulin, immobilization can also be achieved with surfaces, for example microtiter plates or paramagnetic particles, which are coated with protein A or protein G.

Non-specific phagemid-binding sites present on the surfaces can be saturated with blocking solutions as they are known for ELISA methods. The phagemids are then typically brought into contact with the target immobilized on the surface in the presence of a physiological buffer. Unbound phagemids are removed by multiple washings. The phagemid particles remaining on the surface are then eluted. For elution, several methods are possible. For example, the phagemids can be eluted by addition of proteases or in the presence of acids, bases, detergents or chaotropic salts or under moderately denaturing conditions. A preferred method is the elution using buffers of pH 2.2, wherein the eluate is subsequently neutralized. Alternatively, a solution of the free target can be added in order to compete with the immobilized target for binding to the phagemids or target-specific phagemids can be eluted by competition with immunoglobulins or natural liganding proteins which specifically bind to the target of interest.

Afterwards, *E. coli* cells are infected with the eluted phagemids. Alternatively, the nucleic acids can be extracted from the eluted phagemids and used for sequence analysis, amplification or transformation of cells in another manner. Starting from the *E. coli* clones obtained in this way, fresh phagemids or hyperphagemids are again produced by superinfection with M13 helper phages or hyperphage according to the method described above and the phagemids amplified in this way are once again subjected to a selection on the immobilized target. Multiple selection cycles are often necessary in order to obtain the phagemids with the muteins of the invention in sufficiently enriched form. The number of selection cycles is preferably chosen such that in the subsequent functional analysis at least 0.1% of the clones studied produce muteins with detectable affinity for the given target. Depending on the size, i.e. the complexity of the library employed, 2 to 8 cycles are typically required to this end.

For the functional analysis of the selected muteins, an *E. coli* strain is infected with the phagemids obtained from the selection cycles and the corresponding double stranded phasmid DNA is isolated. Starting from this phasmid DNA, or also from the single-stranded DNA extracted from the phagemids, the nucleic acid sequences of the selected muteins of the invention can be determined by the methods known in the art and the amino acid sequence can be deduced therefrom. The mutated region or the sequence of the entire hNGAL mutein can be subcloned on another expression vector and expressed in a suitable host organism. For example, the vector pTLPC26 now also called pTlc26 can be used for expression in *E. coli* strains such as *E. coli* TG1. The muteins of human Lipocalin 2 thus produced can be purified by various biochemical methods. The hNGAL muteins produced, for example with pTlc26, carry the affinity peptide Strep-tag II (Schmidt et al., supra) at their C-termini and can therefore preferably be purified by streptavidin affinity chromatography.

The selection can also be carried out by means of other methods. Many corresponding embodiments are known to the person skilled in the art or are described in the literature. Moreover, a combination of methods can be applied. For example, clones selected or at least enriched by "phage display" can additionally be subjected to "colony screening". This procedure has the advantage that individual clones can directly be isolated with respect to the production of a human Lipocalin 2 mutein with detectable binding affinity for a target.

In addition to the use of *E. coli* as host organism in the "phage display" technique or the "colony screening" method, other bacterial strains, yeast or also insect cells or mammalian cells can be used for this purpose. Further to the selection of a human Lipocalin 2 mutein from a random library as described above, evolutive methods including limited mutagenesis can also be applied in order to optimize a mutein that already possesses some binding activity for the target with respect to affinity or specificity for the target.

Once a mutein with affinity to a given target has been selected, it is additionally possible to subject such a mutein to another mutagenesis in order to subsequently select variants of even higher affinity or variants with improved properties such as higher thermostability, improved serum stability, thermodynamic stability, improved solubility, improved monomeric behavior, improved resistance against thermal denaturation, chemical denaturation, proteolysis, or detergents etc. This further mutagenesis, which in case of aiming at higher affinity can be considered as in vitro "affinity maturation", can be achieved by site specific mutation based on rational design or a random mutation. Another possible approach for obtaining a higher affinity or improved properties is the use of error-prone PCR, which results in point mutations over a selected range of sequence positions of the lipocalin mutein. The error-prone PCR can be carried out in accordance with any known protocol such as the one described by Zaccolo et al. (1996) *J. Mol. Biol.* 255, 589-603. Other methods of random mutagenesis that are suitable for such purposes include random insertion/deletion (RID) mutagenesis as described by Murakami et al. (2002) *Nat. Biotechnol.* 20, 76-81 or nonhomologous random recombination (NRR) as described by Bittker et al. (2002) *Nat. Biotechnol.* 20, 1024-1029. If desired, affinity maturation can also be carried out according to the procedure described in WO 00/75308 or Schlehuber et al. (2000) *J. Mol. Biol.* 297, 1105-1120, where muteins of the bilin-binding protein having high affinity to digoxigenin were obtained. A further approach for improving the affinity is to carry out positional saturation mutagenesis. In this approach "small" nucleic acid libraries can be created in which amino acid exchanges/mutations are only introduced at single positions within any of the four loop segments. These libraries are then directly subjected to a selection step (affinity screening) without further rounds of panning. This approach allows the identification of residues that contribute to improved binding of the desired target and allows identification of "hot spots" that are important for the binding.

In one embodiment, the above method for modifying a mutein further includes introducing a Cys residue at at least one of any of the sequence positions that correspond to sequence positions 14, 21, 60, 84, 88, 116, 141, 145, 143, 146 or 158 of the wild type sequence of human Lipocalin 2 and coupling a moiety that is able to modify the serum half time of said mutein via the thiol group of a Cys residue introduced at at least one of any of the sequence positions that correspond to sequence positions 14, 21, 60, 84, 88, 116, 141, 145, 143, 146 or 158 of the wild type sequence of hNGAL. The moiety that is able to modify the serum half time of said mutein may be selected from the group consisting of a polyalkylene glycol molecule and hydroxyethylstarch.

In a further aspect, the present invention is directed to a mutein of human Lipocalin 2 having detectable binding affinity to a given non-natural ligand of human Lipocalin 2, which is obtainable by or obtained by the above-detailed methods of the invention.

In some human Lipocalin 2 muteins of the invention, the naturally occurring disulfide bond between Cys 76 and Cys 175 is removed. Accordingly, such muteins (or any other human Lipocalin 2 mutein that does not comprise an intramolecular disulfide bond) can be produced in a cell compartment having a reducing redox milieu, for example, in the cytoplasma of Gram-negative bacteria.

In case a lipocalin mutein of the invention comprises intramolecular disulfide bonds, it may be preferred to direct the nascent polypeptide to a cell compartment having an oxidizing redox milieu using an appropriate signal sequence. Such an oxidizing environment may be provided by the periplasm of Gram-negative bacteria such as *E. coli*, in the extracellular milieu of Gram-positive bacteria or in the lumen of the endoplasmatic reticulum of eukaryotic cells and usually favors the formation of structural disulfide bonds.

It is, however, also possible to produce a mutein of the invention in the cytosol of a host cell, preferably *E. coli*. In this case, the polypeptide can either be directly obtained in a soluble and folded state or recovered in form of inclusion bodies, followed by renaturation in vitro. A further option is the use of specific host strains having an oxidizing intracellular milieu, which may thus allow the formation of disulfide bonds in the cytosol (Venturi et al. (2002) *J. Mol. Biol.* 315, 1-8).

However, a mutein of the invention may not necessarily be generated or produced only by use of genetic engineering. Rather, a lipocalin mutein can also be obtained by chemical synthesis such as Merrifield solid phase polypeptide synthesis or by in vitro transcription and translation. It is for example possible that promising mutations are identified using molecular modeling and then to synthesize the wanted (designed) polypeptide in vitro and investigate the binding activity for a given target. Methods for the solid phase and/or solution phase synthesis of proteins are well known in the art (reviewed, e.g., in Lloyd-Williams et al. (1997) *Chemical Approaches to the Synthesis of Peptides and Proteins*. CRC Press, Boca Raton, Fields, GB, and Colowick (1997) *Solid-Phase Peptide Synthesis*. Academic Press, San Diego, or Bruckdorfer et al. (2004) *Curr. Pharm. Biotechnol.* 5, 29-43).

In another embodiment, the muteins of the invention may be produced by in vitro transcription/translation employing well-established methods known to those skilled in the art.

The invention also relates to a pharmaceutical composition comprising at least one inventive mutein referred to in the claims or a fusion protein or conjugates thereof and, optionally, a pharmaceutically acceptable excipient.

The lipocalin muteins according to the invention can be administered via any parenteral or non-parenteral (enteral) route that is therapeutically effective for proteinaceous drugs. Parenteral application methods comprise, for example, intracutaneous, subcutaneous, intramuscular or intravenous injection and infusion techniques, e.g. in the form of injection solutions, infusion solutions or tinctures, as well as aerosol installation and inhalation, e.g. in the form of aerosol mixtures, sprays or powders. Non-parenteral delivery modes are, for instance, orally, e.g. in the form of pills, tablets, capsules, solutions or suspensions, or rectally, e.g. in the form of suppositories. The muteins of the invention can be administered systemically or topically in formulations containing conventional non-toxic pharmaceutically acceptable excipients or carriers, additives and vehicles as desired.

In one embodiment of the present invention the pharmaceutical is administered parenterally to a mammal, and in particular to humans. Corresponding administration methods include, but are not limited to, for example, intracutaneous, subcutaneous, intramuscular or intravenous injection and infusion techniques, e.g. in the form of injection solutions, infusion solutions or tinctures as well as aerosol installation and inhalation, e.g. in the form of aerosol mixtures, sprays or powders. A combination of intravenous and subcutaneous infusion and/or injection might be most convenient in case of compounds with a relatively short serum half life. The pharmaceutical composition may be an aqueous solution, an oil-in water emulsion or a water-in-oil emulsion.

In this regard it is noted that transdermal delivery technologies, e.g. iontophoresis, sonophoresis or microneedle-enhanced delivery, as described in Meidan and Michniak (2004) *Am. J. Ther.* 11(4), 312-316, can also be used for transdermal delivery of the muteins described herein. Non-parenteral delivery modes are, for instance, oral, e.g. in the form of pills, tablets, capsules, solutions or suspensions, or rectal administration, e.g. in the form of suppositories. The muteins of the invention can be administered systemically or topically in formulations containing a variety of conventional non-toxic pharmaceutically acceptable excipients or carriers, additives, and vehicles.

The dosage of the mutein applied may vary within wide limits to achieve the desired preventive effect or therapeutic response. It will, for instance, depend on the affinity of the compound for a chosen ligand as well as on the half-life of the complex between the mutein and the ligand in vivo. Further, the optimal dosage will depend on the biodistribution of the mutein or its fusion protein or its conjugate, the mode of administration, the severity of the disease/disorder being treated as well as the medical condition of the patient. For example, when used in an ointment for topical applications, a high concentration of the human Lipocalin 2 mutein can be used. However, if wanted, the mutein may also be given in a sustained release formulation, for example liposomal dispersions or hydrogel-based polymer microspheres, like PolyActive™ or OctoDEX™ (cf. Bos et al., *Business Briefing: Pharmatech* 2003: 1-6).

Accordingly, the muteins of the present invention can be formulated into compositions using pharmaceutically acceptable ingredients as well as established methods of preparation (Gennaro and Gennaro (2000) *Remington: The Science and Practice of Pharmacy*, 20th Ed., Lippincott Williams & Wilkins, Philadelphia, PA). To prepare the pharmaceutical compositions, pharmaceutically inert inorganic or organic excipients can be used. To prepare e.g. pills, powders, gelatine capsules or suppositories, for example, lactose, talc, stearic acid and its salts, fats, waxes, solid or liquid polyols, natural and hardened oils can be used. Suitable excipients for the production of solutions, suspensions, emulsions, aerosol mixtures or powders for reconstitution into solutions or aerosol mixtures prior to use include water, alcohols, glycerol, polyols, and suitable mixtures thereof as well as vegetable oils.

The pharmaceutical composition may also contain additives, such as, for example, fillers, binders, wetting agents, glidants, stabilizers, preservatives, emulsifiers, and furthermore solvents or solubilizers or agents for achieving a depot effect. The latter is that fusion proteins may be incorporated into slow or sustained release or targeted delivery systems, such as liposomes and microcapsules.

The formulations can be sterilized by numerous means, including filtration through a bacteria-retaining filter, or by incorporating sterilizing agents in the form of sterile solid compositions which can be dissolved or dispersed in sterile water or other sterile medium just prior to use.

A mutein of the present invention or a fusion protein or a conjugate thereof can be employed in many applications. In general, such a mutein can be used in all applications antibodies are used, except those with specifically rely on the glycosylation of the Fc part.

Therefore, in another aspect of the invention, the invented muteins of human Lipocalin 2 are used for the binding and/or detection of a given non-natural ligand of human Lipocalin 2. Such use may comprise the steps of contacting the mutein with a sample suspected of containing the given ligand under suitable conditions, thereby allowing formation of a complex between the mutein and the given ligand, and detecting the complexed mutein by a suitable signal.

The detectable signal can be caused by a label, as explained above, or by a change of physical properties due to the binding, i.e. the complex formation, itself. One example is plasmon surface resonance, the value of which is changed during binding of binding partners from which one is immobilized on a surface such as a gold foil.

The muteins of human Lipocalin 2 disclosed herein may also be used for the separation of a given non-natural ligand of human Lipocalin 2. Such use may comprise the steps of contacting the mutein with a sample supposed to contain said ligand under suitable conditions, thereby allowing formation of a complex between the mutein and the given ligand, and separating the mutein/ligand complex from the sample.

In both the use of the mutein for the detection of a given non-natural ligand as well as the separation of a given ligand, the mutein and/or the target may be immobilized on a suitable solid phase.

The human Lipocalin 2 muteins of the invention may also be used to target a compound to a pre-selected site. In one such embodiment, a mutein of human Lipocalin 2 is used for the targeting of a pharmaceutically active compound to a pre-selected site in an organism or tissue, comprising of:
  a) conjugating the mutein with said compound, and
  b) delivering the mutein/compound complex to the pre-selected site.

For such a purpose the mutein is contacted with the compound of interest in order to allow complex formation. Then the complex comprising the mutein and the compound of interest are delivered to the pre-selected site. This may, for example, be achieved by coupling the mutein to a targeting moiety, such as an antibody, antibody fragment or lipocalin mutein or lipocalin mutein fragment wit binding affinity for the selected target.

This use is in particular suitable, but not restricted to, for delivering a drug (selectively) to a pre-selected site in an organism, such as an infected body part, tissue or organ which is supposed to be treated with the drug. Besides formation of a complex between mutein and compound of interest, the mutein can also be reacted with the given compound to yield a conjugate of mutein and compound. Similar to the above complex, such a conjugate may be suitable to deliver the compound to the pre-selected target site. Such a conjugate of mutein and compound may also include a linker that covalently links mutein and compound to each other. Optionally, such a linker is stable in the bloodstream but is cleavable in a cellular environment.

The muteins disclosed herein and its derivatives can thus be used in many fields similar to antibodies or fragments thereof. In addition to their use for binding to a support, allowing the target of a given mutein or a conjugate or a fusion protein of this target to be immobilized or separated, the muteins can be used for labeling with an enzyme, an antibody, a radioactive substance or any other group having biochemical activity or defined binding characteristics. By doing so, their respective targets or conjugates or fusion proteins thereof can be detected or brought in contact with them. For example, muteins of the invention can serve to detect chemical structures by means of established analytical methods (e.g. ELISA or Western Blot) or by microscopy or immunosensorics. Here, the detection signal can either be generated directly by use of a suitable mutein conjugate or fusion protein or indirectly by immunochemical detection of the bound mutein via an antibody.

Numerous possible applications for the inventive muteins also exist in medicine. In addition to their use in diagnostics and drug delivery, a mutant polypeptide of the invention, which binds, for example, tissue- or tumor-specific cellular surface molecules can be generated. Such a mutein may, for example, be employed in conjugated form or as a fusion protein for "tumor imaging" or directly for cancer therapy.

Thus, the present invention also involves the use of the human Lipocalin 2 muteins of the invention for complex formation with a given non-natural ligand or target.

In a further aspect, the present invention also encompasses the use of a mutein according to the invention for the manufacture of a pharmaceutical composition. The pharmaceutical composition thus obtained may be suited for the treatment of neugrodegenerative disorders, such as Alzheimer disease. The pharmaceutical composition can also be used for the treatment of cancer, the treatment of fibrosis ro the treatment of an inflammation. The pharmaceutical composition may be used as monotherapy or as combination therapy.

In still another aspect, the present invention features a diagnostic or analytical kit comprising a mutein according to the present invention.

Another aspect of the present invention relates to a method of treating a subject suffering from a neurodegenerative disease, or cancer, or fibrosis, or an inflammation, including administering a respective mutein of the invention or a pharmaceutical composition comprising a mutein of the invention to a subject in need thereof.

The subject in need of such a treatment may be a mammal, such as a human, a dog, a mouse, a rat, a pig, an ape such as cymologous monkeys to name only a few illustrative examples.

In still another aspect, the present invention features a method for in vivo imaging in a subject, including administering to said subject a mutein of the invention or a pharmaceutical composition comprising a mutein of the invention. The subject may be defined as above.

The invention is further illustrated by the following non-limiting Examples and the attached drawings in which:

FIG. 1 illustrates the PCR assembly strategy for the simultaneous random mutagenesis of the 20 amino acid positions 36, 40, 41, 49, 52, 68, 70, 72, 73, 77, 79 81, 96, 100, 103, 106, 125, 127, 132, and 134 (underlined and numbered) in the amino acid sequence of the mature Lcn2. These 20 positions were divided into four sequence subsets. For randomization of the amino acids in each subset an oligodeoxynucleotide was synthesized (SEQ ID NO: 1, SEQ ID NO:60, SEQ ID NO:3, SEQ ID NO:4) wherein NNK mixtures of the nucleotides were employed at the mutated codons. N means a mixture of all four bases A, C, G, and T while K means a mixture of only the two bases G and T; hence such a triplet encodes all 20 natural amino acids as well as the amber stop codon TAG, which is translated as glutamine in the *E. coli* supE-strains XL1-blue (Bullock et al., BioTechniques 5 (1987), 376-378) or TG1 (Sambrook et al., Molecular Cloning. A Laboratory Manual (1989), Cold Spring Harbor Press) that were used for phagemid production and gene expression. Four additional oligodeoxynucleotides (SEQ ID NO:61, SEQ ID NO:6, SEQ ID NO:7, SEQ ID NO:8) with fixed nucleotide sequences corresponding to the non-coding strand (written below the DNA double strand sequence in 3'-5' direction) and filling the gaps between the aforementioned oligodeoxynucleotides were also used in the assembly reaction. Two shorter flanking oligodeoxynucleotides (SEQ ID NO:9 and SEQ ID NO:10), which were added in excess and carried biotin groups, served as primers for the PCR amplification of the assembled, entirely synthetic gene fragment. The two flanking primers each encompassed a BstXI restriction site (CCANNNNNNTGG) (SEQ ID NO: 56), giving rise to mutually non-compatible overhangs upon enzyme digest. This special arrangement of restriction sites enabled a particularly efficient ligation and cloning of the synthetic gene. Substitution of the amino acid Gln28 to His with respect to the original Lcn2 sequence was necessary to introduce the first BstXI site, while the second one naturally occurs in the cDNA of Lcn2. Furthermore, the unpaired residue Cys87 was replaced by Ser during the gene assembly. After one pot PCR the resulting gene fragment was inserted into a vector providing the missing parts of the Lcn2 structural gene. This illustration also depicts two short primers (SEQ ID NO: 45 and SEQ ID NO: 46) upstream and downstream, respectively, of the cassette flanked by the two BstXI restriction sites, which served for double stranded DNA sequencing. FIG. 1 discloses the full-length DNA sequence as SEQ ID NO: 62 and the full-length protein sequence as SEQ ID NO: 63.

FIG. 2 illustrates the nucleotide sequence of a library of synthetic Lcn2 genes (only the central cassette flanked by the two BstXI restriction sites, as in FIG. 1, is shown). This gene fragment was prepared by Sloning BioTechnology GmbH. Compared with the DNA library described in FIG. 1 there are two differences. First, whenever possible codons optimized for *E. coli* expression were used throughout for the non-mutated amino acid positions. Second, a mixture of 19 different triplets (GAC, TTC, CTG, CAC, AAT, AGC, ACC, GCA, ATG, CCT, GTT, TGG, GAG, CAA, ATC, GGA, CGT, GCA, TAC), each encoding a different amino acid except Cys, was employed at the 20 randomized positions, which are identical to the ones depicted in FIG. 1. Numbering of amino acids corresponds here to an internal scheme employed by Sloning BioTechnology GmbH, whereby Gly no. 1 is the first amino acid codon directly following the upstream BstX1 restriction site. FIG. 2 discloses SEQ ID NOS 64-66, respectively, in order of appearance.

FIG. 3 shows the SEC elution profiles of the recombinant Aβ fusion proteins Trx-Aβ28 (A) and MBP-Aβ40 (B) after expression in E. coli. The purity of both the synthetic Aβ40 and the recombinant AB fusion proteins was assessed by SDS-PAGE analysis (C). Both fusion proteins were expressed in the cytoplasm of E. coli JM83. After disruption of the cells with a French Pressure Cell the proteins were purified via His$_6$-tag (SEQ ID NO: 54) affinity chromatography and then further applied to a Superdex 75 HR 10/30 column in the case of Trx-Aβ28 or to a Superdex 200 HR 10/30 column in the case of MBP-Aβ40. Both proteins eluted mainly as monomer in the size exclusion chromatography and were essentially homogeneous after purification. Aβ40 was obtained from the Keck Foundation, treated with HFIP, evaporated in a SpeedVac and finally dissolved in distilled H$_2$O. The 15% gel shows samples of Aβ40 after the HFIP treatment and Trx-Aβ28 and MBP-Aβ40 after IMAC purification and SEC. M depicts the molecular weight marker with the corresponding band sizes in kDa displayed on the left of the gel.

Figure 4:
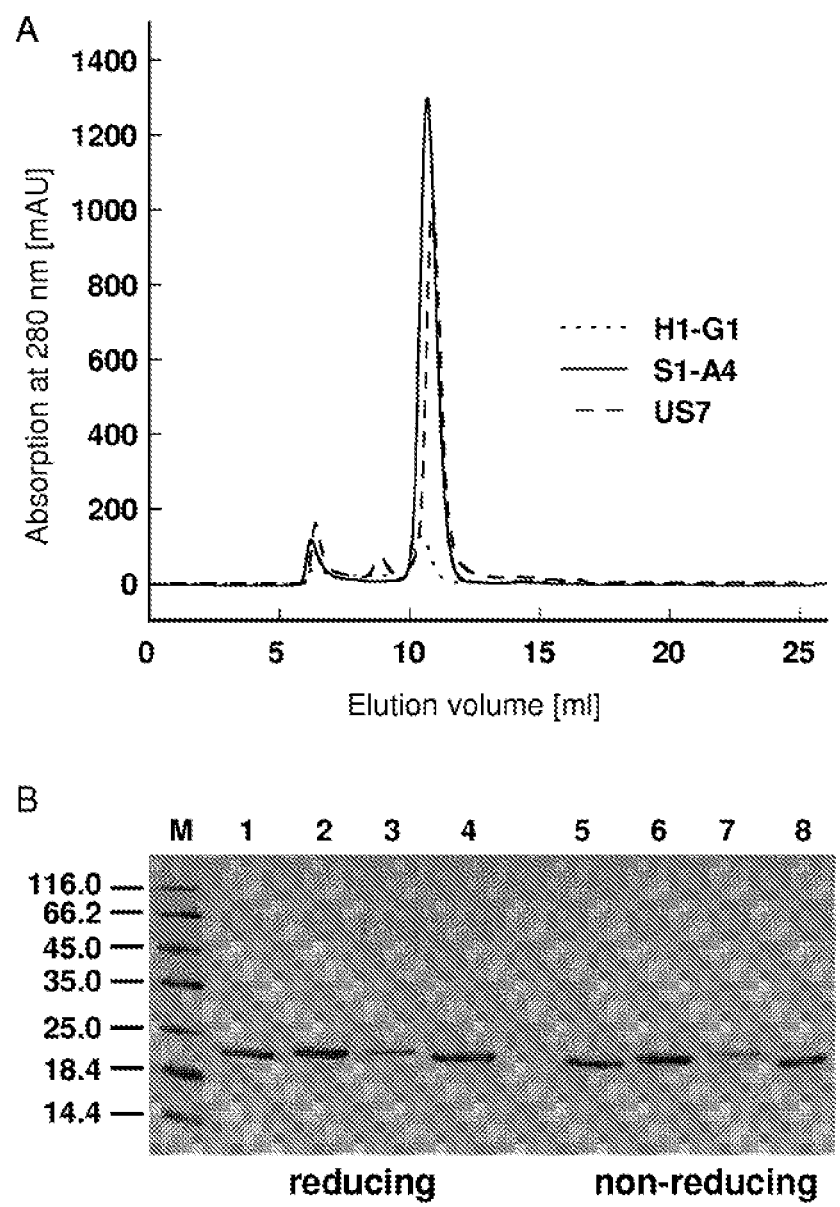

FIG. 4 represents an overlay of the SEC elution profiles of the Lcn2 muteins H1-G1, S1-A4, and US7 (A) and the analysis of the purified proteins via 15% SDS-PAGE (B). The three Lcn2 muteins H1-G1, S1-A4, and US7 were expressed in the periplasm of E. coli JM83 or TG1-F$^-$ (as shown here) and purified via Strep-tag II affinity chromatography. All three muteins eluted predominantly as monomeric proteins from the Superdex 75 HR 10/30 column with a retention volume of 10 to 11 ml. Peak intensities differed depending on the expression yield of the particular mutein. (B) shows a 15% SDS-PAGE analysis of recombinant wild-type Lcn2 (lanes 1, 5) and the muteins US7 (lanes 2, 6), H1-G1 (lanes 3, 7), and S1-A4 (lanes 4, 8) after Strep-tag II affinity purification and SEC. Lanes 1-4 show the Lcn2 muteins reduced with 2-mercaptoethanol, lanes 5-8 show the proteins under non-reducing conditions. M represents the molecular weight marker with the corresponding band sizes in kDa displayed on the left of the gel.

Figure 5:
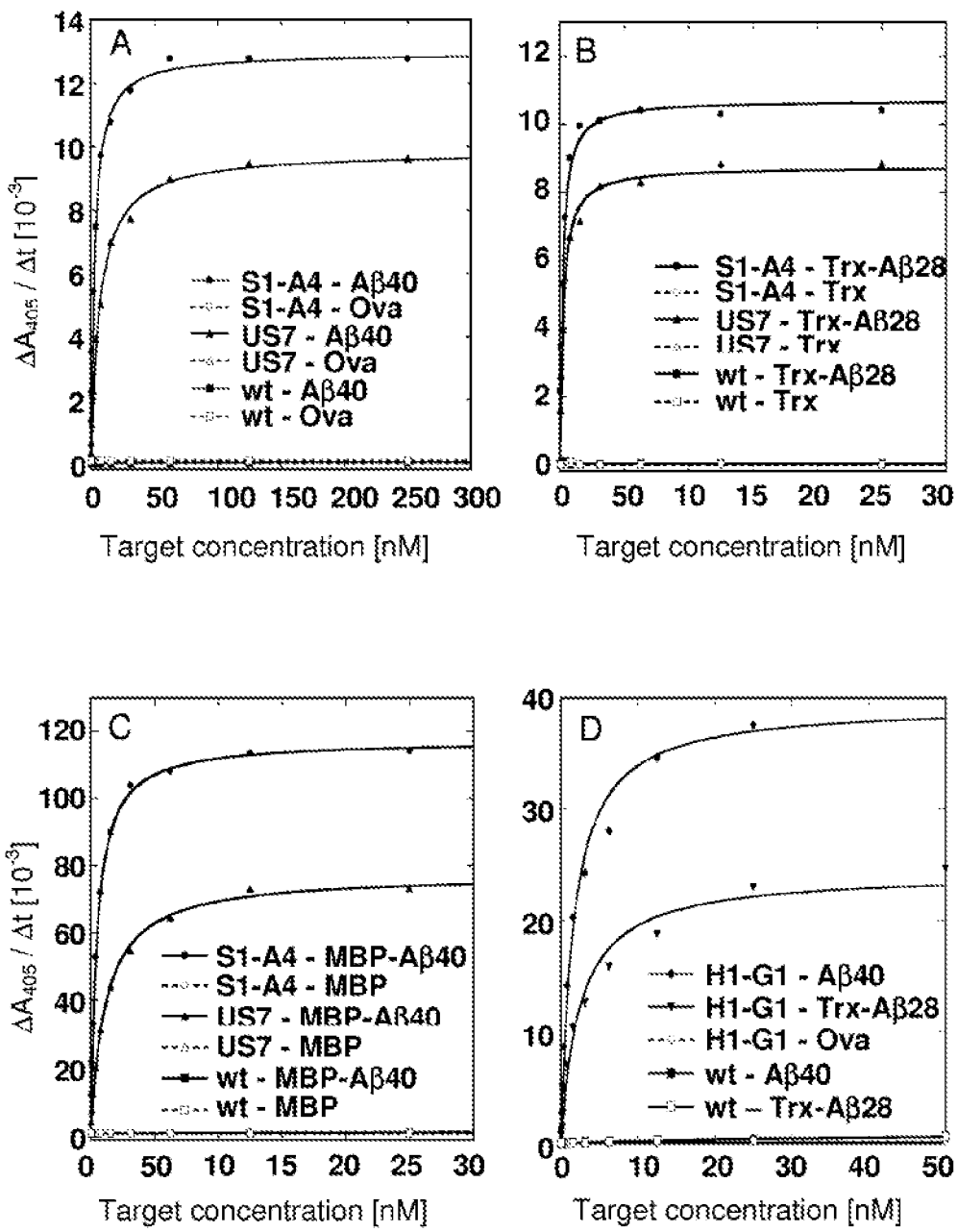

FIG. 5 depicts the binding activity of the Lcn2 muteins H1-G1, S1-A4, and US7 in capture ELISAs with different biotinylated Aβ targets. StrepMAB-Immo at 10 g/ml was immobilized on microtitre plates and employed for capturing of 1 μM Lcn2 muteins via the Strep-tag II. In figures A to C the binding of the Lcn2 muteins S1-A4 and US7 to (A) biotinylated A340, (B) biotinylated Trx-Aβ28, and (C) biotinylated MBP-Aβ40 are shown. Binding was detected by incubation with ExtrAvidin/AP and a subsequent chromogenic reaction with pNPP. Ovalbumin (Ova), thioredoxin (Trx), and maltose binding protein (MBP) were used as negative controls. Additionally, binding of wild-type (wt) lipocalin was tested. The data were fitted to a monovalent binding model. Figure D shows the same ELISA setup performed with Lcn2 H1-G1 and biotinylated Aβ40 and Trx-Aβ28 as targets. K$_D$ values determined for Aβ40 were 2.7 nM for S1-A4, 6.8 nM for US7, and 16.2 nM for H1-G1, corresponding values for Trx-Aβ28 were 1.9 nM, 2.4 nM, and 24.3 nM. Binding to MBP-A040 showed a K$_D$ value of 4.7 nM for S1-A4 and 11.4 nM for US7. Accordingly K$_D$ values for A316-27 were 2.6 nM and 2.1 nM.

Figure 6:
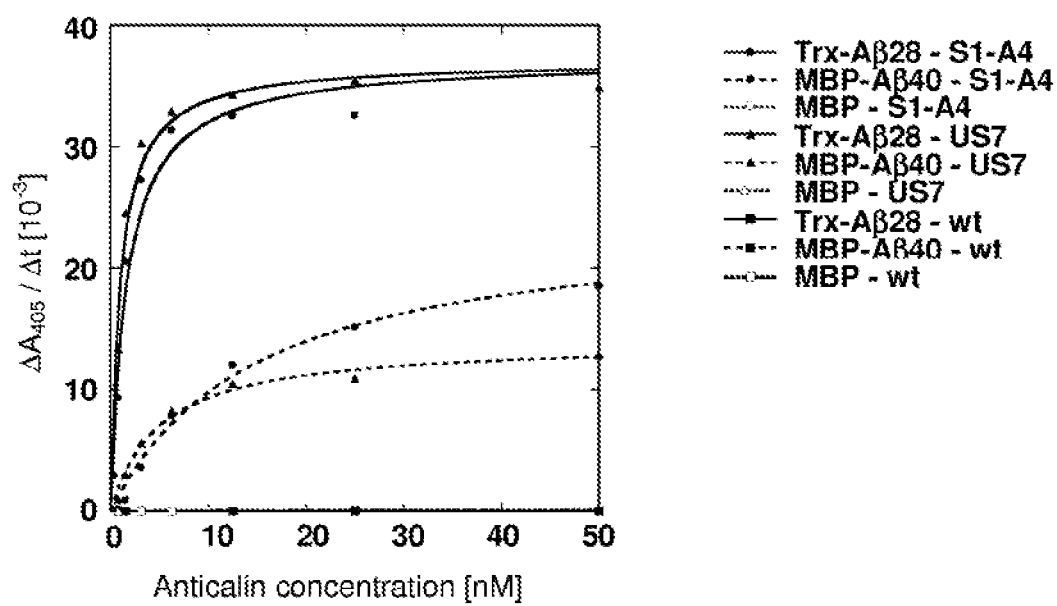

FIG. 6 shows the binding activity of the Lcn2 muteins S1-A4 and US7 in a direct ELISA. The Aβ targets Trx-Aβ28 and MBP-A(340 as well as the control protein maltose binding protein (MBP) were immobilized at 2 μM in PBS over night. Bound Lcn2 muteins were detected via their Strep-tag II using Streptavidin/AP followed by a chromogenic reaction with pNPP. As a control, the binding of wild-type (wt) lipocalin was tested. The data were fitted to a monovalent binding model. K$_D$ values determined for Trx-Aβ28 were 16.2 nM for S1-A4 and 9.6 nM for US7, corresponding values for MBP-Aβ40 were 149 nM and 49.7 nM.

Figure 7:
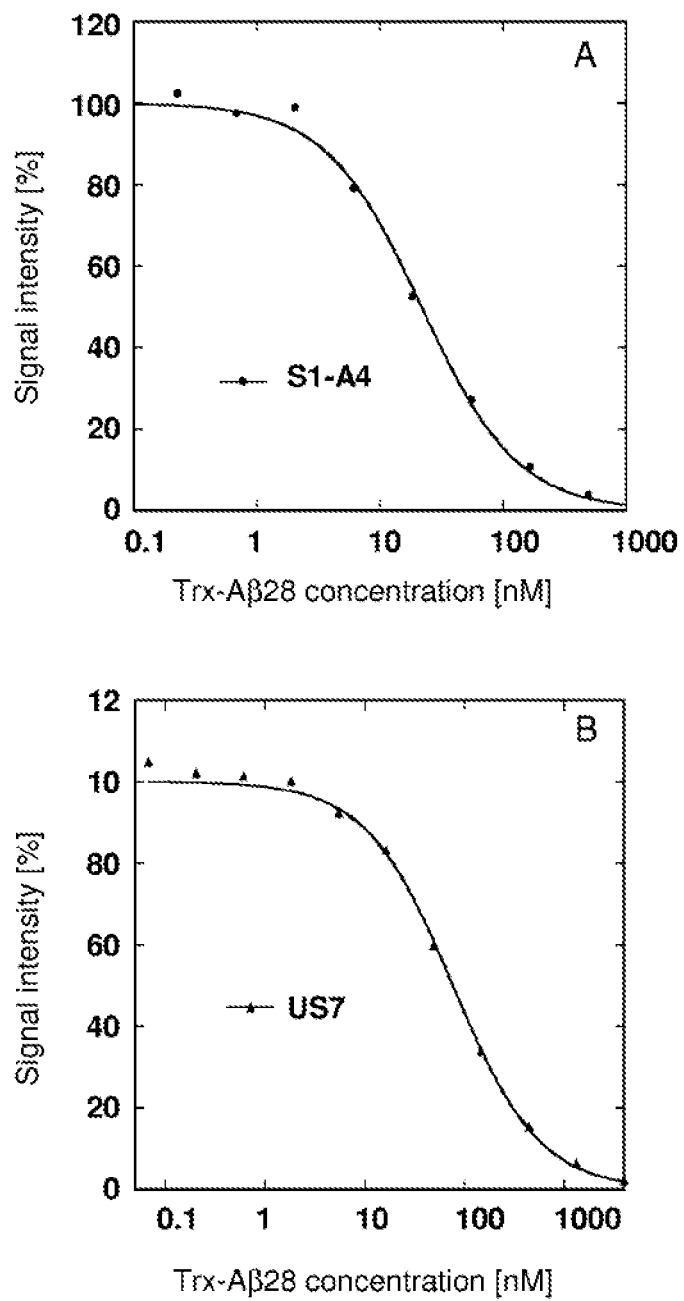

FIG. 7 shows the binding activity of the Lcn2 muteins S1-A4 (A) and US7 (B) in a competitive ELISA. StrepMAB-Immo was immobilized at 10 μg/ml on microtitre plates and employed for capturing of 1 μM Lcn2 mutein via the Strep-tag II. For competition, a constant concentration of biotinylated Trx-Aβ28 as tracer was mixed with varying concentrations of unlabeled Trx-Aβ28. Bound biotinylated Trx-Aβ28 was subsequently detected via incubation with ExtrAvidin/AP followed by a chromogenic reaction with pNPP. The data were fitted using a sigmoidal equation. The K$_D$ values were 21.7 nM for S1-A4 and 76.9 nM for US7.

Figure 8:
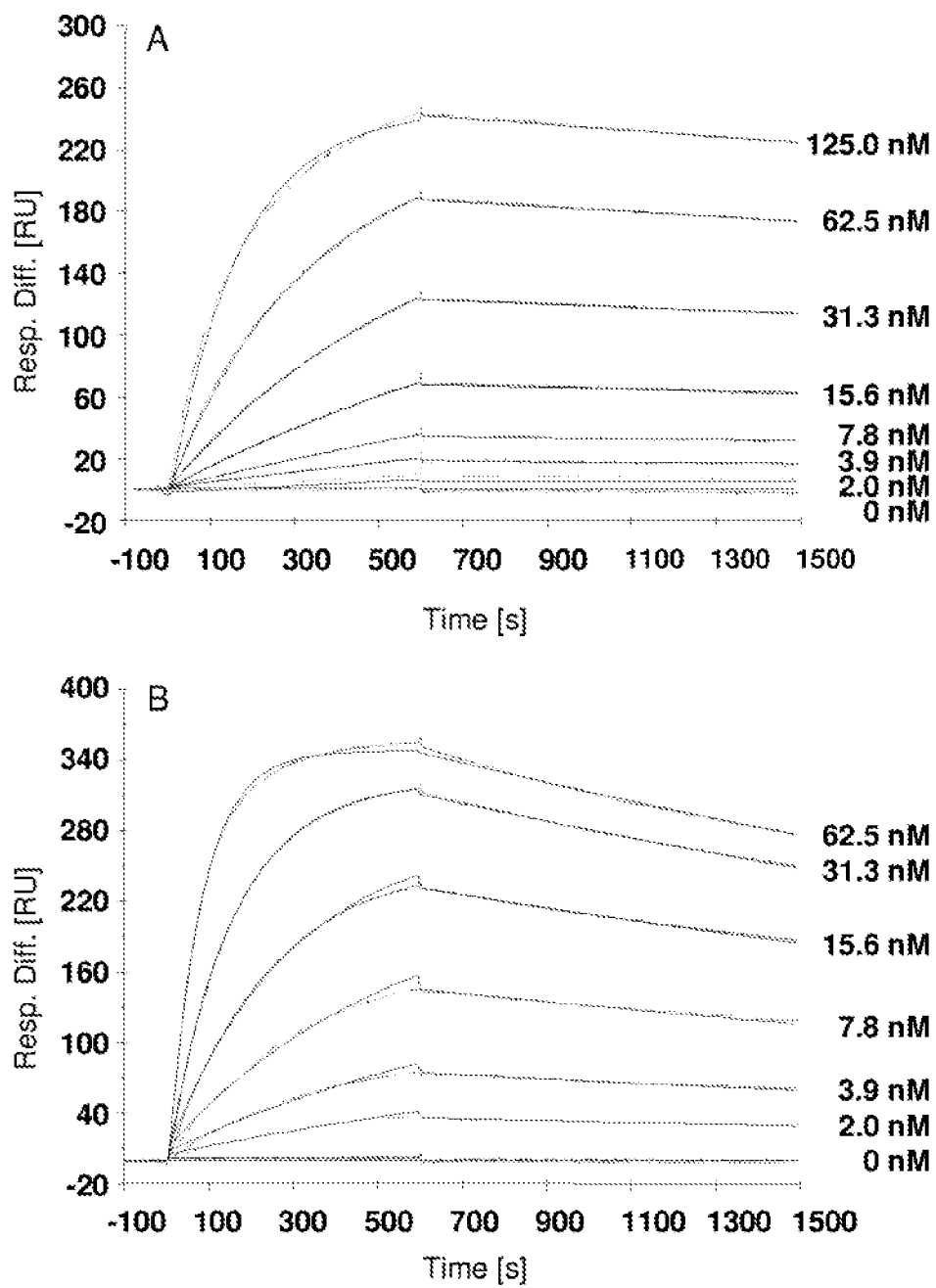

FIG. 8 depicts the kinetic real time analysis of Lcn2 muteins S1-A4 (A) and US7 (B) measured on a Biacore instrument at a flow rate of 10 μl/min. The MBP-Aβ40 fusion protein was coupled via amine chemistry on a CMD 2001 chip (ΔRU=1455) and each of the purified Lcn2 muteins was applied in a series at different concentrations. The measured signal is shown as a grey line whereas the curve fit is depicted as a black line in each case. The k$_{on}$ and k$_{off}$ rates of both muteins differed significantly (k$_{on}$(S1–A4)= 0.48·10$^5$ M$^{-1}$ s$^{-1}$, k$_{on}$(US7)=2.02·10$^5$ M$^{-1}$s$^{-1}$, k$_{off}$(S1–A4)= 8.36·10$^{-5}$ s$^{-1}$, k$_{off}$(US7)=25.2·10$^5$ s$^{-1}$). However, the overall K$_D$ values were quite similar with 1.74 nM for S1-A4 and 1.25 nM for US7.

Figure 9:
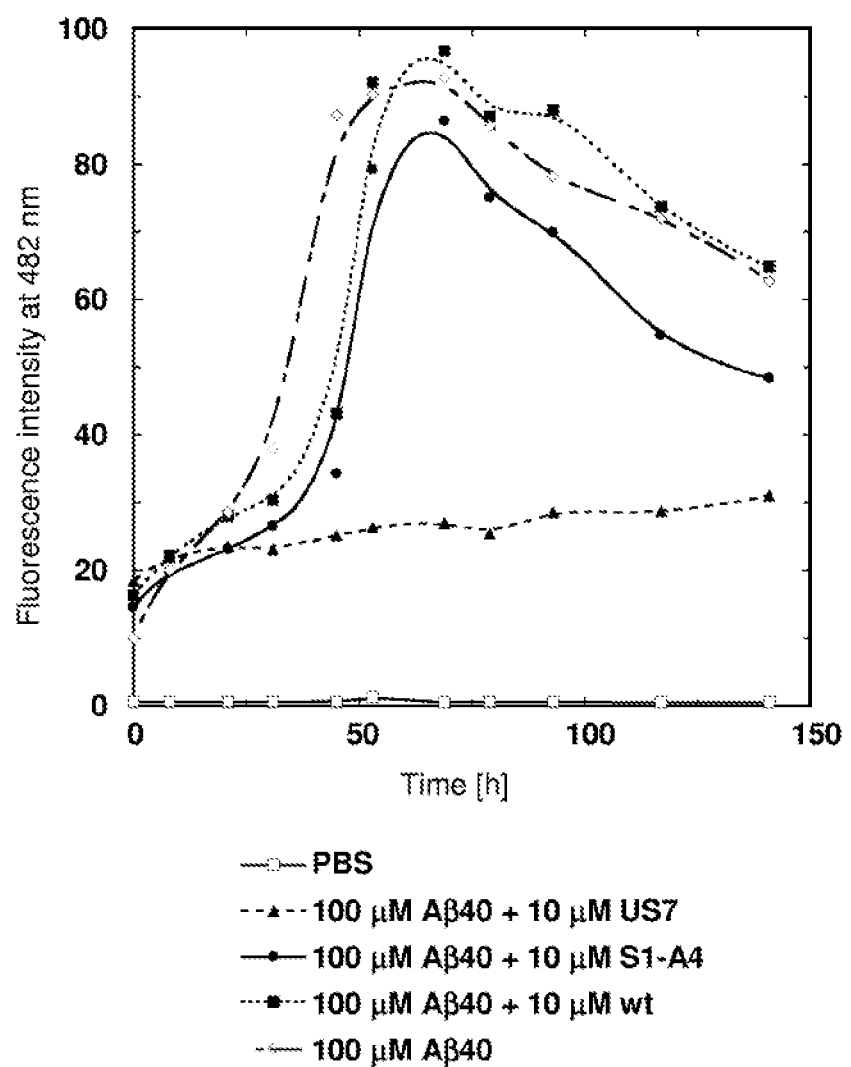

FIG. 9 shows the functional activity of the Lcn2 muteins S1-A4 and US7 tested in a thioflavin T aggregation assay. 100 μM Aβ40 was incubated with 10 μM of US7, S1-A4, wild-type (wt) lipocalin or with PBS at 37° C. without shaking. At indicated time points 20 μl of each sample were mixed with 180 μl of 5 μM thioflavin T and fluorescence was measured with an excitation wavelength of 450 nm and an emission wavelength of 482 nm. The Lcn2 mutein US7 showed potent inhibition of aggregation at a ratio of 1:10 (US7:Aβ40). S1-A4 was not able to significantly inhibit aggregation at this ratio but exerted clear inhibition at a ratio of 1:2 (S1-A4:Aβ40) (not shown). The wild type Lcn2 did not reveal an inhibitory effect on Aβ aggregation.

Figure 10:
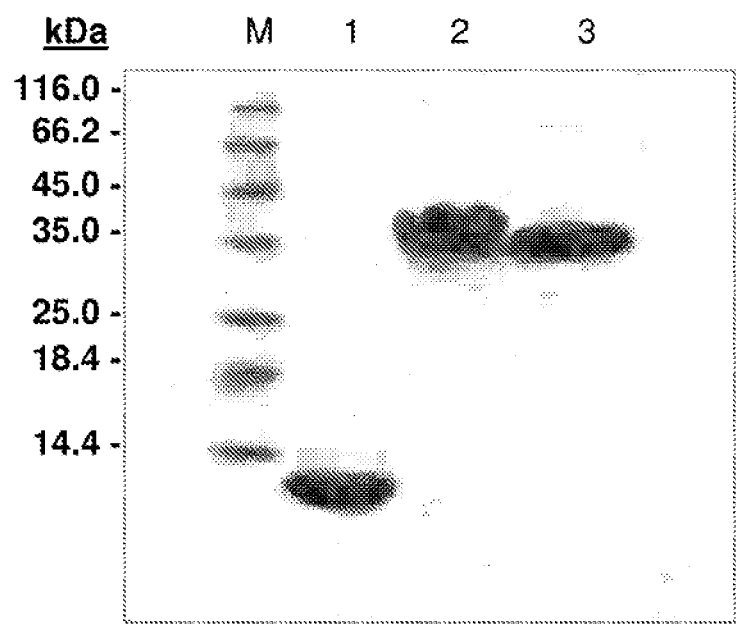

FIG. 10 shows SDS-PAGE analysis, after staining with Coomassie brilliant blue, of recombinant ED-B (lane 1), FN7B8 (lane 2), and FN789 (lane 3) after ion exchange chromatography. All samples were reduced with 2-mercaptoethanol. M: molecular weight marker (Fermentas, St. Leon-Rot, Germany).

Figure 11:
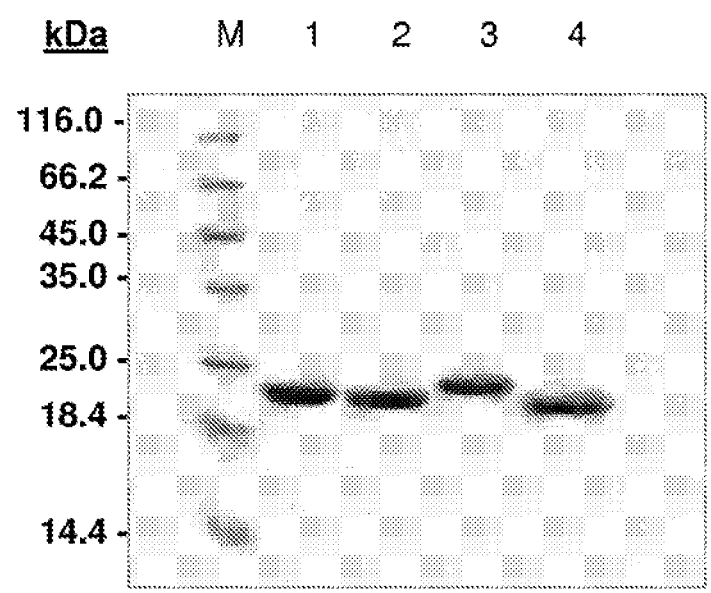

FIG. 11 shows SDS-PAGE analysis, after staining with Coomassie brilliant blue, of Lcn2 muteins N7A (lane 1), N7E (lane 2). N9B (lane 3), and N10D (lane 4) after Strep-tag 11 affinity purification. All samples were reduced with 2-mercaptoethanol. M: molecular weight marker (Fermentas, St. Leon-Rot, Germany).

Figure 12:
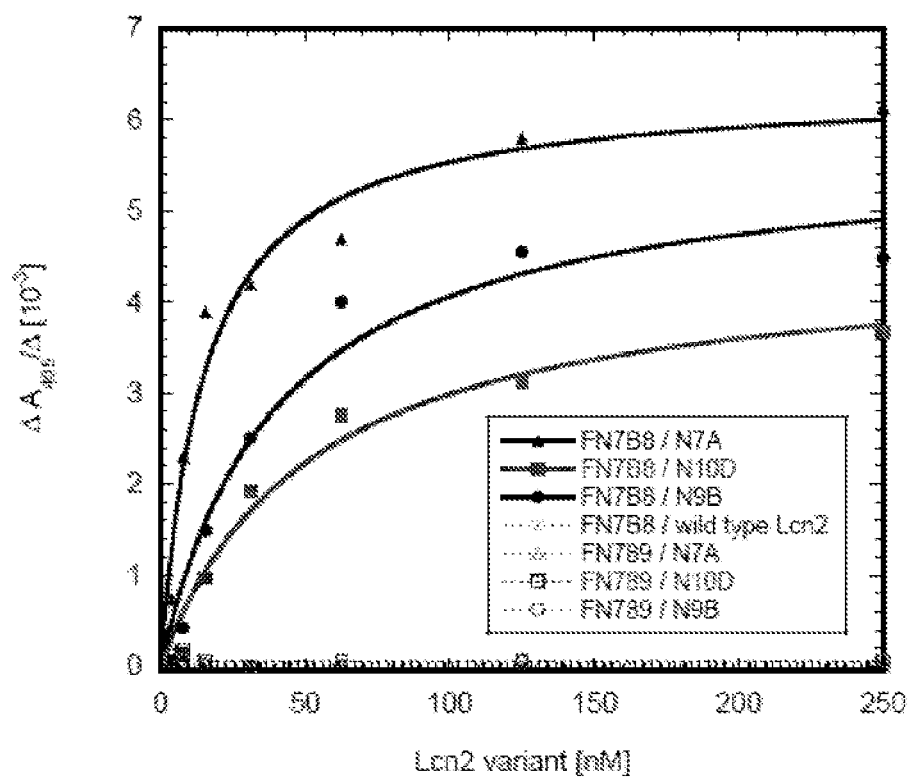

FIG. 12 depicts binding activity in the ELISA. A microtiter plate was coated with the purified proteins FN7B8 and FN789 and incubated with a dilution series of the selected Lcn2 muteins, followed by detection with Streptavidin-alkaline-phosphatase conjugate and pNPP substrate. Recombinant Lcn2 muteins N7A. N9B, and N10D revealed negligible signals in this assay for FN789, which lacked the ED-B and served as a negative control.

Figure 13:
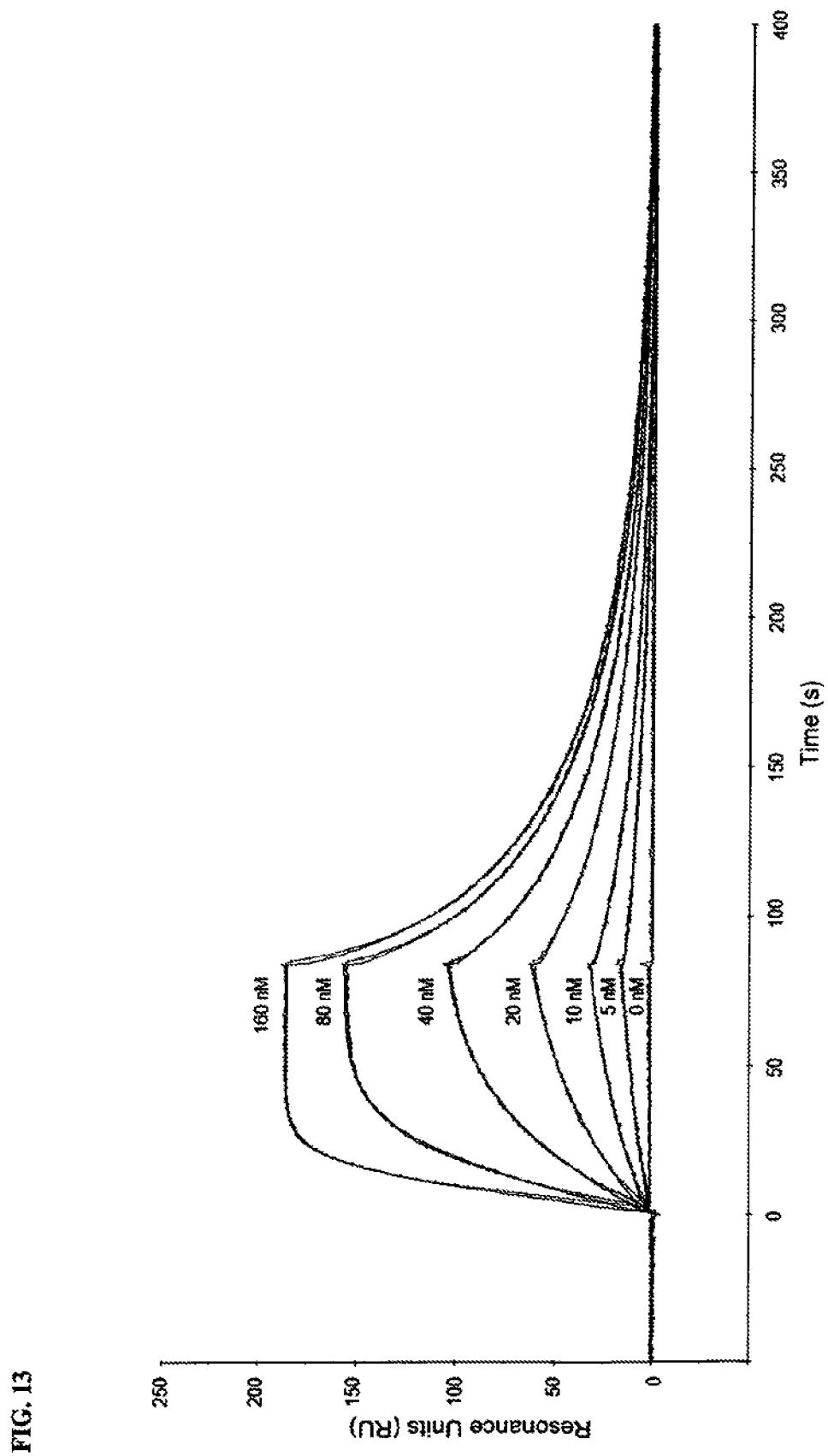

FIG. 13 depicts the kinetic real time analysis of Lcn2 mutein N9B measured on a Biacore instrument. FN7B8 was coupled via amine chemistry to a CMD 200 m sensor chip (ΔRU=500) and the purified Lcn2 mutein was applied at varying concentrations. The measured signal is shown as a grey line whereas the curve fit is depicted as a black line in each case. The kinetic constants determined from this set of curves are listed in Table 2 (Example 17).

Figure 14:
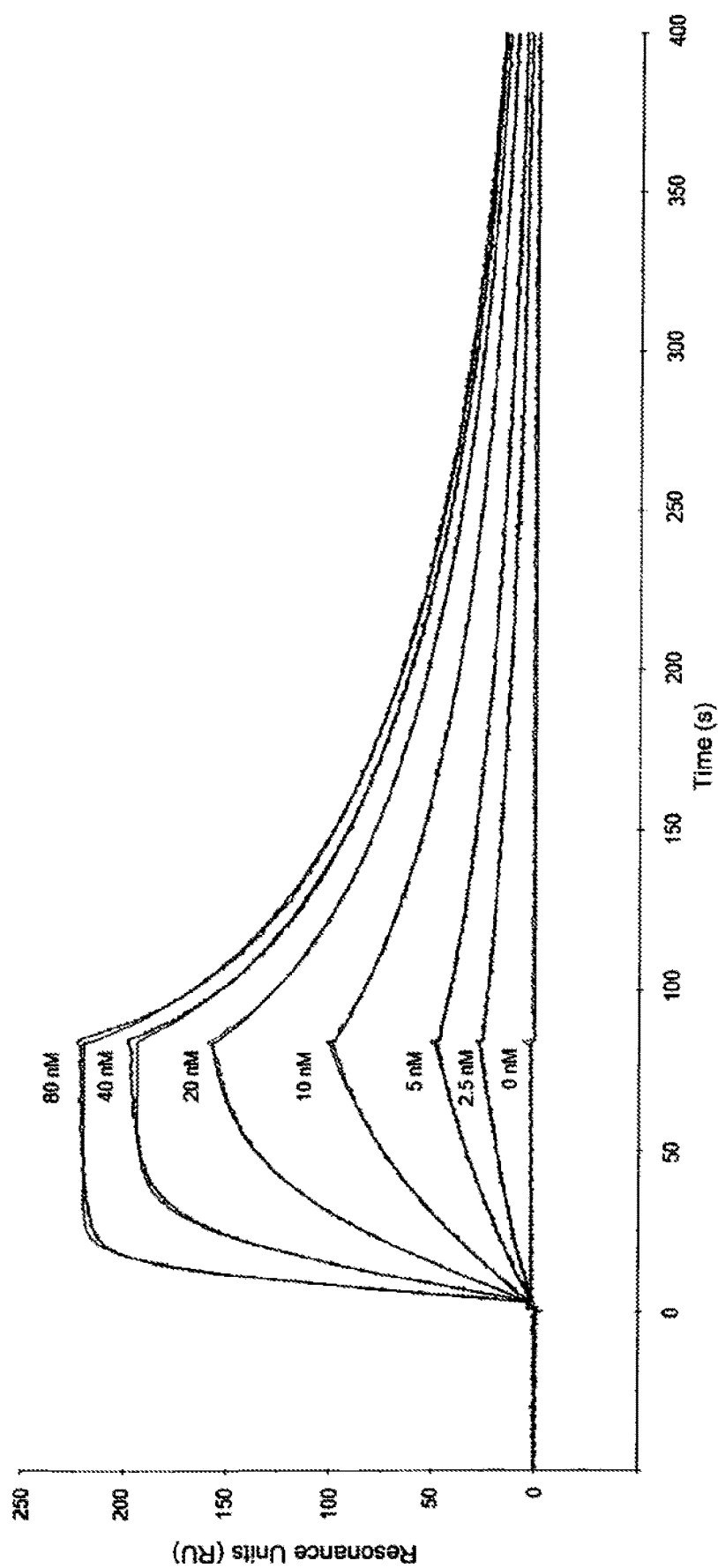

FIG. 14 depicts the kinetic real time analysis of Lcn2 mutein N7E measured on a Biacore instrument. FN7B8 was coupled via amine chemistry to a CMD 200 m sensor chip (ΔRU=500) and the purified Lcn2 mutein was applied at varying concentrations. The measured signal is shown as a grey line whereas the curve fit is depicted as a black line in each case. The kinetic constants determined from this set of curves are listed in Table 2 (Example 17).

Figure 15:
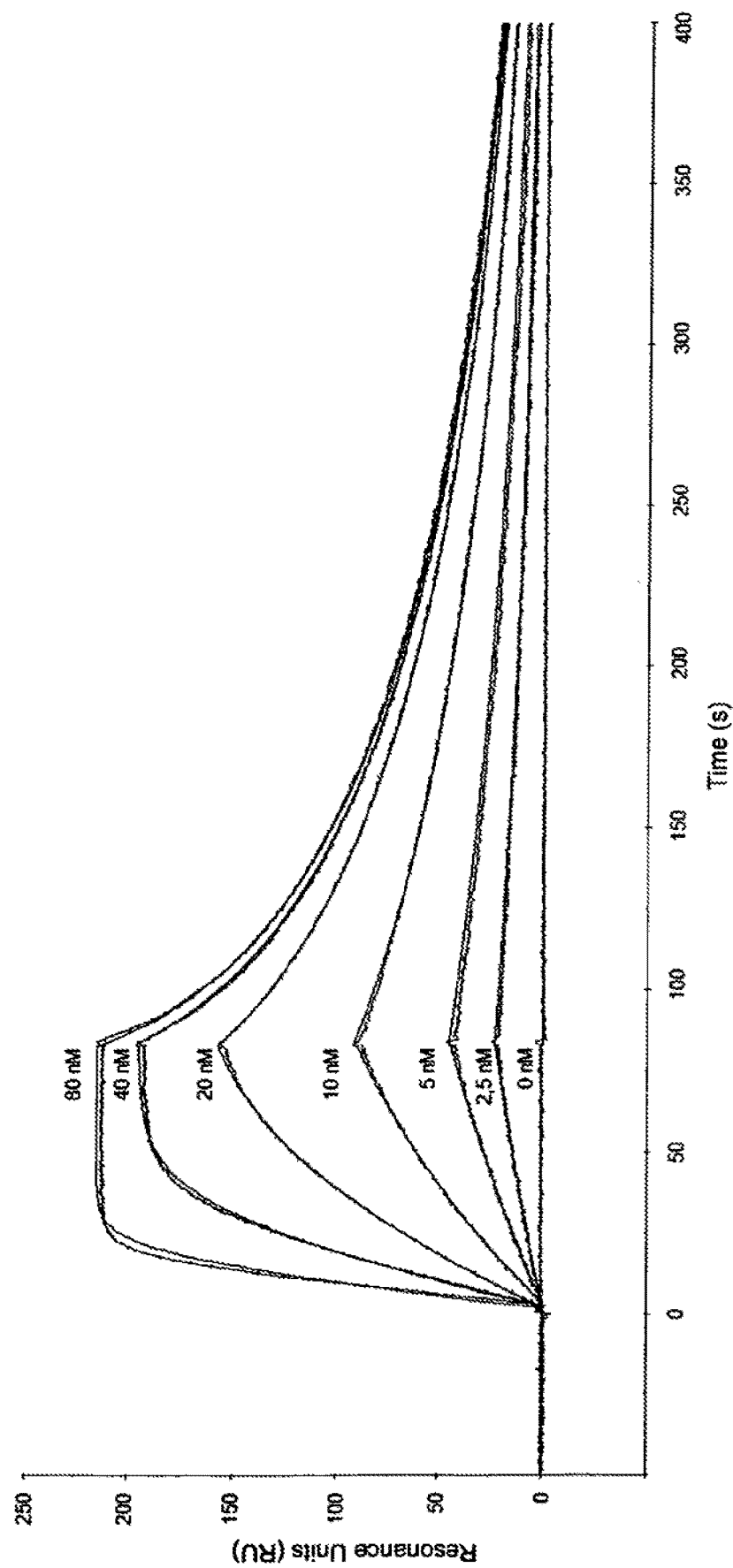

FIG. 15 depicts the kinetic real time analysis of Lcn2 mutein N7A measured on a Biacore instrument. FN7B8 was coupled via amine chemistry to a CMD 200 m sensor chip (ΔRU=500) and the purified Lcn2 mutein was applied at varying concentrations. The measured signal is shown as a grey line whereas the curve fit is depicted as a black line in each case. The kinetic constants determined from this set of curves are listed in Table 2 (Example 17).

Figure 16:
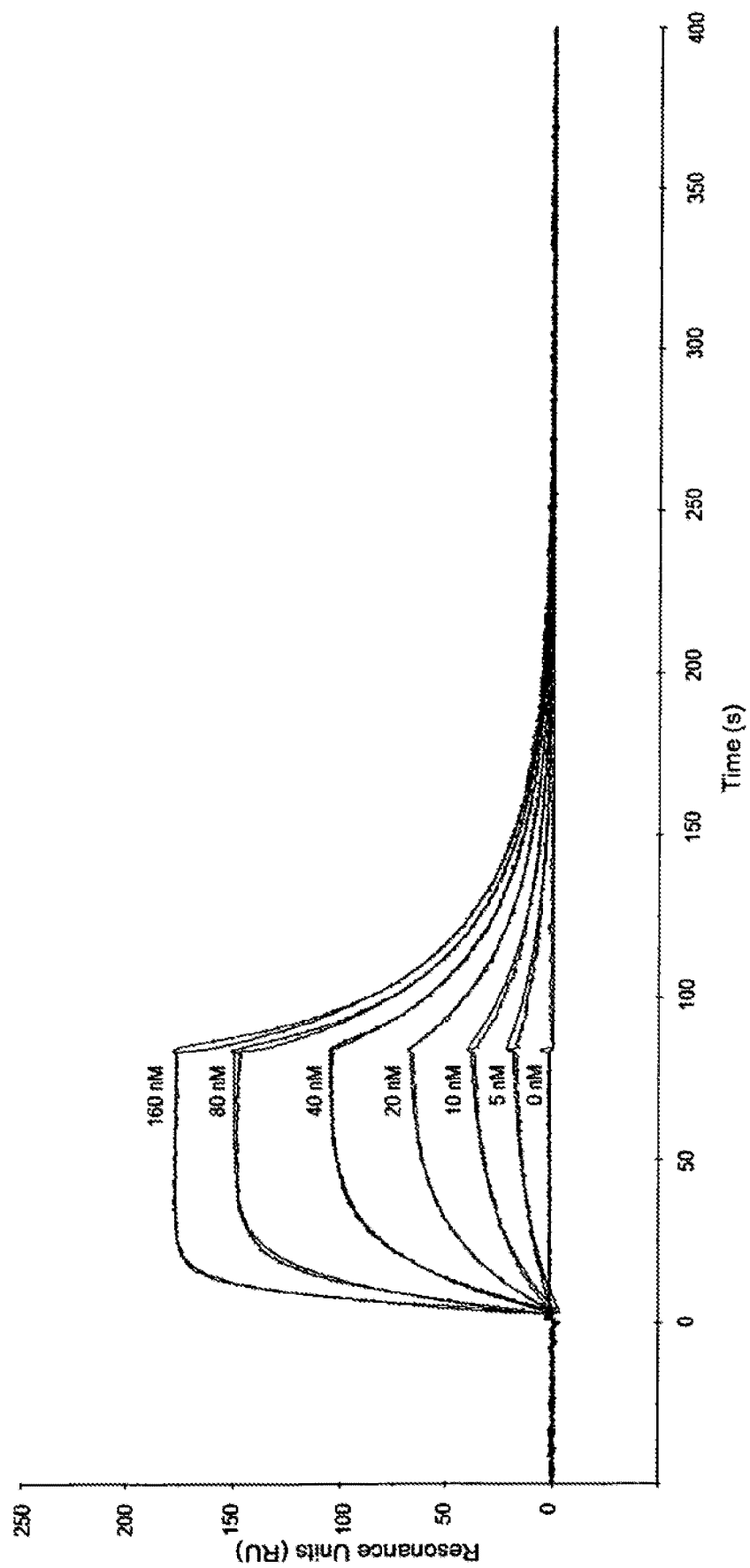

FIG. 16 depicts the kinetic real time analysis of Lcn2 mutein N10D measured on a Biacore instrument. FN7B8 was coupled via amine chemistry to a CMD 200 m sensor chip (ΔRU=500) and the purified Lcn2 mutein was applied at varying concentrations. The measured signal is shown as a grey line whereas the curve fit is depicted as a black line in each case. The kinetic constants determined from this set of curves are listed in Table 2 (Example 17).

FIG. 17 illustrates a sequence alignment of human Lcn2 muteins designated S1-A4 (SEQ ID NO: 39), US-7 (SEQ ID NO: 41), H1-G1 (SEQ ID NO: 43), N7A (SEQ ID NO: 20), N7E (SEQ ID NO: 22), N9B (SEQ ID NO: 24) and N10D (SEQ ID NO: 26) with Lcn2 (SEQ ID NO: 44). The last line below the sequences indicates secondary structural features of the lipocalin (Schönfeld et al. (2009) Proc. Natl. Acad. Sci. USA 106, 8198-8203). FIG. 17 discloses Lib as SEQ ID NO: 67.

FIG. 18 represents an overlay of the SEC elution profiles of the Lcn2 muteins H1GA and H1GV (A), and the analysis of the purified proteins via 15% SDS-PAGE (B). The two Lcn2 muteins H1GA and H1GV were expressed in the periplasm of E. coli JM83 and purified via Strep-tag II affinity chromatography. Both muteins eluted predominantly as monomeric proteins from the Superdex 75 HR 10/30 column with a retention volume of 10 to 11 ml. Peak intensities differed depending on the expression yields of the muteins. (B) shows a 15% SDS-PAGE analysis of recombinant Lcn2 muteins H1-G1, H1GA, and H1GV after Strep-tag II affinity purification and SEC. All three Lcn2 muteins are shown under reduced conditions using 2-mercaptoethanol. M represents the molecular weight marker.

Figure 19:
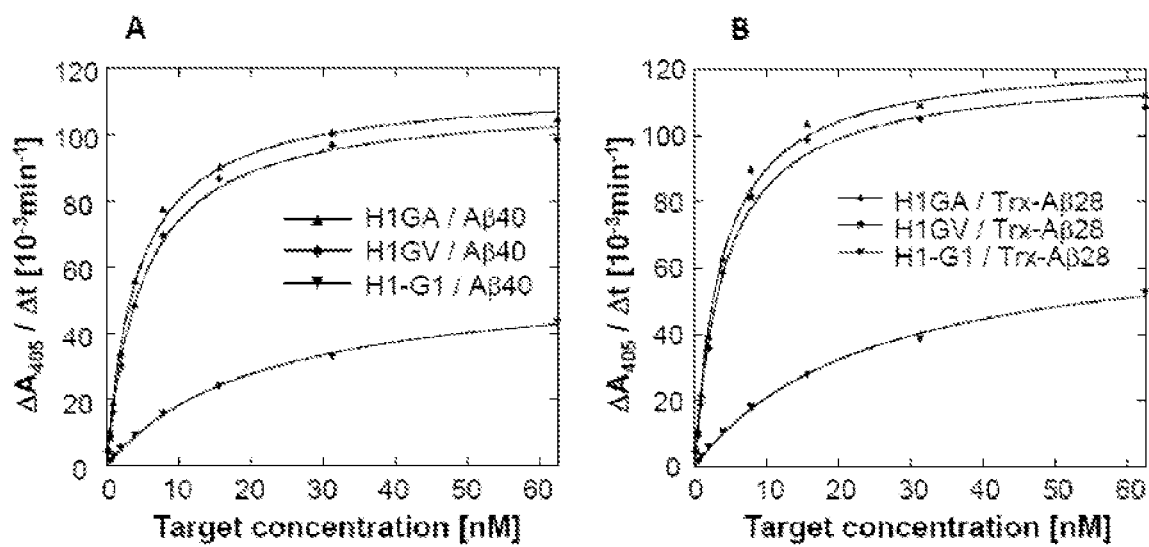

FIG. 19 depicts the binding activity of the Lcn2 muteins H1GA, H1GV, and H1-G1 in capture ELISAs with the biotinylated Aβ targets A40 (A) and Trx-Aβ28 (B). Strep-MAB-Immo was immobilized at 10 μg/ml on microtitre plates and employed for capturing of 1 JAM Lcn2 muteins via the Strep-tag II. Binding of the biotinylated targets, applied in a dilution series, was then detected by incubation with ExtrAvidin/AP and a subsequent chromogenic reaction with pNPP. Biotinylated ovalbumin (Ova) and thioredoxin (Trx) served as negative controls and exhibited no binding to the Lcn2 muteins (not shown). The data were fitted to a monovalent binding model. $K_D$ values determined for Aβ40 were 4.2 nM for H1GA, 4.9 nM for H1GV, and 21.5 nM for H1-G1; corresponding values for Trx-Aβ28 were 3.8 nM, 4.2 nM, and 24.4 nM, respectively.

FIG. 20 depicts the kinetic real time analysis of Lcn2 muteins H1GA (A) and H1GV (B) measured on a Biacore X instrument at a flow rate of 20 μl/min. The MBP-A340 fusion protein was coupled via amine chemistry to a CMD 2001 chip (ΔRU=1316) and each of the purified Lcn2 muteins was applied in a series at varying concentrations. The measured signal is shown as a grey line while the curve fit is depicted as a black line in each case. The kon and koff rates of both muteins were calculated as follows: kon (H1GA)=5.77·10$^4$ M$^{-1}$s$^{-1}$, kon(H1GV)=6.84·10$^4$ M$^{-1}$s$^{-1}$, koff(H1GA)=2.75·10$^{-5}$ s$^{-1}$, koff(H1GV)=7.26·10$^{-5}$ s$^{-1}$. The overall KD values were 0.476 nM for H1GA and 1.06 nM for H1GV.

Figure 21:
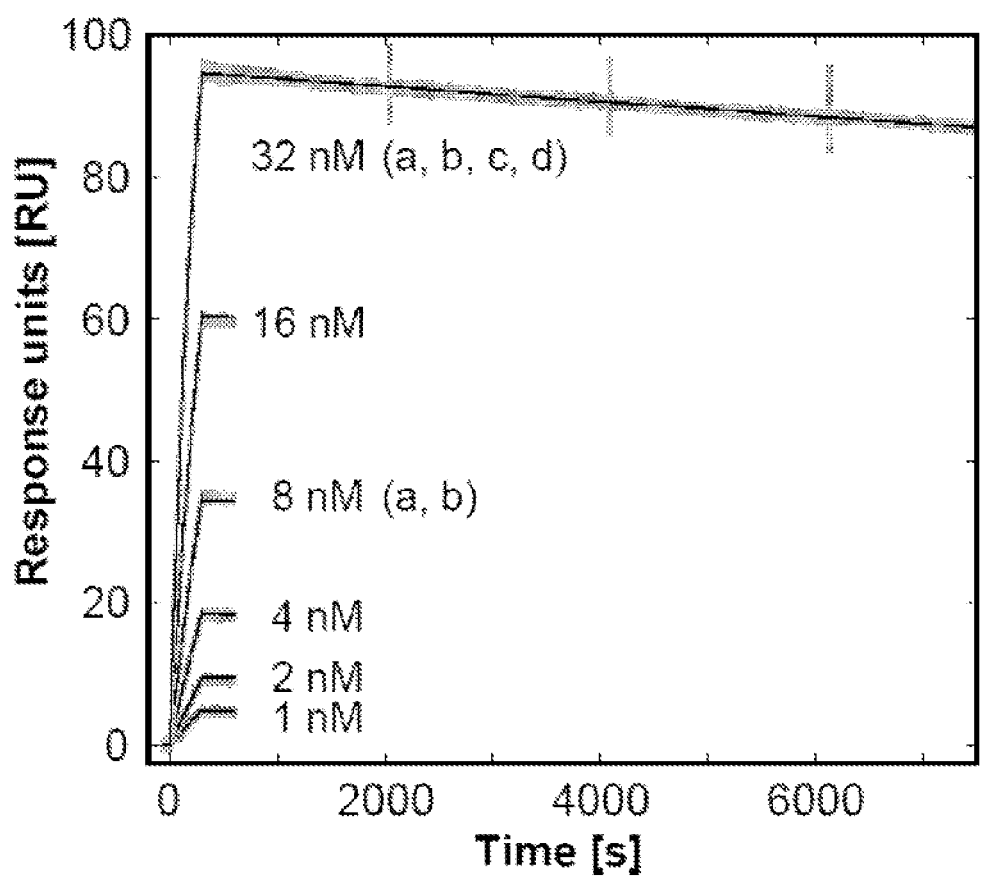

FIG. 21 depicts the kinetic real time analysis of the Lcn2 mutein H1GA measured on a Biacore T100 instrument with immobilized Aβ40 using an extended dissociation time for a trace measured at high concentration. The target peptide Aβ40 was coupled via amine chemistry onto the Biacore CM5 chip (ΔRU=325), and the purified Lcn2 mutein H1GA was applied at a flow rate of 30 μl/min. For exact determination of the low koff rate, dissociation was performed for 7200 s at the highest concentration tested. kon rates were determined using the dilution series of the Lcn2 mutein H1GA with both association and dissociation times of 300 s. The kinetic values for H1GA were determined as follows: kon=1.25·10$^5$ M$^{-1}$s$^{-1}$, koff=1.18·10$^{-5}$ s$^{-1}$, and KD=0.095 nM.

FIG. 22 (A) shows the functional activity of the Lcn2 mutein H1GA tested in a thioflavin T aggregation assay. 500 μl of 1 mg/ml monomeric A3 was incubated in the absence or presence of different molar ratios of Lcn2 mutein H1GA in 0.5×PBS at 37° C. with stirring. Aggregation reactions were prepared in triplicates. For fluorescence measurement 20 μl of a sample taken at periodic intervals was each mixed with 180 μl ThT at a final concentration of 50 μM in 0.5×PBS and analysed at an excitation wavelength of 450 nm and an emission wavelength of 482 nm. The Lcn2 mutein H1GA showed potent inhibition of aggregation at an equimolar ratio. At a subequimolar ratio of 10:2 (Aβ40: H1GA) aggregation was still significantly reduced. (B) In contrast, equimolar amounts of neither BSA nor Lcn2 as negative controls had an inhibitory effect on the aggregation of Aβ40.

FIG. 23 summarizes the KD values determined in the different ELISA setups as well as in surface plasmon resonance measurements for the Lcn2 muteins H1GA and H1GV.

FIG. 24 illustrates a sequence alignment of the Lcn2 muteins S1-A4 (SEQ ID NO: 39), US7 (SEQ ID NO: 41). H1-G1 (SEQ ID NO: 43), H1GA (SEQ ID NO: 50), H1GV (SEQ ID NO: 52). N7A (SEQ ID NO: 20), N7E (SEQ ID NO: 22), N9B (SEQ ID NO: 24), and N10D (SEQ ID NO: 26) with Lcn2 (SEQ ID NO: 44). FIG. 24 discloses Lib as SEQ ID NO: 67

FIG. 25 illustrates a mutual sequence alignment of the muteins H1GA (SEQ ID NO: 50) and H1GV (SEQ ID NO: 52) with their precursor H1-G1 (SEQ ID NO: 43) and the wt Lcn2 (SEQ ID NO: 44)). FIG. 25 discloses Lib as SEQ ID NO: 67.

Figure 26:
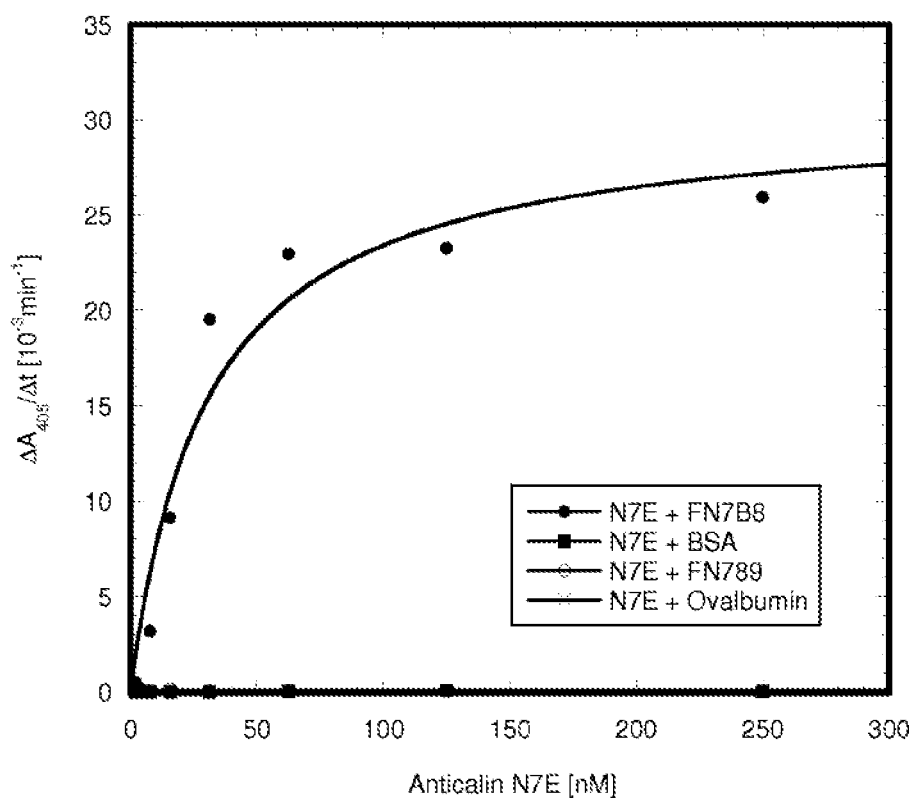

FIG. 26 illustrates specific binding activity of the Lcn2 Variant N7E for FN7B8 in an ELISA. A microtiter plate was coated with FN7B8, FN789, BSA or ovalbumin and incubated with a dilution series of N7E, followed by detection with streptavidin-alkaline-phosphatase conjugate and pNPP substrate. The Lcn2 variant N7E revealed negligible signals in this assay for FN789, BSA and ovalbumin.

FIG. 27 depicts the kinetic real time analysis of Lcn2 variants N7A (A), N7E (B), N9B (C) and N10D (D) measured on a Biacore X instrument. The single fibronectin domain ED-B was coupled via amine chemistry to a CMD 200 m sensor chip (ΔRU=180) and the purified Lcn2 variants were applied at varying concentrations. The measured signals are shown as traces together with the curve fits. The kinetic constants determined from these sensorgrams are listed in Table 3 (Example 24).

FIG. 28 depicts the analytical size exclusion chromatography of Lcn2 variants N7A (A), N10D (B), N9B (C) and N7E (D). Affinity-purified protein was applied to a Superdex S75 10/30 column equilibrated with TBS. The arrows indicate the exclusion volume of the column (6.7 ml). Analytical gel filtration resulted in a prominent peak for each of the four Lcn2 variants. The apparent molecular weight of the proteins was 21.0 kDa for N7A, 21.3 kDa for N10D, 21.7 kDa for N9B and 21.7 kDa for N7E, indicating the presence of only monomeric species.

EXAMPLE 1: CONSTRUCTION OF A MUTANT LCN2 PHAGE DISPLAY LIBRARY

A combinatorial library of Lcn2 variants was generated on the basis of the cloned cDNA (Breustedt et al. (2006) *Biochim. Biophys. Acta* 1764, 161-173), which carried the amino acid substitutions Cys87Ser, to remove the single unpaired thiol side chain (Goetz et al. (2000) *Biochemistry* 39, 1935-1941), as well as Gln28His to introduce a second BstXI restriction site. Mutagenesis and polymerase chain reaction (PCR) assembly of this region was essentially performed according to a published strategy (Beste et al. (1999) *Proc. Natl. Acad. Sci. USA* 96, 1898-1903; Skerra (2001) *J. Biotechnol.* 74, 257-275), this time using a one pot amplification reaction with oligodeoxynucleotides (SEQ ID NO: 1-10 AND 60-61) as illustrated in FIG. 1. Oligodeoxynucleotides were designed such that the primers with SEQ ID NO: 1-4 and 60 corresponded to the coding strand and carried degenerate codons at the amino acid positions 36, 40, 41, 49, 52, or 68, 70, 72, 73, 77, 79, 81, or 96, 100, 103, 106, or 125, 127, 132, 134 respectively, while primers with SEQ ID NO: 5-8 and 61 corresponded to the non-coding strand and did not carry degenerate codons or anticodons. The two flanking primers with SEQ ID NO: 9 and SEQ ID NO: 10 were used in excess and served for the amplification of the assembled randomized gene fragment. All PCR steps were performed using Go-Taq Hot Start DNA polymerase (Promega, Mannheim, Germany) as described (Schlehuber et al. (2000) *J. Mol. Biol.* 297, 1105-1120).

Oligodeoxynucleotides that did not carry degenerate codons were purchased in HPLC grade from Metabion (Munich, Germany). NNK-containing oligodeoxynucleotides were purchased desalted from the same vendor and further purified by urea PAGE. The resulting DNA library was cut with BstXI (Promega, Mannheim, Germany) and cloned on the phagemid vector phNGAL102 (SEQ ID NO:11), which is based on the generic expression vector pASK111 (Vogt and Skerra (2001) *J. Mol. Recognit.* 14 (1), 79-86) and codes for a fusion protein composed of the OmpA signal peptide, the modified mature Lcn2, followed by an amber codon, and the C-terminal fragment of the gene 111 coat protein of the filamentous bacteriophage M13, i.e. similar as previously described for the bilin-binding protein (Beste et al., supra: Skerra, supra). After electroporation of *E. coli* XL1-Blue (Bullock et al. (1987) *Biotechniques* 5, 376-378) with the ligation mixture of 8.4 μg digested PCR product and 94 μg digested plasmid DNA, 1×10$^{10}$ transformants were obtained.

Alternatively, a cloned synthetic Lcn2 random library, which is described in FIG. 2, was obtained from Sloning BioTechnology GmbH (Puchheim, Germany). The central gene cassette flanked by the two BstXI restriction sites was amplified via PCR in 20 cycles using appropriate primers (SEQ ID NO: 9 and SEQ ID NO: 10) and subcloned on phNGAL108 (SEQ ID NO:12) yielding a library with a complexity corresponding to 1.7×10$^{10}$ independent transformants. phNGAL108, which is based on the generic expression vector pASK75 (Skerra (1994) *Gene* 151, 131-135), codes for a fusion protein composed of the OmpA signal peptide, the modified mature Lcn2, the Strep-tag followed by an amber codon, and the full length gene III coat protein of the filamentous bacteriophage M13 (Vogt and Skerra (2004) *ChemBioChem* 5, 191-199).

The following steps in library generation were performed identically for both Lcn2 libraries. 100 ml of the culture, containing the cells which were transformed with the phasmid vectors on the basis of phNGAL102 or phNGAL108, respectively, coding for the library of the lipocalin muteins as phage pIII fusion proteins, were transferred to a sterile Erlenmeyer flask and incubated for one hour at 37° C. 160 rpm in 2YT medium without antibiotic selection pressure. Before infection with VCS-M13 helper phage the culture was diluted in 2YT medium to an OD550 of 0.1 with the corresponding antibiotic added and further grown under identical conditions until an OD550 of 0.6 was reached. After infection with VCS-M13 helper phage (Agilent Technologies. La Jolla. USA) at a multiplicity of infection of approximately 10 the culture was shaken for additional 30 min at 37° C., 100 rpm. Then the incubator temperature was lowered to 26° C. and the shaker speed was increased again to 160 rpm, after 10 min kananmycin (70 μg/ml) was added, followed by induction of gene expression via addition of anhydrotetracycline (ACROS Organics, Geel, Belgium) at 25 μg/l (125 μl of a 200 μg/ml stock solution in dimethylformamide. DMF per liter of culture). Incubation continued for another 12-15 h at 26° C., 160 rpm.

Cells from the complete culture were sedimented by centrifugation (30 min, 18000 g, 4° C.). The supernatant containing the phagemid particles was sterile-filtered (0.45 μm), mixed with ¼ volume 20% w/v PEG 8000, 15% w/v NaCl, and incubated on ice for at least 2 h. After centrifugation (30 min, 18000 g, 4° C.) the precipitated phagemid particles from 1 liter of culture were dissolved in 30 ml of cold BBS/E (200 mM Na-borate, 160 mM NaCl, 1 mM EDTA pH 8.0) containing 50 mM benzamidine (Sigma) and Pefabloc 1 μg/ml (Roth, Karlsruhe. Germany). The solution was incubated on ice for 1 h. After centrifugation of undissolved components (10 min, 43000 g. 4° C.) each supernatant was transferred to a new reaction vessel.

Addition of ¼ volume 20% w/v PEG 8000, 15% w/v NaCl and incubation for 60 min on ice served to reprecipitate the phagemid particles until the phagemids were aliquoted and frozen at −80° C. for storage. For the first selection cycle phagemids were thawed and centrifuged (30 min, 34000 g, 4° C.), the supernatant was removed, and the precipitated phagemid particles were dissolved and combined in a total of 400 μl PBS containing 50 mM benzamidine. After incubation for 30 min on ice the solution was centrifuged (5 min, 18500 g, 4° C.) in order to remove residual aggregates and the supernatant was used directly for the phage display selection.

EXAMPLE 2: PREPARATION OF AD TARGETS IN DIFFERENT FORMATS

Aβ40 peptide (SEQ ID NO: 29), corresponding to amino acids 1 to 40 of the mature beta-amyloid sequence (Dodel et al. (2003) *Lance Neurology* 2, 215-220), was purchased as synthetic, lyophilized peptide either with a C-terminal biotin group attached via a lysine spacer (Peptide Speciality Laboratory, Heidelberg, Germany) or in a non-labeled form (W. M. Keck Laboratory, New Haven, USA). Homogeneously monomeric A340 was obtained by dissolving up to 5 mg of the peptide in 0.5 mL of 1,1,1,3,3,3-hexafluoro-2-propanol (HFIP; Sigma-Aldrich, Steinheim, Germany) at room temperature for at least 0.5 h. Subsequently, HFIP was evaporated in a SpeedVac concentrator, and A040 was dissolved in a suitable volume of distilled $H_2O$ followed by sonication (Bandelin, Sonorex, RK100, Germany) in cold water for 15 min. After filtration with a 0.22 μm filter (Spin-X Centrifuge Tube Filter; Corning, USA), protein concentration was determined by absorption measurement at 280 nm using the calculated extinction coefficient of 1490 $M^{-1}cm^{-1}$ (Gasteiger et al. (2003) ExPASy: the proteomics server for in-depth protein knowledge and analysis. *Nucleic Acids Res.* 31, 3784-3788, http://www.expasy.ch/tools/protparam.html).

Shorter versions of the beta-amyloid peptide, such as the N-terminal peptide Aβ1-11 (SEQ ID NO: 30) and the central peptide Aβ16-27 (SEQ ID NO: 31), were also purchased from the Peptide Speciality Laboratory. These shorter versions were dissolved straight in the buffer of choice without previous HFIP treatment.

In addition to the synthetic peptides, two vectors encoding different recombinant Aβ fusion proteins were constructed for the purpose of bacterial expression: First, a fusion protein with the maltose binding protein (MBP, pMBP-His, SEQ ID NO: 32) was constructed according to Hortschansky et al. ((2005) *Protein Sci.* 14, 1753-1759) resulting in pASK75-MBP-Abeta40 (SEQ ID NO: 33). Second, pASK75-TrxAbeta28H6 (SEQ ID NO: 34), in which amino acids 1 to 28 of the mature amyloid peptide were inserted into the active site loop of thioredoxin (Trx, pASK75-TrxH6, SEQ ID NO: 35), was constructed according to Moretto et al. ((2007) *J. Biol. Chem.* 282, 11436-11445).

Sequential cloning of human Aβ40 carrying an extended N-terminus in frame with the gene of the maltose binding protein yielded the new plasmid pASK75-MBP-A340 a derivative of the vector pASK75 (Skerra (1994) *Gene* 151, 131-135). This vector encodes a fusion protein of the maltose binding protein followed by a $His_6$-tag (SEQ ID NO: 54) for facile protein purification, a tobacco etch virus (TEV) recognition site for cleavage of the fusion protein as well as the sequence of human Aβ40. The vector is under tight control of the tetracycline promoter/operator system and allows expression of the fusion proteins in high yields in the cytoplasm of *E. coli*.

The sequence coding for amino acid 1 to 28 of the mature amyloid peptide (Aβ28) was inserted into the thioredoxin loop via a unique CpoI site in the active site loop of thioredoxin (nucleotide position 99-105, corresponding to amino acid residues 34 and 35) yielding the vector pASK75-Trx-Abeta28H6.

Both Aβ fusion proteins, Trx-Aβ28 and MBP-Aβ40, as well as the unfused control proteins Trx and MBP were expressed in *E. coli* JM83 (Yanisch-Perron et al. (1985) *Gene* 33, 103-119) at 37° C. Protein expression was induced at an optical density $OD_{550}$ of 0.5 by adding 200 μg/l anhydrotetracycline (aTc; Acros, Geel, Belgium) dissolved in water-free dimethylformamide (DMF: Sigma-Aldrich, Steinheim. Germany) and continuing incubation with agitation for 3 h. Cells were harvested by centrifugation at 4200 g at 4° C. for 20 min. The cell pellets from a 2 L culture were resuspended in 20 ml lysis buffer (100 mM Tris/HCl pH 8.0, 50 mM NaCl, 1 mM EDTA) and the resulting suspension was homogenized by three passages through a French Pressure Cell. Insoluble material was removed by centrifugation (34500 g, 4° C., 20 min), the supernatant was filtered with a 0.45 μm filter (Filtropur S 0.45; Sarstedt, Nuembrecht, Germany) and used for affinity purification via the $His_6$-tag (SEQ ID NO: 54) of each protein. After immobilized metal affinity chromatography (IMAC) the fusion proteins were further purified via size exclusion chromatography (SEC).

Protein concentrations were determined by absorption measurement at 280 nm using calculated extinction coefficients of 66350 $M^{-1}cm^{-1}$ for MBP (SEQ ID NO: 32) 69330 $M^{-1}cm^{-1}$ for MBP-Aβ40 (SEQ ID NO: 33). 15470 $M^{-1}cm^{-1}$ for Trx-Aβ28 (SEQ ID NO: 34), and 13980 $M^{-1}cm^{-1}$ for Trx (SEQ ID NO: 35) (Gasteiger et al., supra).

For the following experiments both Aβ fusion proteins, Trx-A328 and MBP-A340, as well as ovalbumin (Ova Sigma-Aldrich, Steinheim, Germany), Trx, and MBP, which served as control proteins, were labeled with either biotin or digoxigenin (DIG) at a molar ratio of 2:1 (labelling reagent: target protein).

To this end. D-biotinoyl-ε-aminocaproic acid-N-hydroxysuccinimide ester (Roche Diagnostics, Mannheim, Germany) or digoxigenin-3-O-methylcarbonyl-ε-aminocaproic acid-N-hydroxysuccinimide ester (Roche Diagnostics, Mannheim, Germany) dissolved in water-free dimethylformamide (DMF; Sigma-Aldrich, Steinheim. Germany) or dimethylsulfoxide (DMSO; Sigma-Aldrich, Steinheim, Germany) was added in a 2-fold molar ratio to the protein in PBS (4 mM $KH_2PO_4$, 16 mM $Na_2HPO_4$, 115 mM NaCl, pH 7.4). The mixture was rotated for 1 h at room temperature. Then, 1 M Tris/HCl pH 8.0 was added to a final concentration of 10 mM and incubated for 10 min to saturate remaining active NHS ester groups, and the labeled proteins were purified via SEC on a Superdex 75 HR 10/30 column (Amersham-Pharmacia. Freiburg, Germany). To be used as target in phage display selection, Trx-Aβ28 was first labeled with digoxigenin for 1 h, then—to block any unpaired Cys residues—a 50-fold molar excess of iodoacetamide (Sigma-Aldrich, Steinheim, Germany) was added, followed by incubation for 1 h. Subsequently, the modified protein was treated with 1 M Tris/HCl pH 8.0 and purified as above.

EXAMPLE 3: SELECTION OF LCN2 MUTEINS WITH AFFINITY TO THE Aβ40 PEPTIDE BY PHAGE DISPLAY

For each panning cycle about $10^{12}$ recombinant phagemids in PBS (4 mM $KH_2PO_4$, 16 mM $Na_2HPO_4$, 115 mM NaCl, pH 7.4) were blocked with 2% (w/v) BSA in PBS/T (PBS containing 0.1% (v/v) Tween 20 [polyoxyethylene sorbitan monolaurate; AppliChem, Darmstadt, Germany]) for 1 h. Portions of 50 and of 25 μL of Streptavidin-coated magnetic bead suspension (Dynabeads M-280 Streptavidin; Dynal Biotech, Invitrogen, Karlsruhe, Germany and Streptavidin Magnetic Particles; Roche Diagnostics, Mannheim. Germany) were separately washed with PBS/T and blocked with 2% (w/v) BSA in PBS/T for 1 h. The 25 μL of blocked beads were used for preadsorption of the blocked phagemids to remove phagemids specific for the beads, the 50 μL were used later for the selection cycle.

The blocked phagemids were incubated for 30 min with the 25 μL washed and blocked Streptavidin-coated magnetic beads. The beads were then pulled down with a single tube magnetic stand (Promega, Mannheim, Germany) for 2 min, and the supernatant containing phagemids not bound to the beads was incubated for 1-2 h with 100 nM biotinylated A0340 from Example 2 in a total volume of 400 μL. The mixture of phagemids and peptide target was then incubated for 0.5 h with the 50 μL blocked beads and subsequently pulled down with a single tube magnetic stand for 2 min. The supernatant containing unbound phagemids was discarded. The target/phagemid complexes bound to magnetic beads were washed 10 times with 400 μL PBS/T, and then bound phagemids were eluted under rotation for 10 min with 350 μL 0.1 M glycine/HCl, pH 2.2, followed by immediate neutralization with 55 μL 0.5 M Tris base. Alternatively, elution was performed under denaturing conditions with 400 μL 4 M urea in PBS for 30 min, followed by dilution with 1 mL PBS. Elution under denaturing conditions with either acid or urea was applied for selection cycles 1 and 2 whereas for cycles 3 and 4 elution was performed under conditions of competition by adding 400 μL 100 μM non-biotinylated Aβ40 to the beads with the bound phagemids and rotation for 1 h. In total, 4 selection cycles were performed.

For amplification of eluted phagemids an exponentially growing culture of $E.\ coli$ XL-1 Blue was infected for 30 min at 37° C. Remaining bead-bound phagemids were eluted by addition of $E.\ coli$ XL-1 Blue in the exponential growth phase directly to the beads. After centrifugation at 4° C. the bacterial pellet was resuspended in a suitable volume of 2×YT medium (16 g/L Bacto Tryptone, 10 g/L Bacto Yeast Extract, 5 g/L NaCl, pH 7.5), plated onto LB-Cam plates (10 g/L Bacto Tryptone, 5 g/L Bacto Yeast Extract, 5 g/L NaCl, 15 g/L Bacto Agar, 35 mg/L chloramphenicol, pH 7.5), and incubated for 14-16 h at 32° C. Cells were then scraped off the plates and employed for rescue and reamplification of the recombinant phagemids.

Screening of the enriched phagemid pools was performed by a screening ELISA (Example 5) after the fourth panning step.

EXAMPLE 4: SELECTION OF LCN2 MUTEINS WITH AFFINITY TO THE TRX-A1328 FUSION PROTEIN BY PHAGE DISPLAY

For each panning cycle about $10^{12}$ recombinant phagemids in PBS (4 mM $KH_2PO_4$, 16 mM $Na_2HPO_4$, 115 mM NaCl, pH 7.4) were first blocked for 1 h with 2% (w/v) BSA in PBS/T (PBS containing 0.1% (v/v) Tween 20) for cycles 1 and 2. From selection cycle 3 onwards, 2% (w/v) skim milk (Sucofin, TSI, Zeven, Germany) in PBS/T was used as blocking reagent. 50 and 25 μL anti-DIG-IgG coated magnetic bead suspension (Europa Bioproducts Ltd, Cambridge, UK) were washed with PBS/T, and separately blocked for 1 h with 2% (w/v) BSA in PBS/T or skim milk.

The blocked phagemids were incubated for 30 min with the washed and blocked 25 μL anti-DIG-IgG coated magnetic beads. The beads were then pulled down with a single tube magnetic stand (Promega, Mannheim, Germany) for 2 min, and the supernatant containing phagemids not bound to the beads was incubated for 30 min with 15 μM non-labeled Trx from Example 2 to remove phagemids specific for Trx. Digoxigenated and carboxymethylated Trx-Aβ28 from Example 2 was then added to a final concentration of 100 nM, and the mixture was incubated for 1-2 h in a total volume of 400 μL. The mixture of phagemids, Trx, and Trx-Aβ28 was then incubated with the drained blocked beads from the 50 μL portion for 0.5 h. The beads were then pulled down with a single tube magnetic stand for 2 min. The supernatant containing unbound phagemids was discarded. The magnetic beads with the bound phagemids were washed 10 times with 500 μL PBS/T. Subsequently, bound phagemids were eluted under rotation for 30 min in 400 μl 4 M urea in PBS, followed by dilution with 1 mL PBS. In total, 6 selection cycles were performed.

For amplification of eluted phagemids an exponentially growing culture of $E.\ coli$ XL-1 Blue was infected for 30 min at 37° C. Remaining bead-bound phagemids were eluted by addition of $E.\ coli$ XL-1 Blue in the exponential growth phase directly to the beads. After centrifugation at 4° C. the bacterial pellet was resuspended in a suitable volume of 2×YT medium (16 g/L Bacto Tryptone, 10 g/L Bacto Yeast Extract, 5 g/L NaCl, pH 7.5), plated onto LB-Cam plates (10 g/L Bacto Tryptone. 5 g/L Bacto Yeast Extract, 5 g/L NaCl, 15 g/L Bacto Agar, 35 mg/L chloramphenicol, pH 7.5), and incubated for 14-16 h at 32° C. Cells were then scraped off the plates and employed for rescue and reamplification of the recombinant phagemids.

Screening of the enriched phagemid pools was performed by a filter-sandwich colony screening assay (Example 6) after the sixth panning step.

EXAMPLE 5: IDENTIFICATION OF LCN2 MUTEINS SPECIFIC FOR Aβ VIA SCREENING ELISA

After four cycles of phagemid selection with A040 as described in Example 3, the enriched pool of Lcn2 muteins was subcloned on phNGAL98 (SEQ ID NO: 27), used for transformation of the $E.\ coli$ supE strain TG1-F⁻ (a derivative of $E.\ coli$ K12 TG1 (Kim et al. (2009) $J.\ Am.\ Chem.\ Soc.$ 131, 3565-3576), and subjected to screening ELISA.

For this purpose, single colonies from the enriched pool were grown in 96-well plates (Multiple Well Plate 96 round bottom with lid; Sarstedt, Nuembrecht, Germany) in 100 μL TB-Amp medium (12 g/L Bacto Tryptone, 24 g/L Bacto Yeast Extract, 55 mM glycerol, 17 mM $KH_2PO_4$, 72 mM $K_2HPO_4$, 100 mg/L ampicillin) at 37° C. over night. A new plate with 100 μL TB-Amp medium was inoculated with the overnight cultures, and grown to exponential phase at 22° C. or 37° C. Periplasmic expression of Lcn2 muteins was induced with 20 μL 0.2 μg/mL anhydrotetracycline (aTc; Acros. Geel, Belgium) dissolved in water-free dimethylformamide (DMF; Sigma-Aldrich, Steinheim. Germany) for 13-17 h at 20° C. Periplasmic proteins were released with 40 μL BBS (800 mM Na-borate, 640 mM NaCl, 8 mM EDTA, pH 8.0) including 1 mg/mL lysozyme by incubation for 1 h at 4° C. and agitation at 750 rpm (Thermomixer Comfort, Eppendorf, Hamburg, Germany). After blocking with 40 μL 10% (w/v) BSA in PBS/T (4 mM $KH_2PO_4$, 16 mM $Na_2HPO_4$, 115 mM NaCl, pH 7.4 with 0.05% (v/v) Tween 20) for 1 h at 4° C. and 750 rpm the plates were centrifuged for 10 min at 4° C. and 3000 g. The supernatant was used for ELISA.

For selective capturing of the Lcn2 muteins carrying the C-terminal Strep-tag 11 (Schmidt and Skerra (2007) $Nat.\ Protoc.$ 2, 1528-1535), a 96-well MaxiSorp polystyrene microtitre plate (Nunc, Langenselbold, Germany) was coated with 10 μg/mL StrepMAB-Immo (IBA, Göttingen, Germany) in PBS over night at 4° C. and blocked with 3% (w/v) BSA in PBS/T (PBS with 0.1% (v/v) Tween 20) at room temperature for 1 h. After 3 washing steps with PBS/T, 120 μL of the cell extract from above was applied per well and incubated for 1.5 h at 300 rpm. After washing, biotinylated Aβ40 from Example 2 was added at a concentration of 0.5 μM and incubated for 1 h. As a control, biotinylated Ova instead of Aβ40 was used. The wells were washed again, and bound biotinylated peptide or protein was detected with 50 μL of ExtrAvidin/AP conjugate (Sigma-Aldrich, Steinheim, Germany) diluted 1:5000 in PBS/T for 1 h, followed by signal development in the presence of 100 μL 0.5 mg/mL p-nitrophenyl phosphate (AppliChem, Darmstadt, Germany) in 100 mM Tris/HCl, pH 8.8, 100 mM NaCl, 5 mM $MgCl_2$ for up to 1 h. Absorption at 405 nm was measured in a SpectraMax 250 reader (Molecular Devices, Sunnyvale, USA).

Alternatively, 0.5 μM non-biotinylated Aβ40 from Example 2 was directly immobilized onto a 96-well MaxiSorp polystyrene microtitre plate (Nunc, Langenselbold, Germany), followed by blocking. After incubation with the cell extract from above and washing, bound Lcn2 muteins were detected via the Strep-tag II using a 1:1500 dilution of Streptactin/AP conjugate (IBA, Göttingen, Germany). As a control, 0.5 μM Ova was immobilized onto the ELISA plate.

EXAMPLE 6: IDENTIFICATION OF LCN2 MUTEINS SPECIFIC FOR TRX-Aβ28 VIA FILTER-SANDWICH COLONY SCREENING ASSAY

After six cycles of phagemid selection with Trx-Aβ28 as described in Example 4, the mutagenized Lcn2 gene cassette was subcloned via BstXI (Fermentas, St. Leon-Rot, Germany) on the plasmid phNGAL124 (SEQ ID NO: 42), which encodes a fusion of the OmpA signal peptide, the Lcn2-coding region with the C-terminal Strep-tag II (Schmidt and Skerra (2007) Nat. Protoc. 2, 1528-1535) followed by an amber stop codon as well as a gene for the albumin-binding domain (ABD) from streptococcal protein G (Schlehuber et al. (2000) J. Mol. Biol. 297, 1105-1120).

Then, a filter-sandwich colony screening assay was performed, whereby the Lcn2-ABD fusion proteins were released from the colonies plated on a hydrophilic filter membrane (PVDF type GVWP, 0.22 μm; Millipore, Schwalbach, Germany) and functionally captured on an underlying second membrane (Immobilon-P membrane, 0.45 μm: Millipore, Schwalbach, Germany) coated with human serum albumin (HSA, Sigma-Aldrich, Steinheim. Germany) following a procedure described in detail by Schlehuber et al. ((2000) J. Mol. Biol. 297, 1105-1120). This membrane was probed with 100 nM of DIG-labeled Trx-Aβ28 from Example 2 in PBS/T for 1 h. The bound target conjugate was detected with an anti-DIG Fab/alkaline phosphatase (AP) conjugate (Roche Diagnostics, Mannheim. Germany) followed by a chromogenic reaction with 5-bromo-4-chloro-3-indolyl phosphate, 4-toluidine salt (BCIP: AppliChem, Darmstadt, Germany) and nitro blue tetrazolium (NBT; AppliChem, Darmstadt, Germany). Having identified spots with intense colour signals on this membrane, the corresponding colonies were picked from the first filter and propagated for side by side comparison in a secondary colony screen.

For this purpose isolated bacteria as well as bacteria expressing control Lcn2 muteins, such as the wild-type lipocalin, were stippled onto a fresh hydrophilic membrane and grown until small colonies became visible. Binding was tested both for the DIG-labeled Trx-Aβ28 as well as for the DIG-labeled control proteins Trx and Ova. Lcn2 muteins that gave rise to specific signals for the Trx-Aβ28 target in this secondary screen were further propagated for plasmid isolation and subsequent sequence analysis.

EXAMPLE 7: SOLUBLE PRODUCTION AND PURIFICATION OF LCN2 MUTEINS SPECIFIC FOR Aβ AND ED-B

The recombinant Lcn2 and its muteins were produced by periplasmic secretion in E. coli BL21 (Studier and Moffat (1986) J. Mol. Biol. 189, 113-130), E. coli W3110 (Bachmann (1990) Microbiol. Rev. 54, 130-197), E. coli JM83 (Yanisch-Perron et al. (1985) Gene 33, 103-119) or the E. coli supE strain TG1-F⁻ (a derivative of E. coli K12 TG1 [Kim et al. (2009) J. Am. Chem. Soc. 131, 3565-3576] that was cured from its episome using acridinium orange). For soluble protein expression the plasmid phNGAL98 (SEQ ID NO: 27) was used, encoding a fusion of the OmpA signal peptide with the mature Lcn2 protein (SEQ ID NO: 28) and the C-terminal Strep-tag II, whereby the plasmid carries the two non-compatible BstXI restriction sites for unidirectional subcloning of the mutated gene cassette.

The soluble protein was affinity-purified by means of the Strep-tag II (Schmidt and Skerra (2007) Nat. Protoc. 2, 1528-1535), followed by size exclusion chromatography (SEC) on a Superdex 75 HR 10/30 column (Amersham-Pharmacia. Freiburg, Germany) using PBS buffer. Protein purity was checked by SDS-PAGE (Fling and Gregerson (1986) Anal. Biochem. 155, 83-88). Protein concentrations were determined by absorption measurement at 280 nm using calculated extinction coefficients of 31400 $M^{-1}cm^{-1}$ for wt Lcn2 (SEQ ID NO: 44) and of 26930 $M^{-1}$ $cm^{-1}$ for the Aβ specific muteins H1-G1 (SEQ ID NO: 43), 24410 $M^{-1}cm^{-1}$ for S1-A4 (SEQ ID NO: 38), and 26930 $M^{-1}cm^{-1}$ for US7 (SEQ ID NO: 41). The calculated extinction coefficients of the ED-B specific Lcn2 muteins were 37930 $M^{-1}cm^{-1}$ for mutein N7A (SEQ ID NO: 20), 22920 $M^{-1}cm^{-1}$ for N7E (SEQ ID NO: 22), 21430 $M^{-1}cm^{-1}$ for N9B (SEQ ID NO: 24), and 39420 $M^{-1}$ $cm^{-1}$ for N10D (SEQ ID NO: 26) (Gasteiger et al., supra).

EXAMPLE 8: MEASUREMENT OF BINDING ACTIVITY FOR DIFFERENT Aβ TARGETS IN ELISA EXPERIMENTS

For selective capturing of the Lcn2 muteins carrying the C-terminal Strep-tag II (Schmidt and Skerra (2007) Nat. Protoc. 2, 1528-1535), a 96-well MaxiSorp polystyrene microtitre plate (Nunc, Langenselbold, Germany) was coated with 10 μg/mL StrepMAB-Immo (IBA, Göttingen, Germany) in PBS over night at 4° C. and blocked with 3% (w/v) BSA in PBS/T at room temperature for 1 h. After 3 washing steps with PBS/T, 50 μL of a 1 μM solution of the purified Lcn2 muteins from Example 7 were applied to all wells for 1 h. After washing, 50 μL of a dilution series of the biotinylated targets Aβ40, MBP-Aβ40 or Trx-Aβ28 from Example 2 were added and incubated for 1 h whereby the biotinylated forms of Ova, MBP and Trx from Example 2 served as negative control proteins. The wells were washed again and bound conjugate was detected with 50 μL of ExtrAvidin/AP conjugate (Sigma-Aldrich, Steinheim. Germany) diluted 1:5000 in PBS/T for 1 h, followed by signal development in the presence of 100 μL 0.5 mg/mL p-nitrophenyl phosphate (AppliChem. Darmstadt, Germany) in 100 mM Tris/HCl, pH 8.8, 100 mM NaCl, 5 mM $MgCl_2$. The time course of absorption ΔA/Δt at 405 nm was measured in a SpectraMax 250 reader (Molecular Devices, Sunnyvale.

USA) and the data were fitted with KaleidaGraph software (Synergy software, Reading. PA) to the equation $$\Delta A = \Delta A_{max} \times [L]_{tot}/(K_D+[L]_{tot})$$

whereby $[L]_{tot}$ represents the concentration of the applied ligand conjugate and $K_D$ is the dissociation constant (Voss and Skerra (1997) *Protein Eng.* 10, 975-982).

Alternatively, for a "direct" ELISA, 2 μM unlabeled A340 target from Example 2 was adsorbed onto a 96-well Max-iSorp polystyrene microtiter plate (Nunc, Langenselbold, Germany) and incubated with the purified Lcn2 mutein, which was detected via the Strep-tag II using a 1:1500 dilution of Streptavidin/AP conjugate (GE Healthcare UK Ltd, Buckinghamshire, UK). As a control, 2 μM MBP from Example 2 was adsorbed onto the ELISA plate. Absorption at 405 nm was measured in a SpectraMax 250 reader (Molecular Devices, Sunnyvale, USA).

Alternatively, a "competitive" ELISA was performed in a similar manner as the "capture" ELISA described above. Again, after immobilizing StrepMAB-Immo and washing, 50 μL of a 1 μM solution of the purified Lcn2 mutein from Example 7 was applied to all wells for 1 h. After washing, the biotinylated target Trx-Aβ28 from Example 2 was applied at a fixed concentration of 5 nM (for S1-A4) or 40 nM (for US7) in the presence of varying concentrations of the free non-labeled Trx-A328 target as competitor. Starting with a 100-fold excess, the competitor concentration was decreased by the factor 3 in each step. In this case, the data were fitted to the sigmoidal equation $$\Delta A = (\Delta A_{max} - \Delta A_{min})/(1+([L]_{tot}^{free}/K_D))^p) + \Delta A_{min}$$

with curve slope p (Hill coefficient) as a further parameter.

The following table I summarizes the $K_D$ values determined in the different ELISA setups as well as in surface plasmon resonance (see Example 9).

TABLE 1

| | $K_D$ [nM] | | |
|---|---|---|---|
| | S1-A4 | US7 | H1-G1 |
| Aβ40 (Capture ELISA, see FIG. 5) | 2.7 ± 0.1 | 6.8 ± 0.4 | 16.2 ± 1.9 |
| Trx-Aβ28 (Capture ELISA, see FIG. 5) | 1.9 ± 0.1 | 2.4 ± 0.2 | 24.3 ± 3.8 |
| MBP-Aβ40 (Capture ELISA, see FIG. 5) | 4.7 ± 0.1 | 11.4 ± 0.6 | n.d. |
| Aβ16-27 (Capture ELISA, see FIG. 5) | 2.6 ± 0.3 | 2.1 ± 0.1 | n.d. |
| Trx-Aβ28 (Direct ELISA, see FIG. 6) | 16.2 ± 4.4 | 9.6 ± 1.7 | 290 ± 62 |
| MBP-Aβ40 (Direct ELISA, see FIG. 6) | 149 ± 31 | 49.7 ± 8.1 | n.d. |
| Trx-Aβ28 (Comp. ELISA, see FIG. 7) | 21.7 ± 1.5 | 76.9 ± 4.5 | n.d. |
| MBP-Aβ40 (SPR, see FIG. 8, Example 9) | 1.7 | 1.3 | n.d. |

EXAMPLE 9: MEASUREMENT OF BINDING ACTIVITY FOR Aβ VIA SURFACE PLASMON RESONANCE (SPR)

Real time analysis of Lcn2 muteins was performed on a Biacore X system (Biacore, Uppsala, Sweden) using PBS/T (PBS containing 0.005% (v/v) Tween 20) as running buffer. A 50 μg/mL solution of MBP-Aβ40 from Example 2 in 10 mM Na-acetate, pH 4.5 was immobilized onto a CMD 2001 chip (Xantec, Disseldorf, Germany) using standard amine coupling chemistry, resulting in a ligand density of 1455 resonance units (RU). The purified Lcn2 muteins S1-A4 and US7 from Example 7 were applied in concentrations ranging from 2 nM to 125 nM at a flow rate of 10 μL/min. The sensorgrams were corrected by subtraction of the corresponding signals measured for the control channel, which had been activated and blocked with ethanolamine. Kinetic data evaluation was performed by fitting with BIAevaluation software V 3.0 (Karlsson et al. (1991) *J. Immunol. Methods* 145, 229-240). During this step the $k_{on}$ and $k_{off}$ rates were fitted globally, while the maximum response difference $R_{max}$ was fitted locally for each curve.

EXAMPLE 10: DETERMINATION OF THE Aβ EPITOPE VIA EPITOPE MAPPING ON A SPOT MEMBRANE

The SPOT membrane (Amino-PEG500-UC540 sheet, 100×150 mm, Intavis, Köln, Germany) for mapping the Aβ epitope of the Lcn2 muteins S1-A4 and US7 was prepared in an automated procedure as described by Frank ((2002) *J. Immunol. Methods* 262, 13-26) using a MultiPep RS instrument (Intavis, Köln, Germany) and activated amino acids from the same vendor. The A340 amino acid sequence (SEQ ID NO: 29) was synthesized on the membrane in successive hexamers, decamers, and pentadecamers, each with a dislocation of 1 amino acid, thus covering the entire sequence. The C-termini of these peptides became covalently attached to the membrane whereas their N-termini were acetylated. Immobilized Strep-tag II served as a positive control for the detection method.

Side chain deprotection was performed with 95% trifluoroacetic acid (Sigma-Aldrich, Steinheim, Germany), 3% triisopropylsilane (Sigma-Aldrich, Steinheim, Germany), and 2% distilled $H_2O$ for 2 h. After washing the membrane 4 times with dichloromethane (Sigma-Aldrich, Steinheim, Germany), twice with dimethylformamide (Sigma-Aldrich, Steinheim, Germany), and twice with ethanol, the membrane was air-dried.

Prior to use, the membrane was washed once with ethanol, 3 times with PBS (4 mM $KH_2PO_4$, 16 mM $Na_2HPO_4$, 115 mM NaCl, pH 7.4), and blocked with 3% (w/v) BSA in PBS/T (PBS containing 0.1% (v/v) Tween 20) for 1 h. After washing 3 times with PBS/T, the membrane was incubated with the Lcn2 mutein S1-A4 (50 nM), US7 (100 nM) or wild-type Lcn2 (100 nM) in PBS/T for 1 h and washed 3 times with PBS/T. Then, the membrane was incubated with a 1:1500 dilution of Streptavidin/AP conjugate (GE Healthcare, Buckinghamshire, UK) in PBS/T for 1 h for the protein detection via the Strep-tag 11. Subsequently, the membrane was washed 3 times with PBS/T and once in Aβ buffer (100 mM Tris/HCl, pH 8.8, 100 mM NaCl, 5 mM $MgCl_2$), followed by a chromogenic reaction with 5-bromo-4-chloro-3-indolyl phosphate, 4-toluidine salt (BCIP; AppliChem, Darmstadt, Germany) and nitro blue tetrazolium (NBT; AppliChem, Darmstadt, Germany) in Aβ buffer as described by Schlehuber et al. ((2000) *J. Mol. Biol.* 297, 1105-1120).

Comparison of the membranes incubated with S1-A4 and wild-type Lcn2, respectively, yielded prominent spots that only occurred upon incubation of the membrane with S1-A4 and not with wild-type Lcn2. With the pentadecameric A0340 fragments the motif LVFFAED (SEQ ID NO: 57) appeared to be essential for binding of S1-A4. With the shorter hexameric and decameric peptide sequences binding of S1-A4 to the minimal motives VFFAED (SEQ ID NO:

58) and FFAEDV(SEQ ID NO: 59) was detected. The Lcn2 mutein US7 showed a very similar epitope profile in this assay.

EXAMPLE 11: FUNCTIONAL ANALYSIS OF LCN2 MUTEINS WITH AFFINITY TO Aβ IN A THT AGGREGATION ASSAY

Solubilized and homogenously monomeric, non-biotinylated Aβ40 from Example 2 was subjected to a thioflavin T aggregation assay in the presence or absence of various Lcn2 muteins. Thioflavin T (ThT; Sigma-Aldrich, Steinheim, Germany) specifically binds to β-sheet-rich amyloid fibrils and oligomeric precursors but not to the monomeric Aβ peptide, which is accompanied by an increase in ThT fluorescence (Khurana et al. (2005) *J. Struct. Biol.* 151, 229-238).

To this end, ThT was dissolved in distilled $H_2O$ to a concentration of 1 mM. The working solution was prepared by diluting the 1 mM stock solution to a final concentration of 5 μM with 5 mM glycine NaOH, pH 8.5. 500 μL of a 1:1 mixture of 200 μM Aβ40 in distilled $H_2O$ (dissolved according to Example 2) and 20 μM of the Lcn2 mutein from Example 7 in PBS was incubated at 37° C. without agitation. Before each fluorescence measurement at different time points, samples were vortexed shortly 10 times and 20 μL of the respective sample were mixed with 180 μL of the ThT working solution. Fluorescence intensity was measured with an excitation wavelength of 450 nm and an emission wavelength of 482 nm in a luminescence spectrometer (LS 50 B, Perkin Elmer, Waltham. USA).

As illustrated in FIG. 9, the Lcn2 mutein US7 showed potent inhibition of Aβ40 aggregation at a ratio of 1:10.

EXAMPLE 12: PREPARATION OF RECOMBINANT FIBRONECTIN FRAGMENTS CONTAINING THE EXTRA DOMAIN B (ED-B)

Three different recombinant fragments of human fibronectin were used as targets for selection: the extra domain-B alone (termed ED-B: Zardi et al. (1987) *EMBO Journal*, 6, 2337-2342), the same domain in context of its adjacent domains 7 and 8 (referred to as FN7B8), and FN789 comprising the conventional domains 7, 8 and 9, lacking ED-B (Camemolla et al. (1996), *Int. J. Cancer*, 68, 397-405; Leahy et al. (1994) *Proteins* 19, 48-54).

Coding sequences of FN7B8, FN789, and ED-B were cloned on the vector pASK75 (Skerra (1994) *Gene* 151, 131-135) or its derivative pASG-IBA-33 (IBA, Göttingen, Germany), yielding pASK75-FN7B8 (SEQ ID NO: 13), pASK75-FN789 (SEQ ID NO: 17), and pASG-IBA-33-EDB (SEQ ID NO: 15), respectively. All constructs provide a $His_6$-tag (SEQ ID NO: 54) at the carboxy terminus for the purification via immobilized metal affinity chromatography (IMAC) and were produced as soluble proteins in the cytoplasm of *E. coli* TG1/F⁻ [a derivative of *E. coli* K12 TG1 (Gibson (1984) Studies on the Epstein-Barr virus genome, Cambridge University, England)] or BL21 (Studier and Moffatt (1986). 189, 113-130). Therefore, a 2-L culture of *E. coli* harboring the expression plasmid was grown to mid-log phase at 37° C. in LB-medium containing 100 μg/ml ampicillin. After addition of 200 μg/L anhydrotetracycline (Acros, Geel, Belgium) growth was continued for 5 to 7 h at 37° C. Cells were concentrated by centrifugation, resuspended in 35 ml ice-cold chromatography buffer (40 mM Hepes/NaOH, 1 M NaCl, pH 7.5) and lysed by sonication (S250D, Branson, Danbury CT, USA).

The purification protocol given below was the same for all three recombinant fibronectin fragments. The cleared lysate was applied to a $Zn^{2+}$/IDA-Sepharose column (GE Healthcare, Munich, Germany) charged with 10 mM $ZnSO_4$ and equilibrated with 40 mM Hepes/NaOH, 1 M NaCl, pH 7.5. Bound Protein was eluted with a shallow gradient between 0 to 300 mM imidazole (pH adjusted with HCl) in chromatography buffer. Fractions containing recombinant protein were identified by SDS-PAGE, mixed with EDTA to a final concentration of 1 mM, and dialysed against 20 mM Hepes/NaOH, pH 7.4 overnight. Subsequently, the protein was loaded on an ion-exchange chromatography column (Resource Q, GE Healthcare, Munich. Germany) equilibrated with 20 or 40 mM Hepes/NaOH, pH 7.4. To elute bound fibronectin fragments a gradient between 0 and 300 mM NaCl was used.

Finally, purity of the proteins was confirmed by SDS-PAGE analysis and size exclusion chromatography. To determine the concentration of proteins by absorption measurement at 280 nm, the following calculated extinction coefficients (Gasteiger et al. (2003) *Nucleic Acids Res.* 31, 3784-3788) were used: 31,400 $M^{-1}cm^{-1}$ for FN7B8, 28420 $M^{-1}cm^{-1}$ for FN789, and 11460 $M^{-1}cm^{-1}$ for ED-B. Typically, about 10 to 20 mg purified protein was obtained per 2-L shake flask culture. Purified proteins were stored at 4° C. and used for all experiments.

Purified fibronectin fragments were digoxigenin-labeled with an excess (4:1 molar ratio) of digoxigenin-3-O-methylcarbonyl-ε-aminocaproic acid-N-hydroxysuccinimide ester (Roche Diagnostics, Mannheim, Germany) for 1 h at room temperature according to the supplier's manual. To remove free digoxigenin the protein solution was applied to a PD-10 desalting column (GE Healthcare, Munich, Germany) equilibrated with 40 mM Tris/HCl, 115 mM NaCl and 1 mM EDTA, pH 7.5. Successful digoxigenation and integrity of the protein was checked by SDS-PAGE, ESI mass spectrometry or dot blot via staining with Anti-Digoxigenin-AP, Fab fragment (Roche Diagnostics, Mannheim, Germany).

EXAMPLE 13: SELECTION OF LCN2 VARIANTS WITH AFFINITY TO ED-B BY PHAGE DISPLAY

Altogether four phagemid display selection cycles were carried out using the Lcn2 random phagemid library based on the synthetic gene collection originally synthesized by Sloning BioTechnology GmbH as described in Example 1. For the first selection cycle about $5 \times 10^{12}$ recombinant phagemids dissolved in 300 μL TBS/E (40 mM Tris/HCl, 115 mM NaCl and 1 mM EDTA, pH 7.4) supplemented with 50 mM benzamidine were blocked for 30 min by adding 100 μL 8% (w/v) BSA (Sigma-Aldrich, Munich, Germany) in TBS containing 0.4% (v/v) Tween 20 [polyoxyethylene sorbitan monolaurate; AppliChem, Darmstadt, Germany]). Then, this solution was incubated for 1 h with Anti-Digoxigenin IgG Magnetic Beads (Europa Bioproducts, Cambridge, UK) that had been blocked for 1 h with 2% (w/v) BSA in TBS/T (TBS containing 0.1° % (v/v) Tween 20) and charged with 400 μl of 0.1 μM digoxigenin-labeled recombinant FN7B8 (see Example 12).

After collecting the beads via a magnet and discarding the supernatant, 10 washing steps with TBS/T were performed and remaining bound phagemids were first eluted with 400 μl of 0.1 M triethylamine (pH not adjusted) for 6 min, followed by a second elution with 350 μl of 0.1 M glycine/HCl, pH 2.2 for 8 min. Eluates were collected and immediately neutralized with an appropriate amount of 2 M acetic acid or 50 µl 0.5 M Tris base, respectively, combined, and used to infect exponentially growing E. coli XL1-Blue. The phagemids were titered and reamplified prior to the next panning step following published protocols (Beste et al. (1999) PNAS 96, 1898-903: Schlehuber et al. (2000) J Mol Biol 297 1109-20).

For the second round of selection about $2 \times 10^{12}$ amplified phagemids were used and elution of bound phagemids was performed by competition with 400 µl of 231 nmol/ml free recombinant ED-B for 75 min.

In the third and fourth selection cycles about $2 \times 10^{12}$ of the amplified phagemids were first incubated for 1 h with 100 nM digoxigenin-labeled FN7B8. Then, the phagemid-antigen complexes were captured on Anti-Digoxigenin IgG Magnetic Beads for 20 min. After washing the beads ten times with TBS/T, bound phagemids were eluted by competition with 400 µl of 140 to 231 nmol/ml of free recombinant ED-B for 75 min at room temperature.

EXAMPLE 14: SELECTION OF LCN2 VARIANTS WITH AFFINITY TO ED-B BY SCREENING ELISA

Enrichment of Lcn2 muteins resulting from the phage display selection described in Example 13 which specifically bind to the target protein ED-B was monitored by screening ELISA. Using the pooled phasmid preparation from the last panning step, the mutagenized gene cassette was subcloned via BstXI on the expression plasmid phNGAL98, which encodes a fusion of the OmpA signal peptide for the periplasmatic production in E. coli and the Lcn2 coding region with the C-terminal Strep-tag II (Schmidt and Skerra (2007) Nat. Protoc. 2, 1528-1535). Soluble expression of individual Lcn2 muteins in 96-well plates was performed as follows: 100 µl TB medium (Tartof and Hobbs (1987) Bethesda Research Laboratory Focus 9, 12) containing 100 µg/ml ampicillin was inoculated with a single, randomly picked colony and incubated for 5 h at 37° C. with shaking (500 to 800 rpm; Thermomixer comfort; Eppendorf, Hamburg, Germany). For each clone 100 µl of fresh medium was inoculated with 10 µl of this culture and incubated for 1 to 2 h at 37° C. with shaking followed by lowering the temperature to 22° C. After further incubation for 2-4 h expression of Lcn2 muteins was induced in exponentially growing cells for 12-14 h with 0.2 µg/ml anhydrotetracycline (Acros, Geel. Belgium). Periplasmic release of proteins was effected by the addition of 40 µl 2×BBS (0.2 M borate/NaOH, 160 mM NaCl, 1 mM EDTA, pH 8.0) containing 1 mg/ml lysozyme (Roche Diagnostics, Mannheim, Germany) for 1 h at room temperature with shaking. Lysates were blocked with 40 µl 10% w/v BSA (Applichem, Darmstadt, Germany) in TBS and 0.5% Tween-20 for 1 h and cell debris was removed from the crude extract by centrifugation for 10 min.

To adsorb FN7B8 or FN789 on the surface of a 96-well Nunc Maxisorp plate (Thermo Fisher Scientific, Langenselbold, Germany) 50 µl of a 100 µg/ml protein solution in TBS was added per well and incubated overnight at 4° C. After three washing steps with TBS/T, wells were blocked with 2% (w/v) BSA in TBS/T for 3 h at room temperature and washed repeatedly before exposition to crude extract from E. coli. For ELISA, 50 µl of the cleared lysate was applied per well, incubated for 1 h, followed by washing three times with TBS/T. Bound Lcn2 muteins were detected with Streptavidin-alkaline phosphatase conjugate (1:1500 in TBS/T; GE Healthcare, Munich, Germany) using the substrate 4-nitrophenyl phosphate (pNpp, 0.5 mg/ml; AppliChem GmbH, Darmstadt, Germany) in 0.1 M Tris/HCl, 0.1 M NaCl, 5 mM $MgCl_2$, pH 8.8 (see Example 16).

Four clones were identified in this screening ELISA. In subsequent experiments (see Examples 16-18) these four Lcn2 muteins were found to also show specific binding activity for FN7B8 in ELISA. SPR-analysis, and in immunofluorescence microscopy of ED-B positive human colon cancer cells. These Lcn2 muteins were designated as N7A (SEQ ID NO: 20). N7E (SEQ ID NO: 22). N9B (SEQ ID NO: 24), and N10D (SEQ ID NO: 26).

EXAMPLE 15: SOLUBLE PROTEIN PRODUCTION AND PURIFICATION OF LCN2 AND ITS VARIANTS

See Example 7 for details.

EXAMPLE 16: MEASUREMENT OF BINDING ACTIVITY FOR ED-B IN AN ELISA

To adsorb FN7B8 or FN789 onto the surface of a 96-well Nunc Maxisorp plate (Thermo Fisher Scientific, Langenselbold, Germany) 50 µl of a 100 µg/ml protein solution in TBS/E was added per well and incubated at room temperature for 2 h. Additionally, to include control proteins, blank wells were exposed to 120 µl 2% (w/v) BSA (AppliChem, Darmstadt, Germany) in TBS/ET. After three washing steps, wells were blocked with 120 µl 2% (w/v) BSA (AppliChem. Darmstadt, Germany) in TBS/ET for 2 h at room temperature and washed repeatedly before 50 µL of a dilution series of the purified Lcn2 mutein was added and incubated for 1 h. The wells were washed again and bound Lcn2 muteins were detected with 50 µL of Streptavidin-alkaline phosphatase conjugate (GE Healthcare, Munich, Germany) diluted 1:1500 in TBS/T for 1 h, followed by signal development in the presence of 50 µl 0.5 mg/ml p-nitrophenyl phosphate in 100 mM Tris/HCl. 100 mM NaCl, 5 mM $MgCl_2$, pH 8.8. The time course of absorption $\Delta A/\Delta t$ at 405 nm was measured in a SpectraMax 250 reader (Molecular Devices, Sunnyvale, CA) and the data were fitted with KaleidaGraph software (Synergy software, Reading, PA) to the equation $$\Delta A = \Delta A_{max} \times [L]_{tot}/(K_D + [L]_{tot})$$

whereby $[L]_{tot}$ represents the concentration of the applied ligand conjugate and $K_D$ is the dissociation constant (Voss and Skerra (1997) Protein Eng. 10, 975-982). Lcn2 variants N7A, N9B, and N10D, respectively, were found to specifically bind to FN7B8 with $K_D$ values of 14.8 nM (N7A), 40.1 nM (N9B), 30.0 nM (N7E), and 51.2 (N10D) but not to FN789 or BSA.

EXAMPLE 17: MEASUREMENT OF BINDING ACTIVITY FOR RECOMBINANT FIBRONECTIN FN7B8 VIA SURFACE PLASMON RESONANCE (SPR)

Real time analysis of Lcn2 muteins was performed on a BIAcore X system (BIAcore, Uppsala. Sweden) using HBS/ET (20 mM Hepes, pH 7.5, 150 mM NaCl, 1 mM EDTA containing 0.005% (v/v) Tween 20) as running buffer. 200 µg/ml solution of recombinant FN7B8 in 10 mM Na-acetate. pH 4.0 was immobilized on a CMD 200 m Sensorchip (XanTec bioanalytics, Duesseldorf, Germany) using standard amine coupling chemistry (Biacore, Uppsala, Sweden), resulting in a ligand density of about 500 resonance units (RU). The purified Lcn2 mutein was applied at a flow rate of 25 μl/min at concentrations of 2.5 up to 160 nM. The sensorgrams were corrected by subtraction of the corresponding signals measured for the control channel, which had been activated and blocked with ethanolamine. Kinetic data evaluation was performed by global fitting with BIAevaluation software V 4.1 (Karlsson et al. (1991) *J. Immunol. Methods* 145, 229-240).

TABLE 2

Kinetic binding data of selected Lcn2 muteins for FN7B8 determined by surface plasmon resonance.

| Lcn2 variant | $k_{on}$ [M$^{-1}$s$^{-1}$] | $k_{off}$ [s$^{-1}$] | $K_D$ [M] |
|---|---|---|---|
| N7A | $4.6 \times 10^6$ | $2.6 \times 10^{-2}$ | $5.8 \times 10^{-9}$ |
| N7E | $4.1 \times 10^6$ | $3.0 \times 10^{-2}$ | $7.2 \times 10^{-9}$ |
| N9B | $2.1 \times 10^6$ | $7.5 \times 10^{-2}$ | $3.6 \times 10^{-8}$ |
| N10D | $1.5 \times 10^6$ | $5.8 \times 10^{-2}$ | $3.8 \times 10^{-8}$ |

EXAMPLE 18: IMMUNOSTAINING OF ED-B POSITIVE CACO2 CELLS

Human cancer colon cells (CaCo2 cells kindly provided by H. Daniel, Technische Universität München, Germany: Pujuguet et al., *Am. J. Pathol.* 148, 579-592) were cultured on the Nunc Lab-Tek™ II chamber Slide™ system (4 chambers per slide; Thermo Fisher Scientific, Langenselbold. Germany) in MEM with Earle's Salts and L-Glutamine, supplemented with 10% Fetal Bovine Serum, 1×MEM non-essential amino acids, and 50 μg/ml gentamycin (PAA Laboratories, Pasching, Austria) at 37° C. in a humidified atmosphere until cell confluence was about 50 to 70%. Cell monolayers attached to the cover slide were washed with PBS (Dulbecco's without Ca$^{2+}$ and Mg$^{2+}$; PAA Laboratories, Pasching. Austria), followed by distilled water, and then fixed and counterstained with ice-cold methanol containing 5 μg/ml DAPI (4',6-diamidino-2-phenylindol; Sigma-Aldrich, Munich, Germany) for 5 min.

All subsequent incubations were carried out in the dark. Fixed cells were washed and incubated with 500 μl 1 μM wild type Lcn2. Lcn2 mutein, PBS or ED-B specific antibody scFv-L19 (Pini et al. (1998) *J. Biol. Chem.* 273, 21769-21776) for 1 h. All of these reagents were purified as Strep-tag II fusion proteins (Schmidt and Skerra, supra). Cells were washed with PBS and incubated with unlabeled Antibody StrepMABimmo (5 μg/ml in PBS; IBA. Göttingen, Germany) for 1 h, followed by 2 washing steps. Finally, specific binding to CaCo2 cells was detected using a fluorescence labeled anti-mouse IgG (H+L) F(ab')$_2$ fragment Dylight-488 conjugate (Cell Signaling Technology, Danvers, USA), diluted 1:200 in PBS, as a secondary antibody.

All Lcn2 variants and also the antibody scFv-L19 showed specific cell staining when observed under a Axiovert 40 CFL microscope (Carl Zeiss, Göttingen, Germany) whereas recombinant wild type Lcn2 and PBS revealed negligible signals in this assay.

EXAMPLE 19: GENERATION OF THE A3-SPECIFIC LCN2 MUTEINS H1GA AND H1GV VIA EXCHANGE OF A FREE CYSTEINE RESIDUE IN H1-G1 AT POSITION 36

Cys36 was replaced with Ala or Val by site-directed mutagenesis. To this end, a PCR was conducted with the degenerate oligodeoxynucleotide DH-4 (SEQ ID NO: 45) and the second oligodeoxynucleotide J08rev (SEQ ID NO: 48) as well as plasmid DNA encoding the Lcn2 mutein H1-G1 as template (SEQ ID NO: 37). The amplified fragments were subcloned via BstXI on the expression plasmid phNGAL98 and sequenced to identify the individual substitution variants. Depending on the introduced amino acid exchange the resulting Lcn2 variants were named H1GA (SEQ ID NO: 49, 50) and H1GV (SEQ ID NO: 51, 52).

EXAMPLE 20: SOLUBLE PRODUCTION AND PURIFICATION OF THE NEW AB-SPECIFIC LCN2 MUTEINS H1GA AND H1GV USING *E. COLI* CULTURES WITH A HIGH OPTICAL DENSITY

The recombinant Lcn2 and its muteins were produced by periplasmic secretion in *E. coli* JM83. For soluble protein expression the plasmid phNGAL98 with the corresponding BstXI insert encoding either H1GA (SEQ ID NO: 49) or H1GV (SEQ ID NO: 51) was used.

Cultures were grown under agitation at 22° C. in 2 L LB medium containing 100 mg/L ampicillin (Amp). Gene expression was induced at a cell density of OD$_{550}$=2.5 by adding anhydrotetracycline (aTc) to a final concentration of 0.2 mg/L. After incubation for 5 h the cells were harvested by centrifugation, resuspended in 40 mL ice-cold periplasmic fractionation buffer (0.5 M sucrose, 1 mM EDTA, 100 mM Tris-HCl pH 8.0) containing 0.1 mg/mL lysozyme and incubated on ice for 30 min. The resulting spheroplasts were sedimented by repeated centrifugation, and the supernatant containing the soluble recombinant protein was recovered.

The soluble protein was affinity-purified by means of the Strep-tag II, followed by size exclusion chromatography (SEC) on a Superdex 75 HR 10/30 column using PBS buffer (4 mM KH$_2$PO$_4$, 16 mM Na$_2$HPO$_4$, 115 mM NaCl, pH 7.4). Protein purity was checked by SDS-PAGE. Protein concentrations were determined by absorption measurement at 280 nm using a calculated extinction coefficient of 27055 M−1cm−1 for the Aβ specific muteins H1GA (SEQ ID NO: 50) and H1GV (SEQ ID NO: 52).

EXAMPLE 21: MEASUREMENT OF BINDING ACTIVITY FOR MBP-Aβ40 VIA SURFACE PLASMON RESONANCE ON A BIACOREX INSTRUMENT

Real time analysis of the interaction between Lcn2 muteins H1GA or H1GV and MBP-Aβ40 (SEQ ID NO: 33) was performed on a Biacore X system using PBS/T (4 mM KH$_2$PO$_4$, 16 mM Na$_2$HPO$_4$, 115 mM NaC, pH 7.4 containing 0.005% (v/v) Tween 20) as running buffer. A 15 μg/mL solution of MBP-Aβ40 from Example 2 in 10 mM Na-acetate, pH 4.5 was immobilized onto a CMD 2001 chip (Xantec, Düsseldorf, Germany) using standard amine coupling chemistry, resulting in a ligand density of 1316 resonance units (RU). The purified Lcn2 muteins H1GA and H1GV from Example 20 were applied in concentrations ranging from 4 nM to 128 nM at a flow rate of 20 μL/min. The data were double-referenced by subtraction of the corresponding signals measured for the control channel, which had been activated and blocked with ethanolamine, as well as subtraction of the measured signals for an average of buffer injections. Kinetic data were fitted globally using the BIAevaluation software V 3.0 (Karlsson et al. (1991) *J. Immunol. Methods* 145, 229-240).

EXAMPLE 22: MEASUREMENT OF BINDING ACTIVITY FOR A1340 VIA SURFACE PLASMON RESONANCE ON A BIACORE T100 INSTRUMENT

Real time analysis of the interaction between the Lcn2 mutein H1GA and Aβ40 (SEQ ID NO: 29) was performed on a Biacore T100 system (Biacore, Uppsala, Sweden) using PBS/P (4 mM $KH_2PO_4$, 16 mM $Na_2HPO_4$, 115 mM NaCl, pH 7.4 containing 0.005% (v/v) Surfactant P20) as running buffer. A 10 μg/mL solution of Aβ40 from Example 2 in 10 mM sodium acetate pH 4.5 was immobilized onto a CM5 chip (Biacore, Uppsala, Sweden) using standard amine coupling chemistry, resulting in a ligand density of 325 RU. The purified Lcn2 mutein H1GA from Example 20 was applied in concentrations ranging from 1 nM to 32 nM at a flow rate of 30 μL/min. The dilution series of H1GA was injected with both association and dissociation times of 300 s to obtain $k_{on}$ information. For exact determination of the low $k_{off}$ rate the highest concentration was analysed using a dissociation time of 7200 s. The data were double-referenced as in Example 21. $k_{on}$ and $k_{off}$ for the binding reaction were determined from the entire data set using Biacore T100 Evaluation Software V2.0.3 for data processing and kinetic fitting. The data was globally fitted using a 1:1 binding model.

EXAMPLE 23: FUNCTIONAL ANALYSIS OF THE LCN2 MUTEIN H1GA IN A THT AGGREGATION ASSAY

For the Thioflavin T (ThT) aggregation assay synthetic Aβ peptide (SEQ ID NO: 29) was dissolved in 1,1,1,3,3,3-hexafluoro-2-propanol (HFIP; Sigma-Aldrich, Steinheim. Germany) for 12 h. HFIP was evaporated under vacuum, and Aβ was dissolved in a suitable volume of $H_2O$ dd, sonicated for 15 min at 4° C., and filtrated (Costar Spin-X centrifuge tube filter cellulose acetate membrane, 0.45 μm; Corning Inc., Corning, NY). The solubilized monomeric Aβ was then immediately used for the aggregation assays.

500 μl of 1 mg/ml Aβ was incubated in the absence or presence of various Lcn2 muteins at different molar ratios or BSA in 0.5×PBS at 37° C. with stirring. Aggregation reactions were prepared in triplicates. For fluorescence measurement 20 μl of periodically removed samples was mixed with 180 μl ThT at a final concentration of 50 μM in 0.5×PBS and analysed at an excitation wavelength of 450 nm and an emission wavelength of 482 nm using a FluoroMax-3 spectrofluorimeter (HORIBA Jobin Yvon, Grasbrunn, Germany).

EXAMPLE 24: MEASUREMENT OF BINDING ACTIVITY FOR THE RECOMBINANT FIBRONECTIN SINGLE DOMAIN ED-B VIA SURFACE PLASMON RESONANCE (SPR)

Real time interaction analysis of Lcn2 muteins was performed on a BIAcore X instrument using HBS/ET (20 mM Hepes, pH 7.5, 150 mM NaCl, 1 mM EDTA containing 0.005% (v/v) Tween 20) as running buffer. 100 μg/ml solution of recombinant ED-B in 10 mM Na-acetate, pH 4.0 was immobilized on a CMD 200 m Sensorchip using standard amine coupling chemistry, resulting in a ligand density of about 180 resonance units (RU). The purified Lcn2 mutein was applied at a flow rate of 25 μl/min at concentrations of 2.5 up to 160 nM. The sensorgrams were corrected by subtraction of the corresponding signals measured for the control channel, which had been activated and blocked with ethanolamine. Kinetic data evaluation was performed by global fitting with BIAevaluation software V 4.1 (Karlsson et al. (1991) J. Immunol. Methods 145, 229-240). In the case of N10D the heterogeneous analyte competing reaction model was used for data fitting, resulting in two sets of kinetic constants.

TABLE 3

Kinetic binding data of Lcn2 muteins for ED-B determined by surface plasmon resonance.

| Lcn2 variant | $k_{on}$ [$M^{-1}s^{-1}$] | $k_{off}$ [$s^{-1}$] | $K_D$ [M] |
|---|---|---|---|
| N7A | $1.8 \times 10^6$ | 0.138 | $1.27 \times 10^{-7}$ |
| N7E | $3.1 \times 10^6$ | 0.054 | $1.73 \times 10^{-8}$ |
| N9B | $1.45 \times 10^6$ | $7.62 \times 10^{-3}$ | $5.26 \times 10^{-9}$ |
| N10D | $k_1 = 6.21 \times 10^5$<br>$k_2 = 2.94 \times 10^4$ | $k_{-1} = 0.064$<br>$k_{-2} = 3.35 \times 10^{-3}$ | |

What is claimed:

1. A human neutrophil gelatinase-associated lipocalin (hNGAL) mutein, comprising a mutated amino acid residue at one or more amino acid sequence positions selected from the group consisting of amino acid sequence positions 96, 100, and 106 of mature hNGAL (SEQ ID NO: 44) and at nine or more amino acid sequence positions selected from the group consisting of amino acid sequence positions 36, 40, 41, 49, 52, 68, 70, 72, 73, 77, 79, 81, 103, 125, 127, 132, and 134 of mature hNGAL (SEQ ID NO: 44), wherein the mutein demonstrates binding to a target with detectable affinity, which is a non-natural ligand in that it does not bind to the mature hNGAL (SEQ ID NO: 44) with detectable affinity under physiological conditions, and wherein the mutein comprises with respect to the mature hNGAL (SEQ ID NO: 44) one or more amino acid replacements that are:
  (A) selected from the group consisting of Leu36→Val or Cys or Ala: Ala40→Tyr or Lys or Val: Ile41→Thr or Ser or Leu: Gln49→Leu or Trp; Leu70→Gly; Arg72→Gly or Asp; Lys73→Leu or Thr or Asp; Asp77→Asn or His or Leu; Trp79→Lys; Asn96→Ile or Arg; Tyr100→Gln or Arg or Glu; Leu103→Met or Arg or Gly: Tyr106→Tyr or Ala or Trp; Lys125→Thr or Val or Glu; Ser127-Gly or Gin or Ala; Tyr132→Met or Ser or Thr; and Lys134→Asn; or
  (B) selected from the group consisting of Leu36→Lys or Glu or Arg or Ala; Ala40→His or Met or Thr or Ser, Ile41→Asp or Arg or Trp or Leu; Gln49→Arg or Ala or Tyr; Leu70→Leu or Arg or Met; Arg72→Val or Arg or Gln or Met; Lys73→His or Arg or Ser, Asp77→Asn or His or Lys or Arg; Trp79→Arg or Met or Leu; Asn96→Lys or Ala or Ser; Tyr100→Trp or Pro or Lys; Leu103→His or Pro; Tyr106→Phe or Trp or Thr; Lys125→Arg or His or Thr; Ser127→Tyr or Phe or Ala; Tyr132→Leu or Phe; Lys134→Glu or His or Gly or Phe; and Ser146→Asn.

2. The mutein of claim 1, wherein the mutated amino acid residue at one or more amino acid sequence positions selected from the group consisting of amino acid sequence positions 96, 100, and 106 of mature hNGAL (SEQ ID NO:44) comprises a mutated amino acid residue at two or more of the amino acid sequence positions.

3. The mutein of claim 1, wherein the mutated amino acid residue at one or more amino acid sequence positions selected from the group consisting of 96, 100, and 106 of mature hNGAL (SEQ ID NO:44) comprises a mutated amino acid residue at each of the amino acid sequence positions.

4. The mutein of claim 1, wherein the mutein comprises with respect to the mature hNGAL (SEQ ID NO: 44) one or more amino acid replacements that are selected from the group consisting of Leu36→Val or Cys or Ala; Ala40→Tyr or Lys or Val; Ile41→Thr or Ser or Leu; Gln49→Leu or Trp; Leu70→Gly; Arg72→Gly or Asp; Lys73→Leu or Thr or Asp; Asp77→Asn or His or Leu; Trp79→Lys; Asn96→Ile or Arg; Tyr100→Gln or Arg or Glu; Leu103→Met or Arg or Gly; Tyr106→Tyr or Ala or Trp; Lys125→Thr or Val or Glu; Ser127→Gly or Gln or Ala; Tyr132→Met or Ser or Thr; and Lys134→Asn.

5. The mutein of claim 1, wherein the mutein comprises with respect to the mature hNGAL (SEQ ID NO: 44) one or more amino acid replacements that are selected from the group consisting of Leu36→Lys or Glu or Arg or Ala; Ala40→His or Met or Thr or Ser; Ile41→Asp or Arg or Trp or Leu; Gln49→Arg or Ala or Tyr; Leu70→Leu or Arg or Met; Arg72→Val or Arg or Gin or Met; Lys73→His or Arg or Ser; Asp77→Asn or His or Lys or Arg; Trp79→Arg or Met or Leu; Asn96→Lys or Ala or Ser; Tyr100→Trp or Pro or Lys; Leu103→His or Pro; Tyr106→Phe or Trp or Thr; Lys125→Arg or His or Thr; Ser127→Tyr or Phe or Ala; Tyr132→Leu or Phe; Lys134→Glu or His or Gly or Phe; and Ser146→Asn.

6. The mutein of claim 1, wherein said non-natural ligand is selected from the group consisting of a peptide, a protein, a fragment or a domain of a protein, and a small organic molecule.

7. The mutein of claim 1, wherein the mutein comprises with respect to the mature hNGAL (SEQ ID NO: 44) one or both of the amino acid replacements selected from the group consisting of Gln28→His and Cys87→Ser.

8. The mutein of claim 1, wherein the mutein comprises with respect to the mature hNGAL (SEQ ID NO: 44) one or more amino acid replacements selected from the group consisting of Tyr52→Gln or Val; Ser68→Lys or Asn; and Arg81→Trp or Asn or His.

9. The mutein of claim 1, wherein the mutein is conjugated to a compound selected from the group consisting of an organic molecule, an enzyme label, a radioactive label, a colored label, a fluorescent label, a chromogenic label, a luminescent label, a hapten, digoxigenin, biotin, a cytostatic agent, a toxin, a metal complex, metal, and colloidal gold.

10. The mutein of claim 1, wherein the mutein is fused at its N-terminus and/or its C-terminus to a fusion partner which is a protein, a protein domain or a peptide.

11. The mutein of claim 10, wherein the fusion partner of the mutein is a protein domain that extends the serum half-life of the mutein.

12. The mutein of claim 11, wherein the protein domain is an Fc part of an immunoglobulin, a CH3 domain of an immunoglobulin, a CH4 domain of an immunoglobulin, an albumin binding peptide, or an albumin binding protein.

13. The mutein of claim 1, wherein the mutein is conjugated to a compound that extends the serum half-life of the mutein.

14. The mutein of claim 13, wherein the compound that extends the serum half-life is selected from the group consisting of a polyalkylene glycol molecule, hydroxyethyl starch, an Fc part of an immunoglobulin, a CH3 domain of an immunoglobulin, a CH4 domain of an immunoglobulin, an albumin binding peptide, and an albumin binding protein.

15. The mutein of claim 14, wherein the polyalkylene glycol is polyethylene glycol (PEG) or an activated derivative thereof.

16. The mutein of claim 1, wherein the mutein has at least 70% sequence identity to the linear polypeptide sequence of mature hNGAL (SEQ ID NO: 44).

17. A nucleic acid molecule comprising a nucleotide sequence encoding a mutein of claim 1.

18. The nucleic acid molecule of claim 17, wherein the nucleic acid molecule is operably linked to a regulatory sequence to allow expression of said nucleic acid molecule.

19. A host cell containing a nucleic acid molecule of claim 18.

20. A method for the production of a product that is the mutein of claim 1, a fragment of the mutein or a fusion protein of the mutein and another polypeptide, wherein the method comprises:
  subjecting a nucleic acid molecule encoding mature hNGAL to mutagenesis at a nucleotide triplet coding for the at least one amino acid at sequence positions 96, 100, and 106 of the mature hNGAL (SEQ ID NO:44), and for the at least nine amino acid at sequence positions selected from the group consisting of amino acid at sequence positions 36, 40, 41, 49, 52, 68, 70, 72, 73, 77, 79, 81, 103, 125, 127, 132, and 134 of the mature hNGAL (SEQ ID NO:44), resulting in one or more nucleic acid molecule(s) encoding the mutein; and expressing the product from the one or more nucleic acid molecule(s) encoding the mutein.

21. The method of claim 20, wherein the product is produced in a bacterial or eukaryotic host organism and is isolated from said host organism or its culture.

* * * * *

SEQUENCE LISTING

```
<160> NUMBER OF SEQ ID NOS: 67

<210> SEQ ID NO 1
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: NNK oligomer
<220> FEATURE:
<221> NAME/KEY: modified_base
<222> LOCATION: (20)..(21)
<223> OTHER INFORMATION: a, c, t or g
<220> FEATURE:
<221> NAME/KEY: modified_base
<222> LOCATION: (32)..(33)
<223> OTHER INFORMATION: a, c, t or g
<220> FEATURE:
<221> NAME/KEY: modified_base
```

```
<222> LOCATION: (35)..(36)
<223> OTHER INFORMATION: a, c, t or g
<220> FEATURE:
<221> NAME/KEY: modified_base
<222> LOCATION: (59)..(60)
<223> OTHER INFORMATION: a, c, t or g
<220> FEATURE:
<221> NAME/KEY: modified_base
<222> LOCATION: (68)..(69)
<223> OTHER INFORMATION: a, c, t or g

<400> SEQUENCE: 1
gaagtggtat gtggtaggtn nkgcagggaa tnnknnkctc agagaagaca aagacccgnn    60
kaagatgnnk gccaccatct atgagctg                                      88

<210> SEQ ID NO 2
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: NNK oligomer
<220> FEATURE:
<221> NAME/KEY: modified_base
<222> LOCATION: (20)..(21)
<223> OTHER INFORMATION: a, c, t or g
<220> FEATURE:
<221> NAME/KEY: modified_base
<222> LOCATION: (26)..(27)
<223> OTHER INFORMATION: a, c, t or g
<220> FEATURE:
<221> NAME/KEY: modified_base
<222> LOCATION: (32)..(33)
<223> OTHER INFORMATION: a, c, t or g
<220> FEATURE:
<221> NAME/KEY: modified_base
<222> LOCATION: (35)..(36)
<223> OTHER INFORMATION: a, c, t or g
<220> FEATURE:
<221> NAME/KEY: modified_base
<222> LOCATION: (47)..(48)
<223> OTHER INFORMATION: a, c, t or g
<220> FEATURE:
<221> NAME/KEY: modified_base
<222> LOCATION: (53)..(54)
<223> OTHER INFORMATION: a, c, t or g
<220> FEATURE:
<221> NAME/KEY: modified_base
<222> LOCATION: (59)..(60)
<223> OTHER INFORMATION: a, c, t or g

<400> SEQUENCE: 2
caagagctac aatgtcaccn nkgtcnnktt tnnknnkaag aagtgtnnkt acnnkatcnn    60
kacttttgtt ccaggttcc                                                79

<210> SEQ ID NO 3
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: NNK oligomer
<220> FEATURE:
<221> NAME/KEY: modified_base
<222> LOCATION: (19)..(20)
<223> OTHER INFORMATION: a, c, t or g
<220> FEATURE:
<221> NAME/KEY: modified_base
<222> LOCATION: (31)..(32)
```

```
<223> OTHER INFORMATION: a, c, t or g
<220> FEATURE:
<221> NAME/KEY: modified_base
<222> LOCATION: (40)..(41)
<223> OTHER INFORMATION: a, c, t or g
<220> FEATURE:
<221> NAME/KEY: modified_base
<222> LOCATION: (49)..(50)
<223> OTHER INFORMATION: a, c, t or g

<400> SEQUENCE: 3
ggcgagttca cgctgggcnn kattaagagt nnkcctggan nkacgagtnn kctcgtccga      60
gtggtgag                                                              68

<210> SEQ ID NO 4
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: NNK oligomer
<220> FEATURE:
<221> NAME/KEY: modified_base
<222> LOCATION: (19)..(20)
<223> OTHER INFORMATION: a, c, t or g
<220> FEATURE:
<221> NAME/KEY: modified_base
<222> LOCATION: (25)..(26)
<223> OTHER INFORMATION: a, c, t or g
<220> FEATURE:
<221> NAME/KEY: modified_base
<222> LOCATION: (40)..(41)
<223> OTHER INFORMATION: a, c, t or g
<220> FEATURE:
<221> NAME/KEY: modified_base
<222> LOCATION: (46)..(47)
<223> OTHER INFORMATION: a, c, t or g

<400> SEQUENCE: 4
gctatggtgt tcttcaagnn kgttnnkcaa aacagggagn nkttcnnkat caccctctac      60
gggagaac                                                              68

<210> SEQ ID NO 5
<211> LENGTH: 45
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: PCR-Primer with fixed nucleotide sequences
      corresponding to the non-coding strand

<400> SEQUENCE: 5
ggtgacattg tagctcttgt cttctttcag ctcatagatg gtggc                     45

<210> SEQ ID NO 6
<211> LENGTH: 42
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: PCR-Primer with fixed nucleotide sequences
      corresponding to the non-coding strand

<400> SEQUENCE: 6
```
gcccagcgtg aactcgcctg gctgggaacc tggaacaaaa gt                42

<210> SEQ ID NO 7
<211> LENGTH: 54
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: PCR-Primer with fixed nucleotide sequences
      corresponding to the non-coding strand

<400> SEQUENCE: 7
cttgaagaac accatagcat gctggttgta gttggtgctc accactcgga cgag        54

<210> SEQ ID NO 8
<211> LENGTH: 64
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: PCR-Primer with fixed nucleotide sequences
      corresponding to the non-coding strand

<400> SEQUENCE: 8
ggagaagcgg atgaagttct cctttagttc cgaagtcagc tccttggttc tcccgtagag    60
ggtg                                                                64

<210> SEQ ID NO 9
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' flanking PCR-Oligo biotinylated

<400> SEQUENCE: 9
ccaggacaac caattccatg ggaagtggta tgtggtaggt                          40

<210> SEQ ID NO 10
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 3' flanking PCR-Oligo biotinylated

<400> SEQUENCE: 10
ttcagggagg cccagagatt tggagaagcg gatgaagttc                          40

<210> SEQ ID NO 11
<211> LENGTH: 4746
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Phage display vector phNGAL102 with CamR used
      as backbone for NNK-Library

<400> SEQUENCE: 11

```
ccataacgct cggttgccgc cgggcgtttt ttattggcca gatgattaat tcctaatttt      60
tgttgacact ctatcattgg tagagttatt ttaccactcc ctatcagtga tagagaaaag     120
tgaaatgaat agttcgacaa aaatctagat aacgagggca aaaaatgaaa aagacagcta     180
tcgcgattgc agtggctctg gctggcttcg ctaccgtagc gcaggcccag gactccacct     240
cagacctgat cccagcccca cctctgagca aggtccctct gcagcagaac ttccaggaca     300
accaattcca tgggaagtgg tatgtggtag gtctcgcagg gaatgcaatt ctcagagaag     360
acaaagaccc gcaaaagatg tatgccacca tctatgagct gaaagaagac aagagctaca     420
atgtcacctc cgtcctgttt aggaaaaaga agtgtgacta ctggatcagg acttttgttc     480
caggttccca gccaggcgag ttcacgctgg gcaacattaa gagttaccct ggattaacga     540
gttacctcgt ccgagtggtg agcaccaact acaaccagca tgctatggtg ttcttcaaga     600
aagtttctca aaacagggag tacttcaaga tcaccctcta cgggagaacc aaggagctga     660
cttcggaact aaaggagaac ttcatccgct tctccaaatc tctgggcctc cctgaaaacc     720
acatcgtctt ccctgtccca atcgaccagt gtatcgacgg cagcgctggt ggggcctaga     780
ctgttgaaag ttgtttagca aaaccccata cagaaaattc atttactaac gtctggaaag     840
acgacaaaac tttagatcgt tacgctaact atgagggctg tctgtggaat gctacaggcg     900
ttgtagtttg tactggtgac gaaactcagt gttacggtac atgggttcct attgggcttg     960
ctatccctga aaatgagggt ggtggctctg agggtggcgg ttctgagggt ggcggttctg    1020
agggtggcgg tactaaacct cctgagtacg gtgatacacc tattccgggc tatacttata    1080
tcaaccctct cgacggcact tatccgcctg gtactgagca aaaccccgct aatcctaatc    1140
cttctcttga ggagtctcag cctcttaata ctttcatgtt tcagaataat aggttccgaa    1200
ataggcaggg ggcattaact gtttatacgg gcactgttac tcaaggcact gaccccgtta    1260
aaacttatta ccagtacact cctgtatcat caaaagccat gtatgacgct tactggaacg    1320
gtaaattcag agactgcgct ttccattctg gctttaatga ggatccattc gtttgtgaat    1380
atcaaggcca atcgtctgac ctgcctcaac ctcctgtcaa tgctggcggc ggctctggtg    1440
gtggttctgg tggcggctct gagggtggtg gctctgtggg tggcggttct gagggtggcg    1500
gctctgaggg aggcggttcc ggtggtggct ctggttccgg tgattttgat tatgaaaaga    1560
tggcaaacgc taataagggg gctatgaccg aaaatgccga tgaaaacgcg ctacagtctg    1620
acgctaaagg caaacttgat tctgtcgcta ctgattacgg tgctgctatc gatggtttca    1680
ttggtgacgt ttccggcctt gctaatggta atggtgctac tggtgatttt gctggctcta    1740
attcccaaat ggctcaagtc ggtgacggtg ataattcacc tttaatgaat aatttccgtc    1800
aatatttacc ttccctccct caatcggttg aatgtcgccc ttttgtcttt ggcgctggta    1860
aaccatatga ttttctatt gattgtgaca aaataaactt attccgtggt gtctttgcgt     1920
ttcttttata tgttgccacc tttatgtatg tattttctac gtttgctaac atactgcgta    1980
ataaggagtc ttaataagct tgacctgtga agtgaaaaat ggcgcacatt gtgcgacatt    2040
ttttttgtct gccgtttacc gctactgcgt cacggatctc cacgcgccct gtagcggcgc    2100
attaagcgcg gcgggtgtgg tggttacgcg cagcgtgacc gctacacttg ccagcgccct    2160
agcgcccgct cctttcgctt tcttcccttc ctttctcgcc acgttcgccg gctttccccg    2220
tcaagctcta aatcggggc tcccttaggg gttccgattt agtgctttac ggcacctcga    2280
ccccaaaaaa cttgattagg gtgatggttc acgtagtggg ccatcgccct gatagacggt    2340
```

-continued

```
ttttcgccct tgacgttgg agtccacgtt ctttaatagt ggactcttgt tccaaactgg    2400
aacaacactc aaccctatct cggtctattc ttttgattta taagggattt tgccgatttc    2460
ggcctattgg ttaaaaaatg agctgattta acaaaaattt aacgcgaatt ttaacaaaat    2520
ttggcgaaaa tgagacgttg atcggcacgt aagaggttcc aactttcacc ataatgaaat    2580
aagatcacta ccgggcgtat tttttgagtt atcgagattt tcaggagcta aggaagctaa    2640
aatggagaaa aaaatcactg gatataccac cgttgatata tcccaatggc atcgtaaaga    2700
acattttgag gcatttcagt cagttgctca atgtacctat aaccagaccg ttcagctgga    2760
tattacggcc ttttttaaga ccgtaaagaa aaataagcac aagttttatc cggcctttat    2820
tcacattctt gcccgcctga tgaatgctca tccggaattc cgtatggcaa tgaaagacgg    2880
tgagctggtg atatgggata gtgttcaccc ttgttacacc gttttccatg agcaaactga    2940
aacgttttca tcgctctgga gtgaatacca cgacgatttc cggcagtttc tacacatata    3000
ttcgcaagat gtggcgtgtt acggtgaaaa cctggcctat ttccctaaag ggtttattga    3060
gaatatgttt ttcgtctcag ccaatccctg ggtgagtttc accagttttg atttaaacgt    3120
ggccaatatg gacaacttct tcgcccccgt tttcactatg gcaaatatt atacgcaagg    3180 cgacaaggtg ctgatgccgc tggcgattca ggttcatcat gccgtttgtg atggcttcca    3240
tgtcggcaga atgcttaatg aattacaaca gtactgcgat gagtggcagg gcggggcgta    3300
ataggaatta atgatgtctc gtttagataa aagtaaagtg attaacagcg cattagagct    3360
gcttaatgag gtcggaatcg aaggtttaac aacccgtaaa ctcgcccaga agctaggtgt    3420
agagcagcct acattgtatt ggcatgtaaa aaataagcgg ctttgctcg acgccttagc    3480 cattgagatg ttagataggc accatactca cttttgccct ttagaagggg aaagctggca    3540
agatttttta cgtaataacg ctaaaagttt tagatgtgct ttactaagtc atcgcgatgg    3600
agcaaaagta catttaggta cacggcctac agaaaaacag tatgaaactc tcgaaaatca    3660
attagccttt ttatgccaac aaggtttttc actagagaat gcattatatg cactcagcgc    3720
agtggggcat tttactttag gttgcgtatt ggaagatcaa gagcatcaag tcgctaaaga    3780
agaaagggaa acacctacta ctgatagtat gccgccatta ttacgacaag ctatcgaatt    3840
atttgatcac caaggtgcag agccagcctt cttattcggc cttgaattga tcatatgcgg    3900
attagaaaaa caacttaaat gtgaaagtgg gtcttaaaag cagcataacc ttttttccgtg    3960 atggtaactt cactagttta aaaggatcta ggtgaagatc ctttttgata atctcatgac    4020
caaaatccct taacgtgagt tttcgttcca ctgagcgtca gaccccgtag aaaagatcaa    4080
aggatcttct tgagatcctt ttttttctgcg cgtaatctgc tgcttgcaaa caaaaaaacc    4140
accgctacca gcggtggttt gtttgccgga tcaagagcta ccaactcttt ttccgaaggt    4200
aactggcttc agcagagcgc agataccaaa tactgttctt ctagtgtagc cgtagttagg    4260
ccaccacttc aagaactctg tagcaccgcc tacatacctc gctctgctaa tcctgttacc    4320
agtggctgct gccagtggcg ataagtcgtg tcttaccggg ttggactcaa gacgatagtt    4380
accggataag gcgcagcggt cgggctgaac ggggggttcg tgcacacagc ccagcttgga    4440
gcgaacgacc tacaccgaac tgagatacct acagcgtgag ctatgagaaa gcgccacgct    4500
tcccgaaggg agaaaggcgg acaggtatcc ggtaagcggc agggtcggaa caggagagcg    4560
cacgagggag cttccagggg gaaacgcctg gtatctttat agtcctgtcg ggtttcgcca    4620
cctctgactt gagcgtcgat ttttgtgatg ctcgtcaggg gggcggagcc tatggaaaaa    4680
cgccagcaac gcggcctttt tacggttcct ggccttttgc tggccttttg ctcacatgac    4740
```

```
ccgaca                                                              4746
```

<210> SEQ ID NO 12
<211> LENGTH: 4963
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Phage display vector phNGAL108 with AmpR used
      for cloning Library

<400> SEQUENCE: 12

```
ccatcgaatg gccagatgat taattcctaa ttttgttga cactctatca ttgatagagt       60
tattttacca ctccctatca gtgatagaga aagtgaaat gaatagttcg acaaaaatct     120
agataacgag ggcaaaaaat gaaaagaca gctatcgcga ttgcagtggc tctggctggc     180
ttcgctaccg tagcgcaggc ccaggactcc acctcagacc tgatcccagc ccacctctg     240
agcaaggtcc ctctgcagca gaacttccag acaaccaat tccatgggaa gtggtatgtg    300
gtaggtctcg cagggaatgc aattctcaga agagacaaag acccgcaaaa gatgtatgcc   360
accatctatg agctgaaaga agacaagagc tacaatgtca cctccgtcct gtttaggaaa    420
aagaagtgtg actactggat caggacttt gttccaggtt cccagccagg cgagttcacg    480
ctgggcaaca ttaagagtta ccctggatta acgagttacc tcgtccgagt ggtgagcacc   540
aactacaacc agcatgctat ggtgttcttc aagaaagttt ctcaaaacag ggagtacttc   600
aagatcaccc tctacgggag aaccaaggag ctgacttcgg aactaaagga gaacttcatc    660
cgcttctcca atctctggg cctccctgaa aaccacatcg tcttccctgt cccaatcgac    720
cagtgtatcg acggcagcgc ttggcgtcac ccgcagttcg gtggggccta gactgttgaa   780
agttgtttag caaaaccccca tacagaaaat tcatttacta acgtctggaa agacgacaaa  840
actttagatc gttacgctaa ctatgagggc tgtctgtgga atgctacagg cgttgtagtt   900
tgtactggtg acgaaactca gtgttacggt acatggggtc ctattgggct tgctatccct   960
gaaaatgagg gtggtggctc tgaggtgggc ggttctgagg gtggcggttc tgagggtggc  1020
ggtactaaac ctcctgagta cggtgataca cctattccgg gctatactta tatcaaccct  1080
ctcgacggca cttatccgcc tggtactgag caaaaccccg ctaatcctaa tccttctctt  1140
gaggagtctc agcctcttaa tactttcatg tttcagaata taggttccg aaataggcag   1200
gggcattaa ctgtttatac gggcactgtt actcaaggca ctgacccccgt aaaacttat   1260
taccagtaca ctcctgtatc atcaaaagcc atgtatgacg cttactggaa cggtaaattc  1320
agagactgcg ctttccattc tggctttaat gaggatccat tcgtttgtga atatcaaggc  1380
caatcgtctg acctgcctca acctcctgtc aatgctggcg gcggctctgg tggtggttct   1440
ggtggcggct ctgagggtgg tggctctgag ggtggcggtt ctgagggtgg cggctctgag  1500
ggaggcggtt ccggtggtgg ctctggttcc ggtgattttg attatgaaaa gatggcaaac  1560
gctaataagg gggctatgac cgaaaatgcc gatgaaaacg cgctacagtc tgacgctaaa  1620
ggcaaacttg attctgtcgc tactgattac ggtgctgcta tcgatggtt cattggtgac  1680
gtttccggcc ttgctaatgg taatggtgct actggtgatt tgctggctc taattcccaa  1740
atggctcaag tcggtgacgg tgataattca ccttaatga ataatttccg tcaatattta   1800
ccttccctcc ctcaatcggt tgaatgtcgc cctttgtct ttggcgctgg taaaccatat   1860
```

```
gaattttcta ttgattgtga caaaataaac ttattccgtg gtgtctttgc gtttcttttta    1920
tatgttgcca cctttatgta tgtattttct acgtttgcta acatactgcg taataaggag    1980
tcttaataag cttgacctgt gaagtgaaaa atggcgcaca ttgtgcgaca ttttttttgt    2040
ctgccgttta ccgctactgc gtcacggatc tccacgcgcc ctgtagcggc gcattaagcg    2100
cggcgggtgt ggtggttacg cgcagcgtga ccgctacact tgccagcgcc ctagcgcccg    2160
ctcctttcgc tttcttccct tcctttctcg ccacgttcgc cggctttccc cgtcaagctc    2220
taaatcgggg ctcccttta gggttccgat ttagtgcttt acggcacctc gaccccaaaa    2280
aacttgatta gggtgatggt tcacgtagtg ggccatcgcc ctgatagacg ttttttcgcc    2340
ctttgacgtt ggagtccacg ttctttaata gtggactctt gttccaaact ggaacaacac    2400
tcaaccctat ctcggtctat tcttttgatt tataagggat tttgccgatt tcggcctatt    2460
ggttaaaaaa tgagctgatt taacaaaaat ttaacgcgaa ttttaacaaa atattaacgc    2520
ttacaatttc aggtggcact tttcggggaa atgtgcgcgg aaccccctatt tgtttatttt    2580
tctaaataca ttcaaatatg tatccgctca tgagacaata accctgataa atgcttcaat    2640
aatattgaaa aaggaagagt atgagtattc aacatttccg tgtcgccctt attccctttt    2700
ttgcggcatt ttgccttcct gtttttgctc acccagaaac gctggtgaaa gtaaaagatg    2760
ctgaagatca gttgggtgca cgagtgggtt acatcgaact ggatctcaac agcggtaaga    2820
tccttgagag ttttcgcccc gaagaacgtt ttccaatgat gagcactttt aaagttctgc    2880
tatgtggcgc ggtattatcc cgtattgacg ccgggcaaga gcaactcggt cgccgcatac    2940
actattctca gaatgacttg gttgagtact caccagtcac agaaaagcat cttacggatg    3000
gcatgacagt aagagaatta tgcagtgctg ccataaccat gagtgataac actgcggcca    3060
acttacttct gacaacgatc ggaggaccga aggagctaac cgcttttttg cacaacatgg    3120
gggatcatgt aactcgcctt gatcgttggg aaccggagct gaatgaagcc ataccaaacg    3180
acgagcgtga caccacgatg cctgtagcaa tggcaacaac gttgcgcaaa ctattaactg    3240
gcgaactact tactctagct tcccggcaac aattgataga ctggatggag gcggataaag    3300
ttgcaggacc acttctgcgc tcggcccttc cggctggctg gtttattgct gataaatctg    3360
gagccggtga gcgtggctct cgcggtatca ttgcagcact ggggccagat ggtaagccct    3420
cccgtatcgt agttatctac acgacgggga gtcaggcaac tatggatgaa cgaaatagac    3480
agatcgctga gataggtgcc tcactgatta agcattggta ggaattaatg atgtctcgtt    3540
tagataaaag taaagtgatt aacagcgcat tagagctgct taatgaggtc ggaatcgaag    3600
gtttaacaac ccgtaaactc gcccagaagc taggtgtaga gcagcctaca ttgtattggc    3660
atgtaaaaaa taagcgggct ttgctcgacg ccttagccat tgagatgtta dataggcacc    3720
atactcactt ttgccccttta aaggggaaa gctggcaaga ttttttacgt aataacgcta    3780
aaagttttag atgtgcttta ctaagtcatc gcgatggagc aaaagtacat ttaggtacac    3840
ggcctacaga aaaacagtat gaaactctcg aaaatcaatt agccttttta tgccaacaag    3900
gtttttcact agagaatgca ttatatgcac tcagcgcagt ggggcatttt actttaggtt    3960
gcgtattgga agatcaagag catcaagtcg ctaaagaaga aagggaaaca cctactactg    4020
atagtatgcc gccattatta cgacaagcta tcgaattatt tgatcaccaa ggtgcagagc    4080
cagccttctt attcggcctt gaattgatca tatgcggatt agaaaaacaa cttaaatgtg    4140
aaagtgggtc ttaaaagcag cataacccttt ttccgtgatg gtaacttcac tagttttaaaa    4200
ggatctaggt gaagatcctt tttgataatc tcatgaccaa aatcccttaa cgtgagtttt    4260
```

```
cgttccactg agcgtcagac cccgtagaaa agatcaaagg atcttcttga gatccttttt    4320
ttctgcgcgt aatctgctgc ttgcaaacaa aaaaaccacc gctaccagcg gtggtttgtt    4380
tgccggatca agagctacca actcttttc cgaaggtaac tggcttcagc agagcgcaga     4440
taccaaatac tgtccttcta gtgtagccgt agttaggcca ccacttcaag aactctgtag    4500
caccgcctac atacctcgct ctgctaatcc tgttaccagt ggctgctgcc agtggcgata    4560
agtcgtgtct taccgggttg gactcaagac gatagttacc ggataaggcg cagcggtcgg    4620
gctgaacggg gggttcgtgc acacagccca gcttggagcg aacgacctac accgaactga    4680
gatacctaca gcgtgagcta tgagaaagcg ccacgcttcc cgaagggaga aaggcggaca    4740
ggtatccggt aagcggcagg gtcggaacag gagagcgcac gagggagctt ccaggggggaa   4800 acgcctggta tctttatagt cctgtcgggt ttcgccacct ctgacttgag cgtcgatttt    4860
tgtgatgctc gtcaggggg cggagcctat ggaaaaacgc cagcaacgcg cctttttac     4920 ggttcctggc cttttgctgg ccttttgctc acatgacccg aca                      4963

<210> SEQ ID NO 13
<211> LENGTH: 907
<212> TYPE: DNA
<213> ORGANISM: Homo sapiens
<220> FEATURE:
<223> OTHER INFORMATION: XbaI - HindIII cassette; Start-ATG: Position
      43; FN7B8: recombinant ED-B domain flanked by adjacent type III FN
      homology repeats encoded as a cassette cloned on pASK75

<400> SEQUENCE: 13
tctagaaata attttgttta actttaagaa ggagatatac atatgccatt gtctccacca      60
acaaacttgc atctggaggc aaaccctgac actggagtgc tcacagtctc ctgggagagg     120
agcaccaccc cagacattac tggttataga attaccacaa ccctacaaa cggccagcag     180 ggaaattctt tggaagaagt ggtccatgct gatcagagct cctgcacttt tgataacctg    240
agtcccggcc tggagtacaa tgtcagtgtt tacactgtca aggatgacaa ggaaagtgtc    300
cctatctctg ataccatcat cccagaagtt ccgcagctga cagatctgtc cttcgttgac    360
atcaccgaca gctccatcgg tctgcgttgg accccgctga attcctccac catcatcggt    420
tatcgtatca ccgttgttgc tgctggtgaa gggatcccga tctttgaaga cttcgttgac    480
tcctccgttg gttactacac cgttaccggt ctggaacccg gatcgacta cgacatctcc    540 gttatcaccc tgatcaacgg tggtgaatcc gctccgacca ccttaaccca gcagaccgcg    600
gttcctcctc ccactgacct gcgattcacc aacattggtc cagacaccat gcgtgtcacc    660
tgggctccac ccccatccat tgatttaacc aacttcctgg tgcgttactc acctgtgaaa    720
aatgaggaag atgttgcaga gttgtcaatt tctccttcag acaatgcagt ggtcttaaca    780
aatctcctgc ctggtacaga atatgtagtg agtgtctcca gtgtctacga caacatgag    840 agcacacctc ttagaggaag acagaaaaca ggtagcgctc accatcacca tcaccattaa    900
taagctt                                                              907

<210> SEQ ID NO 14
<211> LENGTH: 298
<212> TYPE: PRT
<213> ORGANISM: Homo sapiens
<220> FEATURE:
<223> OTHER INFORMATION: XbaI - HindIII cassette; Start-MET: Position
      13; FN7B8: recombinant ED-B domain flanked by adjacent type III FN
      homology repeats encoded as a cassette cloned on pASK75
```

<400> SEQUENCE: 14

| | | | | | | | | | | | | | | |
|---|---|---|---|---|---|---|---|---|---|---|---|---|---|---|
| Ser | Arg | Asn | Asn | Phe | Val | Leu | Glu | Gly | Asp | Ile | His | Met | Pro | Leu | Ser |
| 1 | | | | 5 | | | | | 10 | | | | | 15 | |
| Pro | Pro | Thr | Asn | Leu | His | Leu | Glu | Ala | Asn | Pro | Asp | Thr | Gly | Val | Leu |
| | | | 20 | | | | | 25 | | | | | 30 | | |
| Thr | Val | Ser | Trp | Glu | Arg | Ser | Thr | Thr | Pro | Asp | Ile | Thr | Gly | Tyr | Arg |
| | | 35 | | | | | 40 | | | | | 45 | | | |
| Ile | Thr | Thr | Thr | Pro | Thr | Asn | Gly | Gln | Gln | Gly | Asn | Ser | Leu | Glu | Glu |
| 50 | | | | | 55 | | | | | 60 | | | | | |
| Val | Val | His | Ala | Asp | Gln | Ser | Ser | Cys | Thr | Phe | Asp | Asn | Leu | Ser | Pro |
| 65 | | | | 70 | | | | | 75 | | | | | 80 | |
| Gly | Leu | Glu | Tyr | Asn | Val | Ser | Val | Tyr | Thr | Val | Lys | Asp | Asp | Lys | Glu |
| | | | | 85 | | | | | 90 | | | | | 95 | |
| Ser | Val | Pro | Ile | Ser | Asp | Thr | Ile | Ile | Pro | Glu | Val | Pro | Gln | Leu | Thr |
| | | | 100 | | | | | 105 | | | | | 110 | | |
| Asp | Leu | Ser | Phe | Val | Asp | Ile | Thr | Asp | Ser | Ser | Ile | Gly | Leu | Arg | Trp |
| | | 115 | | | | | 120 | | | | | 125 | | | |
| Thr | Pro | Leu | Asn | Ser | Ser | Thr | Ile | Ile | Gly | Tyr | Arg | Ile | Thr | Val | Val |
| | 130 | | | | | 135 | | | | | 140 | | | | |
| Ala | Ala | Gly | Glu | Gly | Ile | Pro | Ile | Phe | Glu | Asp | Phe | Val | Asp | Ser | Ser |
| 145 | | | | | 150 | | | | | 155 | | | | | 160 |
| Val | Gly | Tyr | Tyr | Thr | Val | Thr | Gly | Leu | Glu | Pro | Gly | Ile | Asp | Tyr | Asp |
| | | | | 165 | | | | | 170 | | | | | 175 | |
| Ile | Ser | Val | Ile | Thr | Leu | Ile | Asn | Gly | Gly | Glu | Ser | Ala | Pro | Thr | Thr |
| | | | 180 | | | | | 185 | | | | | 190 | | |
| Leu | Thr | Gln | Gln | Thr | Ala | Val | Pro | Pro | Pro | Thr | Asp | Leu | Arg | Phe | Thr |
| | | 195 | | | | | 200 | | | | | 205 | | | |
| Asn | Ile | Gly | Pro | Asp | Thr | Met | Arg | Val | Thr | Trp | Ala | Pro | Pro | Pro | Ser |
| | 210 | | | | | 215 | | | | | 220 | | | | |
| Ile | Asp | Leu | Thr | Asn | Phe | Leu | Val | Arg | Tyr | Ser | Pro | Val | Lys | Asn | Glu |
| 225 | | | | | 230 | | | | | 235 | | | | | 240 |
| Glu | Asp | Val | Ala | Glu | Leu | Ser | Ile | Ser | Pro | Ser | Asp | Asn | Ala | Val | Val |
| | | | | 245 | | | | | 250 | | | | | 255 | |
| Leu | Thr | Asn | Leu | Leu | Pro | Gly | Thr | Glu | Tyr | Val | Val | Ser | Val | Ser | Ser |
| | | | 260 | | | | | 265 | | | | | 270 | | |
| Val | Tyr | Glu | Gln | His | Glu | Ser | Thr | Pro | Leu | Arg | Gly | Arg | Gln | Lys | Thr |
| | | 275 | | | | | 280 | | | | | 285 | | | |
| Gly | Ser | Ala | His | His | His | His | His | Ala | | | | | | | |
| | 290 | | | | 295 | | | | | | | | | | |

<210> SEQ ID NO 15
<211> LENGTH: 379
<212> TYPE: DNA
<213> ORGANISM: Homo sapiens
<220> FEATURE:
<223> OTHER INFORMATION: XbaI - HindIII cassette; Start-ATG: Position
43; ED-B: Recombinant ED-B domain alone encoded as a cassette
cloned on pASK75

<400> SEQUENCE: 15
tctagaaata attttgttta actttaagaa ggagatatac aaatgcgtgg ttccgaagtt    60
ccgcagctga cagatctgtc cttcgttgac atcaccgaca gctccatcgg tctgcgttgg   120
accccgctga attcctccac catcatcggt tatcgtatca ccgttgttgc tgctggtgaa   180
gggatcccga tctttgaaga cttcgttgac tcctccgttg gttactacac cgttaccggt   240

```
ctggaacccg ggatcgacta cgacatctcc gttatcaccc tgatcaacgg tggtgaatcc    300
gctccgacca ccttaaccca gcagaccgct gggagcgctc accatcacca tcaccattaa    360
gggagccacc cgcaagctt                                                  379
```

<210> SEQ ID NO 16
<211> LENGTH: 123
<212> TYPE: PRT
<213> ORGANISM: Homo sapiens
<220> FEATURE:
<223> OTHER INFORMATION: XbaI - HindIII cassette; Start-MET: Position
      13; ED-B: Recombinant ED-B domain alone encoded as a cassette
      cloned on pASK75

<400> SEQUENCE: 16

```
Ser Arg Asn Asn Phe Val Leu Glu Gly Asp Ile Gln Met Arg Gly Ser
1               5                   10                  15

Glu Val Pro Gln Leu Thr Asp Leu Ser Phe Val Asp Ile Thr Asp Ser
            20                  25                  30

Ser Ile Gly Leu Arg Trp Thr Pro Leu Asn Ser Ser Thr Ile Ile Gly
        35                  40                  45

Tyr Arg Ile Thr Val Val Ala Ala Gly Glu Gly Ile Pro Ile Phe Glu
    50                  55                  60

Asp Phe Val Asp Ser Ser Val Gly Tyr Tyr Thr Val Thr Gly Leu Glu
65                  70                  75                  80

Pro Gly Ile Asp Tyr Asp Ile Ser Val Ile Thr Leu Ile Asn Gly Gly
                85                  90                  95

Glu Ser Ala Pro Thr Thr Leu Thr Gln Gln Thr Ala Gly Ser Ala His
            100                 105                 110

His His His His His Gly Ser His Pro Gln Ala
        115                 120
```

<210> SEQ ID NO 17
<211> LENGTH: 904
<212> TYPE: DNA
<213> ORGANISM: Homo sapiens
<220> FEATURE:
<223> OTHER INFORMATION: XbaI - HindIII cassette; Start-ATG: Position
      43; FN789: recombinant Type III FN homology repeats without ED-B
      encoded as a cassette cloned on pASK75

<400> SEQUENCE: 17

```
tctagaaata attttgttta actttaagaa ggagatatac atatgccatt gtctccacca    60
acaaacttgc atctggaggc aaaccctgac actggagtgc tcacagtctc ctggagagg    120 agcaccaccc cagacattac tggttataga attaccacaa cccctacaaa cggccagcag   180
ggaaattctt tggaagaagt ggtccatgct gatcagagct cctgcacttt tgataacctg    240
agtcccggcc tggagtacaa tgtcagtgtt tacactgtca aggatgacaa ggaaagtgtc   300
cctatctctg ataccatcat cccagctgtt cctcctccca ctgacctgcg attcaccaac    360
attggtccag acaccatgcg tgtcacctgg gctccacccc catccattga tttaaccaac    420
ttcctggtgc gttactcacc tgtgaaaaat gaggaagatg ttgcagagtt gtcaatttct    480
ccttcagaca atgcagtggt cttaacaaat ctcctgcctg gtacagaata tgtagtgagt    540
gtctccagtg tctacgaaca acatgagagc acacctctta aggaagaca gaaaacaggt   600 cttgattccc caactggcat tgactttttct gatattactg ccaactcttt tactgtgcac    660
tggattgctc ctcgagccac catcactggc tacaggatcc gccatcatcc cgagcacttc    720
agtgggagac ctcgagaaga tcgggtgccc cactctcgga attccatcac cctcaccaac    780
```

-continued

```
ctcactccag gcacagagta tgtggtcagc atcgttgctc ttaatggcag agaggaaagt    840
cccttattga ttggccaaca atcaacagtt agcgctcacc atcaccatca ccattaataa    900
gctt                                                                904
```

<210> SEQ ID NO 18
<211> LENGTH: 297
<212> TYPE: PRT
<213> ORGANISM: Homo sapiens
<220> FEATURE:
<223> OTHER INFORMATION: XbaI - HindIII cassette; Start-MET: Position
      13; FN789: recombinant Type III FN homology repeats without ED-B
      encoded as a cassette cloned on pASK75

<400> SEQUENCE: 18

```
Ser Arg Asn Asn Phe Val Leu Glu Gly Asp Ile His Met Pro Leu Ser
1               5                   10                  15

Pro Pro Thr Asn Leu His Leu Glu Ala Asn Pro Asp Thr Gly Val Leu
                20                  25                  30

Thr Val Ser Trp Glu Arg Ser Thr Thr Pro Asp Ile Thr Gly Tyr Arg
            35                  40                  45

Ile Thr Thr Thr Pro Thr Asn Gly Gln Gln Gly Asn Ser Leu Glu Glu
        50                  55                  60

Val Val His Ala Asp Gln Ser Ser Cys Thr Phe Asp Asn Leu Ser Pro
65                  70                  75                  80

Gly Leu Glu Tyr Asn Val Ser Val Tyr Thr Val Lys Asp Asp Lys Glu
                85                  90                  95

Ser Val Pro Ile Ser Asp Thr Ile Ile Pro Ala Val Pro Pro Pro Thr
            100                 105                 110

Asp Leu Arg Phe Thr Asn Ile Gly Pro Asp Thr Met Arg Val Thr Trp
        115                 120                 125

Ala Pro Pro Pro Ser Ile Asp Leu Thr Asn Phe Leu Val Arg Tyr Ser
130                 135                 140

Pro Val Lys Asn Glu Glu Asp Val Ala Glu Leu Ser Ile Ser Pro Ser
145                 150                 155                 160

Asp Asn Ala Val Val Leu Thr Asn Leu Leu Pro Gly Thr Glu Tyr Val
                165                 170                 175

Val Ser Val Ser Ser Val Tyr Glu Gln His Glu Ser Thr Pro Leu Arg
            180                 185                 190

Gly Arg Gln Lys Thr Gly Leu Asp Ser Pro Thr Gly Ile Asp Phe Ser
        195                 200                 205

Asp Ile Thr Ala Asn Ser Phe Thr Val His Trp Ile Ala Pro Arg Ala
    210                 215                 220

Thr Ile Thr Gly Tyr Arg Ile Arg His His Pro Glu His Phe Ser Gly
225                 230                 235                 240

Arg Pro Arg Glu Asp Arg Val Pro His Ser Arg Asn Ser Ile Thr Leu
                245                 250                 255

Thr Asn Leu Thr Pro Gly Thr Glu Tyr Val Val Ser Ile Val Ala Leu
            260                 265                 270

Asn Gly Arg Glu Glu Ser Pro Leu Leu Ile Gly Gln Gln Ser Thr Val
        275                 280                 285

Ser Ala His His His His His Ala
    290                 295
```

<210> SEQ ID NO 19
<211> LENGTH: 534

<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: N7A: Mutein of hNGAL specific for ED-B of fibronectin cloned on phNGAL98

<400> SEQUENCE: 19

```
caggactcca cctcagacct gatcccagcc ccacctctga gcaaggtccc tctgcagcag      60
aacttccagg acaaccaatt ccatgggaaa tggtatgtcg tgggcaaagc cggaaatcac     120
gacctgcgtg aggataagga tccgcgtaaa atgcaagcga ccatttacga gttgaaagaa     180
gataaatcat ataacgtcac caatgtgcgt tttgttcaca gaaatgcaa ttaccgtatt      240
tggacctttg tgccggggag ccagccgggc gagtttactt taggcaatat taaaagttgg    300
ccgggcctga catcatggtt ggtccgcgtc gtgagcacca actacaacca gcatgccatg    360
gtgttcttca gcgtgtgta ccagaaccgc gagctgtttg agatcacact gtacgggcgc      420
acgaaagaac tgacaaacga gctgaaggaa aattttatcc gcttttccaa atctctgggc   480
ctccctgaaa accacatcgt cttccctgtc ccaatcgacc agtgtatcga cggc           534
```

<210> SEQ ID NO 20
<211> LENGTH: 178
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: N7A: Mutein of hNGAL specific for ED-B of fibronectin cloned on phNGAL98

<400> SEQUENCE: 20

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Lys Ala Gly Asn His Asp Leu Arg Glu Asp Lys Asp Pro
        35                  40                  45

Arg Lys Met Gln Ala Thr Ile Tyr Glu Leu Lys Glu Asp Lys Ser Tyr
    50                  55                  60

Asn Val Thr Asn Val Arg Phe Val His Lys Lys Cys Asn Tyr Arg Ile
65                  70                  75                  80

Trp Thr Phe Val Pro Gly Ser Gln Pro Gly Glu Phe Thr Leu Gly Asn
                85                  90                  95

Ile Lys Ser Trp Pro Gly Leu Thr Ser Trp Leu Val Arg Val Val Ser
            100                 105                 110

Thr Asn Tyr Asn Gln His Ala Met Val Phe Phe Lys Arg Val Tyr Gln
        115                 120                 125

Asn Arg Glu Leu Phe Glu Ile Thr Leu Tyr Gly Arg Thr Lys Glu Leu
    130                 135                 140

Thr Asn Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 21
<211> LENGTH: 534
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: N7E: Mutein of hNGAL specific for ED-B of fibronectin cloned on phNGAL98

<400> SEQUENCE: 21

```
caggactcca cctcagacct gatcccagcc ccacctctga gcaaggtccc tctgcagcag      60
aacttccagg acaaccaatt ccatgggaaa tggtatgtcg tgggcgaggc cggaaatagc     120
ctgctgcgtg aggataagga tccgcgtaaa atgtacgcga ccatttacga gttgaaagaa     180
gataaatcat ataacgtcac cagcgtgcgt tttcgtagca agaaatgcca ctacctgatt     240
cgtacctttg tgccggggag ccagccgggc gagtttactt taggcctgat taaaagtaaa     300
ccgggccaca catcattctt ggtccgcgtt gtgagcacca actacaacca gcatgccatg     360
gtgttcttca agaccgtggc acagaaccgc gagtactttt tcatcacact gtacgggcgc     420
acgaaagaac tgacaagcga gctgaaggaa aattttatcc gcttttccaa atctctgggc     480
ctccctgaaa accacatcgt cttccctgtc ccaatcgacc agtgtatcga cggc           534
```

<210> SEQ ID NO 22
<211> LENGTH: 178
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: N7E: Mutein of hNGAL specific for ED-B of fibronectin cloned on phNGAL98

<400> SEQUENCE: 22

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Glu Ala Gly Asn Ser Leu Leu Arg Glu Asp Lys Asp Pro
        35                  40                  45

Arg Lys Met Tyr Ala Thr Ile Tyr Glu Leu Lys Glu Asp Lys Ser Tyr
    50                  55                  60

Asn Val Thr Ser Val Arg Phe Arg Ser Lys Lys Cys His Tyr Leu Ile
65                  70                  75                  80

Arg Thr Phe Val Pro Gly Ser Gln Pro Gly Glu Phe Thr Leu Gly Leu
                85                  90                  95

Ile Lys Ser Lys Pro Gly His Thr Ser Phe Leu Val Arg Val Val Ser
            100                 105                 110

Thr Asn Tyr Asn Gln His Ala Met Val Phe Phe Lys Thr Val Ala Gln
        115                 120                 125

Asn Arg Glu Tyr Phe Phe Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 23
<211> LENGTH: 534
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: N9B: Mutein of hNGAL specific for ED-B of fibronectin cloned on phNGAL98

<400> SEQUENCE: 23

```
caggactcca cctcagacct gatcccagcc ccacctctga gcaaggtccc tctgcagcag      60
aacttccagg acaaccaatt ccatgggaaa tggtatgtcg tgggccgtgc cggaaatatg     120
cgtctgcgtg aggataagga tccggcaaaa atggttgcga ccatttacga gttgaaagaa     180
gataaatcat ataacgtcac caaagtgatg tttcaacgta agaaatgcaa atacatgatt     240
aataccttg tgccggggag ccagccgggc gagtttactt taggcgcaat taaaagtcct      300
ccgggcccta catcaacctt ggtccgcgtc gtgagcacca actacaacca gcatgccatg     360
gtgttcttca gcacgtgtt ccagaaccgc gagtactttc acatcacact gtacgggcgc      420
acgaaagaac tgacaagcga gctgaaggaa aattttatcc gcttttccaa atctctgggc     480
ctccctgaaa accacatcgt cttccctgtc ccaatcgacc agtgtatcga cggc           534
```

<210> SEQ ID NO 24
<211> LENGTH: 178
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: N9B: Mutein of hNGAL specific for ED-B of fibronectin cloned on phNGAL98

<400> SEQUENCE: 24

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Arg Ala Gly Asn Met Arg Leu Arg Glu Asp Lys Asp Pro
        35                  40                  45

Ala Lys Met Val Ala Thr Ile Tyr Glu Leu Lys Glu Asp Lys Ser Tyr
    50                  55                  60

Asn Val Thr Lys Val Met Phe Gln Arg Lys Lys Cys Lys Tyr Met Ile
65                  70                  75                  80

Asn Thr Phe Val Pro Gly Ser Gln Pro Gly Glu Phe Thr Leu Gly Ala
                85                  90                  95

Ile Lys Ser Pro Pro Gly Pro Thr Ser Thr Leu Val Arg Val Val Ser
            100                 105                 110

Thr Asn Tyr Asn Gln His Ala Met Val Phe Phe Lys His Val Phe Gln
        115                 120                 125

Asn Arg Glu Tyr Phe His Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175
```

<210> SEQ ID NO 25
<211> LENGTH: 534
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: N10D: Mutein of hNGAL specific for ED-B of fibronectin cloned on phNGAL98

<400> SEQUENCE: 25

```
caggactcca cctcagacct gatcccagcc ccacctctga gcaaggtccc tctgcagcag    60
aacttccagg acaaccaatt ccatgggaaa tggtatgtcg tgggcgcagc cggaaatacc   120
tggctgcgtg aggataagga tccgtacaaa atgcaagcga ccatttacga gttgaaagaa   180
gataaatcat ataacgtcac caatgtgctg tttatgagca agaaatgccg ttacatgatt   240
cacacctttg tgccggggag ccagccgggc gagtttactt taggcagcat taaaagttgg   300
ccgggcctga tcatggttg gtccgcgtc gtgagcacca actacaacca gcatgccatg   360
gtgttcttca gcgtgtgta ccagaaccgc gagttctttg gaatcacact gtacgggcgc   420
acgaaagaac tgacaagcga gctgaaggaa aattttatcc gcttttccaa atctctgggc   480
ctccctgaaa accacatcgt cttccctgtc ccaatcgacc agtgtatcga cggc         534
```

<210> SEQ ID NO 26
<211> LENGTH: 178
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: N10D: Mutein of hNGAL specific for ED-B of fibronectin cloned on phNGAL98

<400> SEQUENCE: 26

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Ala Ala Gly Asn Thr Trp Leu Arg Glu Asp Lys Asp Pro
        35                  40                  45

Tyr Lys Met Gln Ala Thr Ile Tyr Glu Leu Lys Glu Asp Lys Ser Tyr
    50                  55                  60

Asn Val Thr Asn Val Leu Phe Met Ser Lys Lys Cys Arg Tyr Met Ile
65                  70                  75                  80

His Thr Phe Val Pro Gly Ser Gln Pro Gly Glu Phe Thr Leu Gly Ser
                85                  90                  95

Ile Lys Ser Trp Pro Gly Leu Thr Ser Trp Leu Val Arg Val Val Ser
            100                 105                 110

Thr Asn Tyr Asn Gln His Ala Met Val Phe Phe Lys Arg Val Tyr Gln
        115                 120                 125

Asn Arg Glu Phe Phe Gly Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160
```

```
Leu Pro Glu Asn His Ile Val Phe Pro Val Pro Ile Asp Gln Cys Ile
            165                 170                 175

Asp Gly

<210> SEQ ID NO 27
<211> LENGTH: 3745
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Expression vector phNGAL98 with AmpR encoding
      wild type Lcn2 with the C-terminal Strep-tagII

<400> SEQUENCE: 27
ccatcgaatg gccagatgat taattcctaa ttttttgttga cactctatca ttgatagagt     60
tattttacca ctccctatca gtgatagaga aaagtgaaat gaatagttcg acaaaaatct    120
agataacgag ggcaaaaaat gaaaagaca gctatcgcga ttgcagtggc tctggctggc    180
ttcgctaccg tagcgcaggc ccaggactcc acctcagacc tgatcccagc cccacctctg    240
agcaaggtcc ctctgcagca gaacttccag gacaaccaat ccatgggaa gtggtatgtg    300 gtaggtctcg cagggaatgc aattctcaga gaagacaaag acccgcaaaa gatgtatgcc    360
accatctatg agctgaaaga agacaagagc tacaatgtca cctccgtcct gtttaggaaa    420
aagaagtgtg actactggat caggacttt gttccaggtt cccagccagg cgagttcacg    480
ctgggcaaca ttaagagtta ccctggatta acgagttacc tcgtccgagt ggtgagcacc    540
aactacaacc agcatgctat ggtgttcttc aagaaagttt ctcaaaacag ggagtacttc    600
aagatcaccc tctacgggag aaccaaggag ctgacttcgg aactaaagga gaacttcatc    660
cgcttctcca atctctgggg cctccctgaa aaccacatcg tcttccctgt cccaatcgac    720
cagtgtatcg acggcagcgc ttggtctcac ccgcagttcg aaaaataata gcttgacct    780 gtgaagtgaa aaatggcgca cattgtgcga cattttttt gtctgccgtt taccgctact    840
gcgtcacgga tctccacgcg ccctgtagcg gcgcattaag cgcggcgggt gtggtggtta    900
cgcgcagcgt gaccgctaca cttgccagcg ccctagcgcc cgctcctttc gctttcttcc    960
cttcctttct cgccacgttc gccggctttc ccgtcaagc tctaaatcgg gggctcccttt   1020 tagggttccg atttagtgct ttacggcacc tcgaccccaa aaaacttgat tagggtgatg   1080
gttcacgtag tgggccatcg ccctgataga cggtttttcg ccctttgacg ttggagtcca   1140
cgttctttaa tagtggactc ttgttccaaa ctggaacaac actcaaccct atctcggtct   1200
attcttttga tttataaggg attttgccga tttcggccta ttggttaaaa aatgagctga   1260
tttaacaaaa atttaacgcg aattttaaca aatattaac gttacaatt tcaggtggca   1320 cttttcgggg aaatgtgcgc ggaaccccta tttgtttatt tttctaaata cattcaaata   1380
tgtatccgct catgagacaa taaccctgat aaatgcttca ataatattga aaaggaaga   1440 gtatgagtat tcaacatttc cgtgtcgccc ttattccctt ttttgcggca ttttgccttc   1500 ctgttttttgc tcacccagaa acgctggtga agtaaaaga tgctgaagat cagttgggtg   1560
cacgagtggg ttacatcgaa ctggatctca acagcggtaa gatccttgag agttttcgcc   1620
ccgaagaacg ttttccaatg atgagcactt ttaaagttct gctatgtggc gcggtattat   1680
cccgtattga cgccgggcaa gagcaactcg gtcgccgcat acactattct cagaatgact   1740
tggttgagta ctcaccagtc acagaaaagc atcttacgga tggcatgaca gtaagagaat   1800
```

```
tatgcagtgc tgccataacc atgagtgata acactgcggc aacttactt ctgacaacga    1860 tcggaggacc gaaggagcta accgcttttt tgcacaacat gggggatcat gtaactcgcc    1920
ttgatcgttg ggaaccggag ctgaatgaag ccataccaaa cgacgagcgt gacaccacga    1980
tgcctgtagc aatggcaaca acgttgcgca aactattaac tggcgaacta cttactctag    2040
cttcccggca caattgata gactggatgg aggcggataa agttgcagga ccacttctgc     2100
gctcggccct tccggctggc tggtttattg ctgataaatc tggagccggt gagcgtggct    2160
ctcgcggtat cattgcagca ctggggccag atggtaagcc ctcccgtatc gtagttatct    2220
acacgacggg gagtcaggca actatggatg aacgaaatag acagatcgct gagataggtg    2280
cctcactgat taagcattgg taggaattaa tgatgtctcg tttagataaa agtaaagtga    2340
ttaacagcgc attagagctg cttaatgagg tcggaatcga aggtttaaca acccgtaaac    2400
tcgcccagaa gctaggtgta gagcagccta cattgtattg gcatgtaaaa ataagcggg     2460 cttttgctcga cgccttagcc attgagatgt tagataggca ccatactcac ttttgcccctt  2520 tagaagggga aagctggcaa gattttttac gtaataacgc taaaagtttt agatgtgctt    2580
tactaagtca tcgcgatgga gcaaaagtac atttaggtac acggcctaca gaaaaacagt    2640
atgaaactct cgaaaatcaa ttagcctttt tatgccaaca aggttttttca ctagagaatg   2700 cattatatgc actcagcgca gtggggcatt ttactttagg ttgcgtattg aagatcaag     2760 agcatcaagt cgctaaagaa gaagggaaa cacctactac tgatagtatg ccgccattat     2820
tacgacaagc tatcgaatta tttgatcacc aaggtgcaga gccagccttc ttattcggcc    2880
ttgaattgat catatgcgga ttagaaaaac aacttaaatg tgaaagtggg tcttaaaagc    2940 agcataaccct ttttccgtga tggtaacttc actagtttaa aaggatctag gtgaagatcc   3000
tttttgataa tctcatgacc aaaatccctt aacgtgagtt ttcgttccac tgagcgtcag    3060
accccgtaga aaagatcaaa ggatcttctt gagatccttt ttttctgcgc gtaatctgct    3120
gcttgcaaac aaaaaaacca ccgctaccag cggtggtttg tttgccggat caagagctac    3180
caactctttt tccgaaggta actggcttca gcagagcgca gataccaaat actgtccttc    3240
tagtgtagcc gtagttaggc caccacttca agaactctgt agcaccgcct acatacctcg    3300
ctctgctaat cctgttacca gtggctgctg ccagtggcga taagtcgtgt cttaccgggt    3360
tggactcaag acgatagtta ccggataagg cgcagcggtc gggctgaacg ggggggttcgt   3420 gcacacagcc cagcttggag cgaacgacct acaccgaact gagataccta cagcgtgagc    3480
tatgagaaag cgccacgctt cccgaaggga gaaaggcgga caggtatccg gtaagcggca    3540
gggtcggaac aggagagcgc acgagggagc ttccaggggg aaacgcctgg tatctttata    3600
gtcctgtcgg gtttcgccac ctctgacttg agcgtcgatt tttgtgatgc tcgtcagggg    3660
ggcggagcct atggaaaaac gccagcaacg cggccttttt acggttcctg gccttttgct    3720
ggccttttgc tcacatgacc cgaca                                           3745
```

<210> SEQ ID NO 28  
<211> LENGTH: 178  
<212> TYPE: PRT  
<213> ORGANISM: Artificial Sequence  
<220> FEATURE:  
<223> OTHER INFORMATION: Description of Artificial Sequence: Synthetic polypeptide  
<220> FEATURE:  
<223> OTHER INFORMATION: Wild type Lcn2 cloned on phNGAL98 without OmpA signal peptide and Strep-tagII

<400> SEQUENCE: 28

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
        50                  55                  60

Asn Val Thr Ser Val Leu Phe Arg Lys Lys Lys Cys Asp Tyr Trp Ile
65                  70                  75                  80

Arg Thr Phe Val Pro Gly Ser Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 29
<211> LENGTH: 40
<212> TYPE: PRT
<213> ORGANISM: Homo sapiens
<220> FEATURE:
<223> OTHER INFORMATION: peptide sequence of A beta 40

<400> SEQUENCE: 29

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 30
<211> LENGTH: 11
<212> TYPE: PRT
<213> ORGANISM: Homo sapiens
<220> FEATURE:
<223> OTHER INFORMATION: peptide sequence of A beta 1-11

<400> SEQUENCE: 30

Asp Ala Glu Phe Arg His Asp Ser Gly Tyr Glu
1               5                   10

<210> SEQ ID NO 31
<211> LENGTH: 12
<212> TYPE: PRT
<213> ORGANISM: Homo sapiens
<220> FEATURE:
<223> OTHER INFORMATION: peptide sequence of A beta 16-27

<400> SEQUENCE: 31

Lys Leu Val Phe Phe Ala Glu Asp Val Gly Ser Asn
```

<210> SEQ ID NO 32
<211> LENGTH: 1182
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: XbaI HindIII DNA restriction fragment of pMBP-His. Reading frame starts at position 27 with atg

<400> SEQUENCE: 32

```
tctagaacca acaaggacca tagcatatga aaayygaaga aggtaaactg gtaatctgga      60
ttaacggcga taaaggctat aacggtctcg ctgaagtcgg taagaaattc gagaaagata     120
ccggaattaa agtcaccgtt gagcatccgg ataaactgga agagaaattc ccacaggttg     180
cggcaactgg cgatggccct gacattatct tctgggcaca cgaccgcttt ggtggctacg     240
ctcaatctgg cctgttggct gaaatcaccc cggacaaagc gttccaggac aagctgtatc     300
cgtttacctg ggatgccgta cgttacaacg gcaagctgat tgcttacccg atcgctgttg     360
aagcgttatc gctgatttat aacaaagatc tgctgccgaa cccgccaaaa acctgggaag     420
agatcccggc gctggataaa gaactgaaag cgaaaggtaa gagcgcgctg atgttcaacc     480
tgcaagaacc gtacttcacc tggccgctga ttgctgctga cggggggttat gcgttcaagt     540
atgaaaacgg caagtacgac attaaagacg tgggcgtgga taacgctggc gcgaaagcgg     600
gtctgacctt cctggttgac ctgattaaaa acaaacacat gaatgcagac accgattact     660
ccatcgcaga agctgccttt aataaaggcg aaacagcgat gaccatcaac ggcccgtggg     720
catggtccaa catcgacacc agcaaagtga attatggtgt aacggtactg ccgaccttca     780
agggtcaacc atccaaaccg ttcgttggcg tgctgagcgc aggtattaac gccgccagtc     840
cgaacaaaga gctggcgaaa gagttcctcg aaaactatct gctgactgat gaaggtctgg     900
aagcggttaa taaagacaaa ccgctgggtg ccgtagcgct gaagtcttac gaggaagagt     960
tggcgaaaga tccacgtatt gccgccacca tggaaaacgc ccagaaaggt gaaatcatgc    1020
cgaacatccc gcagatgtcc gctttctggt atgccgtgcg tactgcggtg atcaacgccg    1080
ccagcggtcg tcagactgtc gatgaagccc tgaaagacgc gcagactcgt atcacccagg    1140
gatccctcga gatcaaacat caccaccatc accattaagc tt                       1182
```

<210> SEQ ID NO 33
<211> LENGTH: 1308
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: XbaI HindIII DNA restriction fragment pASK75-MBP-Abeta40. Reading frame starts at position 27 with atg

<400> SEQUENCE: 33

```
tctagaacca acaaggacca tagcatatga aaayygaaga aggtaaactg gtaatctgga      60
ttaacggcga taaaggctat aacggtctcg ctgaagtcgg taagaaattc gagaaagata     120
ccggaattaa agtcaccgtt gagcatccgg ataaactgga agagaaattc ccacaggttg     180
cggcaactgg cgatggccct gacattatct tctgggcaca cgaccgcttt ggtggctacg     240
ctcaatctgg cctgttggct gaaatcaccc cggacaaagc gttccaggac aagctgtatc     300
```

```
cgtttacctg ggatgccgta cgttacaacg gcaagctgat tgcttacccg atcgctgttg      360
aagcgttatc gctgatttat aacaaagatc tgctgccgaa cccgccaaaa acctgggaag      420
agatcccggc gctggataaa gaactgaaag cgaaaggtaa gagcgcgctg atgttcaacc      480
tgcaagaacc gtacttcacc tggccgctga ttgctgctga cggggggttat gcgttcaagt      540 atgaaaacgg caagtacgac attaagacg tgggcgtgga taacgctggc gcgaaagcgg      600
gtctgacctt cctggttgac ctgattaaaa acaaacacat gaatgcagac accgattact      660
ccatcgcaga agctgccttt aataaaggcg aaacagcgat gaccatcaac ggcccgtggg      720
catggtccaa catcgacacc agcaaagtga attatggtgt aacggtactg ccgaccttca      780
agggtcaacc atccaaaccg ttcgttggcg tgctgagcgc aggtattaac gccgccagtc      840
cgaacaaaga gctggcgaaa gagttcctcg aaaactatct gctgactgat gaaggtctgg      900
aagcggttaa taaagacaaa ccgctgggtg ccgtagcgct gaagtcttac gaggaagagt      960
tggcgaaaga tccacgtatt gccgccacca tggaaaacgc ccagaaaggt gaaatcatgc     1020
cgaacatccc gcagatgtcc gctttctggt atgccgtgcg tactgcggtg atcaacgccg     1080
ccagcggtcg tcagactgtc gatgaagccc tgaaagacgc gcagactcgt atcacccagg     1140
gatcccatca ccaccatcat cacgagaact tgtacttcca ggacgctgaa ttccgtcacg     1200
actccggtta cgaagttcac caccagaagc tggttttctt cgctgaagac gttggttcca     1260
acaaaggtgc tatcatcggt ctgatggttg gtggtgttgt ttaagctt                1308
```

<210> SEQ ID NO 34
<211> LENGTH: 488
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: XbaI HindIII DNA restriction fragment of
      pASK75-TrxAbeta28H6. Reading frame starts at position 23 with atg

<400> SEQUENCE: 34

```
tctagatact gtggagttat atatgagcga taaaattatt cacctgactg acgacagttt       60
tgacacggat gtactcaaag cggacggggc gatcctcgtc gatttctggg cagagtggtg      120
cggtccgggt ggtggtgacg ctgaattccg tcacgactcc ggttacgaag ttcaccacca      180
gaaactggtg ttcttcgctg aagacgttgg ttccaacaaa ggtggcggtc cgtgcaaaat      240
gatcgccccg attctggatg aaatcgctga cgaatatcag ggcaaactga ccgttgcaaa      300
actgaacatc gatcaaaacc ctggcactgc gccgaaatat ggcatccgtg gtatcccgac      360
tctgctgctg ttcaaaaacg gtgaagtggc ggcaaccaaa gtgggtgcac tgtctaaagg      420
tcagttgaaa gagttcctcg acgctaacct ggccagcgct caccatcacc atcaccatta      480
ataagctt                                                              488
```

<210> SEQ ID NO 35
<211> LENGTH: 383
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: XbaI HindIII DNA restriction fragment of
      pASK75-TrxH6. Reading frame starts at position 23 with atg

<400> SEQUENCE: 35

```
tctagatact gtggagttat atatgagcga taaaattatt cacctgactg acgacagttt      60
tgacacggat gtactcaaag cggacggggc gatcctcgtc gatttctggg cagagtggtg     120
cggtccgtgc aaaatgatcg ccccgattct ggatgaaatc gctgacgaat atcagggcaa     180
actgaccgtt gcaaaactga acatcgatca aaaccctggc actgcgccga aatatggcat     240
ccgtggtatc ccgactctgc tgctgttcaa aaacggtgaa gtggcggcaa ccaaagtggg     300
tgcactgtct aaaggtcagt tgaaagagtt cctcgacgct aacctggcca gcgctcacca     360
tcaccatcac cattaataag ctt                                             383
```

<210> SEQ ID NO 36
<211> LENGTH: 534
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: DNA sequence for the mature protein wt Lcn2 without Strep-tag II. Reading frame starts with the first nucleotide of the following sequence

<400> SEQUENCE: 36

```
caggactcca cctcagacct gatcccagcc ccacctctga gcaaggtccc tctgcagcag      60
aacttccagg acaaccaatt ccatgggaag tggtatgtgg taggtctcgc agggaatgca     120
attctcagag aagacaaaga cccgcaaaag atgtatgcca ccatctatga gctgaaagaa     180
gacaagagct acaatgtcac ctccgtcctg tttaggaaaa agaagtgtga ctactggatc     240
aggacttttg ttccaggttc ccagccaggc gagttcacgc tgggcaacat taagagttac     300
cctggattaa cgagttacct cgtccgagtg gtgagcacca actacaacca gcatgctatg     360
gtgttcttca agaagtttc tcaaaacagg gagtacttca agatcacccct ctacgggaga     420 accaaggagc tgacttcgga actaaaggag aacttcatcc gcttctccaa atctctgggc     480
ctccctgaaa accacatcgt cttccctgtc ccaatcgacc agtgtatcga cggc            534
```

<210> SEQ ID NO 37
<211> LENGTH: 534
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: DNA sequence for the mature protein H1-G1 without Strep-tag II. Reading frame starts with the first nucleotide of the following sequence

<400> SEQUENCE: 37

```
caggactcca cctcagacct gatcccagcc ccacctctga gcaaggtccc tctgcagcag      60
aacttccagg acaaccaatt ccatgggaag tggtatgtgg taggttgtgc agggaatgtg     120
ttgctcagag aagacaaaga cccgcttaag atgtatgcca ccatctatga gctgaaagaa     180
gacaagagct acaatgtcac cagtgtcggg tttgatgata agaagtgttt gtacaagatc     240
cggacttttg ttccaggttc ccagccaggc gagttcacgc tgggcaggat taagagtgag     300
cctggaggta cgagttggct cgtccgagtg gtgagcacca actacaacca gcatgctatg     360
gtgttcttca aggaggttgc gcaaaacagg gagacgttca atatcaccct ctacgggaga     420
accaaggagc tgacttcgga actaaaggag aacttcatcc gcttctccaa atctctgggc     480
```
ctccctgaaa accacatcgt cttccctgtc ccaatcgacc agtgtatcga cggc      534

<210> SEQ ID NO 38
<211> LENGTH: 534
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA sequence for the mature protein S1-A4
      without Strep-tag II. Reading frame starts with the first
      nucleotide of the following sequence

<400> SEQUENCE: 38
caggactcca cctcagacct gatcccagcc ccacctctga gcaaggtccc tctgcagcag      60
aacttccagg acaaccaatt ccatgggaag tggtatgtgg taggtgttgc agggaattat     120
acgctcagag aagacaaaga cccgctgaag atgtatgcca ccatctatga gctgaaagaa     180
gacaagagct acaatgtcac cagtgtcggg tttaggttga agaagtgtaa ttacaagatc     240 cggactttg ttccaggttc ccagccaggc gagttcacgc tgggcattat taagagtcag     300
cctggaatga cgagttatct cgtccgagtg gtgagcacca actacaacca gcatgctatg     360
gtgttcttca agacggttgg gcaaaacagg gagatgttca atatcaccct ctacggagga     420
accaaggagc tgacttcgga actaaaggag aacttcatcc gcttctccaa atctctgggc     480
ctccctgaaa accacatcgt cttccctgtc ccaatcgacc agtgtatcga cggc      534

<210> SEQ ID NO 39
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: S1-A4 (Abeta)

<400> SEQUENCE: 39

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Tyr Thr Leu Arg Glu Asp Lys Asp Pro
        35                  40                  45

Leu Lys Met Tyr Ala Thr Ile Tyr Glu Leu Lys Glu Asp Lys Ser Tyr
    50                  55                  60

Asn Val Thr Ser Val Gly Phe Arg Leu Lys Lys Cys Asn Tyr Lys Ile
65                  70                  75                  80

Arg Thr Phe Val Pro Gly Ser Gln Pro Gly Glu Phe Thr Leu Gly Ile
                85                  90                  95

Ile Lys Ser Gln Pro Gly Met Thr Ser Tyr Leu Val Arg Val Val Ser
            100                 105                 110

Thr Asn Tyr Asn Gln His Ala Met Val Phe Phe Lys Thr Val Gly Gln
        115                 120                 125

Asn Arg Glu Met Phe Asn Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

```
Leu Pro Glu Asn His Ile Val Phe Pro Val Pro Ile Asp Gln Cys Ile
            165                 170                 175

Asp Gly
```

<210> SEQ ID NO 40
<211> LENGTH: 534
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA sequence for the mature protein US7 without
      Strep-tag II. Reading frame starts with the first nucleotide of
      the following sequence

<400> SEQUENCE: 40

```
caggactcca cctcagacct gatcccagcc ccacctctga gcaaggtccc tctgcagcag      60
aacttccagg acaaccaatt ccatgggaag tggtatgtgg taggtgttgc agggaataag     120
tctctcagag aagacaaaga cccgtggaag atgtatgcca ccatctatga gctgaaagaa     180
gacaagagct acaatgtcac ctcggtcggg tttgggacta agaagtgtca ttacaagatc     240
aggacttttg ttccaggttc ccagccaggc gagttcacgc tgggcaggat taagagtcgg     300
cctggaagga cgagtgctct cgtccgagtg gtgagcacca actacaacca gcatgctatg     360
gtgttcttca aggtggttca gcaaaacagg gagtcgttca atatcaccct ctacgggaga     420
accaaggagc tgacttcgga actaaaggag aacttcatcc gcttctccaa atctctgggc     480
ctccctgaaa accacatcgt cttccctgtc ccaatcgacc agtgtatcga cggc           534
```

<210> SEQ ID NO 41
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: US7 (Abeta)

<400> SEQUENCE: 41

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Lys Ser Leu Arg Glu Asp Lys Asp Pro
        35                  40                  45

Trp Lys Met Tyr Ala Thr Ile Tyr Glu Leu Lys Glu Asp Lys Ser Tyr
    50                  55                  60

Asn Val Thr Ser Val Gly Phe Gly Thr Lys Lys Cys His Tyr Lys Ile
65                  70                  75                  80

Arg Thr Phe Val Pro Gly Ser Gln Pro Gly Glu Phe Thr Leu Gly Arg
                85                  90                  95

Ile Lys Ser Arg Pro Gly Arg Thr Ser Ala Leu Val Arg Val Ser
            100                 105                 110

Thr Asn Tyr Asn Gln His Ala Met Val Phe Phe Lys Val Val Gln Gln
        115                 120                 125

Asn Arg Glu Ser Phe Asn Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
```

```
145                 150                 155                 160
Leu Pro Glu Asn His Ile Val Phe Pro Val Pro Ile Asp Gln Cys Ile
                165                 170                 175

Asp Gly

<210> SEQ ID NO 42
<211> LENGTH: 805
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: XbaI/HindIII restriction fragment of phNGAL124,
      which encodes wild type Lcn2 as fusion with the albumin-binding
      domain cloned on pASK75. Reading frame starts at position 22 with
      atg

<400> SEQUENCE: 42
tctagataac gagggcaaaa aatgaaaaag acagctatcg cgattgcagt ggctctggct      60
ggcttcgcta ccgtagcgca ggcccaggac tccacctcag acctgatccc agccccacct     120
ctgagcaagg tccctctgca gcagaacttc caggacaacc aattccatgg gaagtggtat     180
gtggtaggtc tcgcagggaa tgcaattctc agagaagaca agacccgca aagatgtat      240 gccaccatct atgagctgaa agaagacaag agctacaatg tcacctccgt cctgtttagg     300
aaaaagaagt gtgactactg gatcaggact tttgttccag gttcccagcc aggcgagttc     360
acgctgggca acattaagag ttaccctgga ttaacgagtt acctcgtccg agtggtgagc     420
accaactaca accagcatgc tatggtgttc ttcaagaaag tttctcaaaa cagggagtac     480
ttcaagatca ccctctacgg gagaaccaag gagctgactt cggaactaaa ggagaacttc     540
atccgcttct ccaaatctct gggcctccct gaaaaccaca tcgtcttccc tgtcccaatc     600
gaccagtgta tcgacggcag cgcttggtcc cacccgcagt cgaaaaata ggcccacctg     660 gctgaagcta aagttctggc taaccgtgaa ctggacaaat acggtgtttc cgactactac     720
aaaaacctca tcaacaacgc taaaaccgtt gaaggtgtta agctctgat cgacgaaatt     780 ctcgcagcac tgccgtaata agctt                                          805

<210> SEQ ID NO 43
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: H1-G1 (Abeta)

<400> SEQUENCE: 43

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Cys Ala Gly Asn Val Leu Leu Arg Glu Asp Lys Asp Pro
        35                  40                  45

Leu Lys Met Tyr Ala Thr Ile Tyr Glu Leu Lys Glu Asp Lys Ser Tyr
    50                  55                  60

Asn Val Thr Ser Val Gly Phe Asp Asp Lys Lys Cys Leu Tyr Lys Ile
65                  70                  75                  80
```

```
Arg Thr Phe Val Pro Gly Ser Gln Pro Gly Glu Phe Thr Leu Gly Arg
                85                  90                  95

Ile Lys Ser Glu Pro Gly Gly Thr Ser Trp Leu Val Arg Val Val Ser
            100                 105                 110

Thr Asn Tyr Asn Gln His Ala Met Val Phe Phe Lys Glu Val Ala Gln
            115                 120                 125

Asn Arg Glu Thr Phe Asn Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 44
<211> LENGTH: 178
<212> TYPE: PRT
<213> ORGANISM: Homo sapiens
<220> FEATURE:
<223> OTHER INFORMATION: wt Lcn2

<400> SEQUENCE: 44

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
        50                  55                  60

Asn Val Thr Ser Val Leu Phe Arg Lys Lys Lys Cys Asp Tyr Trp Ile
65                  70                  75                  80

Arg Thr Phe Val Pro Gly Ser Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
cccaggactc cacctcagac c                                            21
```

```
<210> SEQ ID NO 46
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
actgcgggtg ggaccaagcg ctgccgt                                       27

<210> SEQ ID NO 47
<211> LENGTH: 58
<212> TYPE: DNA
<213> ORGANISM: Artificial Sequence
<220> FEATURE:
<223> OTHER INFORMATION: Description of Artificial Sequence: Synthetic
      degenerate oligonucleotide DH-4

<400> SEQUENCE: 47
ggacaaccaa ttccatggga agtggtatgt ggtaggtgyt gcagggaatg tgttgctc     58

<210> SEQ ID NO 48
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer J08rev

<400> SEQUENCE: 48
gctgccgtcg atacactg                                                 18

<210> SEQ ID NO 49
<211> LENGTH: 534
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA sequence for the mature protein H1GA
      without Strep-tag II. Reading frame starts with the first
      nucleotide of the following sequence

<400> SEQUENCE: 49
caggactcca cctcagacct gatcccagcc ccacctctga gcaaggtccc tctgcagcag    60
aacttccagg acaaccaatt ccatgggaag tggtatgtgg taggtgctgc agggaatgtg   120
ttgctcagag aagacaaaga cccgcttaag atgtatgcca ccatctatga gctgaaagaa   180
gacaagagct acaatgtcac cagtgtcggg tttgatgata agaagtgttt gtacaagatc   240 cggactttg ttccaggttc ccagccaggc gagttcacgc tggcaggat taagagtgag    300 cctggaggta cgagttggct cgtccgagtg gtgagcacca actacaacca gcatgctatg   360
gtgttcttca aggaggttgc gcaaaacagg gagacgttca atatcaccct ctacgggaga   420
accaaggagc tgacttcgga actaaaggag aacttcatcc gcttctccaa atctctgggc   480
ctccctgaaa accacatcgt cttccctgtc ccaatcgacc agtgtatcga cggc         534

<210> SEQ ID NO 50
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
```

<220> FEATURE:
<223> OTHER INFORMATION: H1GA (Abeta)

<400> SEQUENCE: 50

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Ala Ala Gly Asn Val Leu Leu Arg Glu Asp Lys Asp Pro
        35                  40                  45

Leu Lys Met Tyr Ala Thr Ile Tyr Glu Leu Lys Glu Asp Lys Ser Tyr
    50                  55                  60

Asn Val Thr Ser Val Gly Phe Asp Asp Lys Lys Cys Leu Tyr Lys Ile
65                  70                  75                  80

Arg Thr Phe Val Pro Gly Ser Gln Pro Gly Glu Phe Thr Leu Gly Arg
                85                  90                  95

Ile Lys Ser Glu Pro Gly Gly Thr Ser Trp Leu Val Arg Val Val Ser
            100                 105                 110

Thr Asn Tyr Asn Gln His Ala Met Val Phe Phe Lys Glu Val Ala Gln
        115                 120                 125

Asn Arg Glu Thr Phe Asn Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 51
<211> LENGTH: 534
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DNA sequence for the mature protein H1GV
      without Strep-tag II. Reading frame starts with the first
      nucleotide of the following sequence

<400> SEQUENCE: 51
caggactcca cctcagacct gatcccagcc ccacctctga gcaaggtccc tctgcagcag      60
aacttccagg acaaccaatt ccatgggaag tggtatgtgg taggtgttgc agggaatgtg     120
ttgctcagag aagacaaaga cccgcttaag atgtatgcca ccatctatga gctgaaagaa     180
gacaagagct acaatgtcac cagtgtcggg tttgatgata agaagtgttt gtacaagatc     240 cggactttg ttccaggttc ccagccaggc gagttcacgc tgggcaggat taagagtgag     300
cctggaggta cgagttggct cgtccgagtg gtgagcacca actacaacca gcatgctatg     360
gtgttcttca aggaggttgc gcaaaacagg gagacgttca atatcaccct ctacgggaga     420
accaaggagc tgacttcgga actaaaggag aacttcatcc gcttctccaa atctctgggc     480
ctccctgaaa accacatcgt cttccctgtc ccaatcgacc agtgtatcga cggc           534

<210> SEQ ID NO 52
<211> LENGTH: 178
<212> TYPE: PRT
<213> ORGANISM: Artificial Sequence
<220> FEATURE:

<223> OTHER INFORMATION: Description of Artificial Sequence: Synthetic
      polypeptide
<220> FEATURE:
<223> OTHER INFORMATION: H1GV (A beta)

<400> SEQUENCE: 52

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Val Leu Leu Arg Glu Asp Lys Asp Pro
        35                  40                  45

Leu Lys Met Tyr Ala Thr Ile Tyr Glu Leu Lys Glu Asp Lys Ser Tyr
    50                  55                  60

Asn Val Thr Ser Val Gly Phe Asp Asp Lys Lys Cys Leu Tyr Lys Ile
65                  70                  75                  80

Arg Thr Phe Val Pro Gly Ser Gln Pro Gly Glu Phe Thr Leu Gly Arg
                85                  90                  95

Ile Lys Ser Glu Pro Gly Gly Thr Ser Trp Leu Val Arg Val Val Ser
            100                 105                 110

Thr Asn Tyr Asn Gln His Ala Met Val Phe Phe Lys Glu Val Ala Gln
        115                 120                 125

Asn Arg Glu Thr Phe Asn Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 53
<211> LENGTH: 5
<212> TYPE: PRT
<213> ORGANISM: Artificial Sequence
<220> FEATURE:
<223> OTHER INFORMATION: Description of Artificial Sequence: Synthetic
      5xHis tag

<400> SEQUENCE: 53

His His His His His
1               5

<210> SEQ ID NO 54
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 54

His His His His His His
1               5

<210> SEQ ID NO 55
<211> LENGTH: 6
<212> TYPE: PRT
<213> ORGANISM: Artificial Sequence
<220> FEATURE:
<223> OTHER INFORMATION: Description of Artificial Sequence: Synthetic
      consensus peptide
<220> FEATURE:

```
<221> NAME/KEY: MOD_RES
<222> LOCATION: (2)..(2)
<223> OTHER INFORMATION: Asp, Asn, Ser, Thr, or Trp
<220> FEATURE:
<221> NAME/KEY: MOD_RES
<222> LOCATION: (3)..(3)
<223> OTHER INFORMATION: Asn, Gln, His, Ile, Leu, or Lys
<220> FEATURE:
<221> NAME/KEY: MOD_RES
<222> LOCATION: (4)..(4)
<223> OTHER INFORMATION: Ala, Asp, Phe, Trp, or Tyr
<220> FEATURE:
<221> NAME/KEY: MOD_RES
<222> LOCATION: (5)..(5)
<223> OTHER INFORMATION: Asp, Gly, Leu, Phe, Ser, or Thr

<400> SEQUENCE: 55

Cys Xaa Xaa Xaa Xaa Cys
1               5

<210> SEQ ID NO 56
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(9)
<223> OTHER INFORMATION: a, c, t, g, unknown or other

<400> SEQUENCE: 56
ccannnnnnt gg                                                           12

<210> SEQ ID NO 57
<211> LENGTH: 7
<212> TYPE: PRT
<213> ORGANISM: Homo sapiens

<400> SEQUENCE: 57

Leu Val Phe Phe Ala Glu Asp
1               5

<210> SEQ ID NO 58
<211> LENGTH: 6
<212> TYPE: PRT
<213> ORGANISM: Homo sapiens

<400> SEQUENCE: 58

Val Phe Phe Ala Glu Asp
1               5

<210> SEQ ID NO 59
<211> LENGTH: 6
<212> TYPE: PRT
<213> ORGANISM: Homo sapiens

<400> SEQUENCE: 59

Phe Phe Ala Glu Asp Val
1               5

<210> SEQ ID NO 60
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: modified_base
<222> LOCATION: (20)..(21)
<223> OTHER INFORMATION: a, c, t or g
<220> FEATURE:
<221> NAME/KEY: modified_base
<222> LOCATION: (26)..(27)
<223> OTHER INFORMATION: a, c, t or g
<220> FEATURE:
<221> NAME/KEY: modified_base
<222> LOCATION: (32)..(33)
<223> OTHER INFORMATION: a, c, t or g
<220> FEATURE:
<221> NAME/KEY: modified_base
<222> LOCATION: (35)..(36)
<223> OTHER INFORMATION: a, c, t or g
<220> FEATURE:
<221> NAME/KEY: modified_base
<222> LOCATION: (47)..(48)
<223> OTHER INFORMATION: a, c, t or g
<220> FEATURE:
<221> NAME/KEY: modified_base
<222> LOCATION: (53)..(54)
<223> OTHER INFORMATION: a, c, t or g
<220> FEATURE:
<221> NAME/KEY: modified_base
<222> LOCATION: (59)..(60)
<223> OTHER INFORMATION: a, c, t or g

<400> SEQUENCE: 60
caagagctac aatgtcacan nkgtcnnktt tnnknnkaag aagtgtnnkt acnnkatcnn      60
kacttttgtt ccaggttcc                                                  79

<210> SEQ ID NO 61
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
ggtgacattg tagctcttat cttctttcag ctcatagatg gtggc                     45

<210> SEQ ID NO 62
<211> LENGTH: 567
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(564)

<400> SEQUENCE: 62 cag gac tcc acc tca gac ctg atc cca gcc cca cct ctg agc aag gtc       48
Gln Asp Ser Thr Ser Asp Leu Ile Pro Ala Pro Pro Leu Ser Lys Val
1               5                   10                  15 cct ctg cag cag aac ttc cag gac aac caa ttc cat ggg aag tgg tat       96
Pro Leu Gln Gln Asn Phe Gln Asp Asn Gln Phe His Gly Lys Trp Tyr
            20                  25                  30 gtg gta ggt ctc gca ggg aat gca att ctc aga gaa gac aaa gac ccg      144
Val Val Gly Leu Ala Gly Asn Ala Ile Leu Arg Glu Asp Lys Asp Pro
        35                  40                  45 caa aag atg tat gcc acc atc tat gag ctg aaa gaa gac aag agc tac      192
Gln Lys Met Tyr Ala Thr Ile Tyr Glu Leu Lys Glu Asp Lys Ser Tyr
    50                  55                  60 aat gtc acc tcc gtc ctg ttt agg aaa aag aag tgt gac tac tgg atc      240
```

```
Asn Val Thr Ser Val Leu Phe Arg Lys Lys Lys Cys Asp Tyr Trp Ile
 65                  70                  75                  80 agg act ttt gtt cca ggt tcc cag cca ggc gag ttc acg ctg ggc aac      288
Arg Thr Phe Val Pro Gly Ser Gln Pro Gly Glu Phe Thr Leu Gly Asn
                     85                  90                  95 att aag agt tac cct gga tta acg agt tac ctc gtc cga gtg gtg agc      336
Ile Lys Ser Tyr Pro Gly Leu Thr Ser Tyr Leu Val Arg Val Val Ser
                100                 105                 110 acc aac tac aac cag cat gct atg gtg ttc ttc aag aaa gtt tct caa      384
Thr Asn Tyr Asn Gln His Ala Met Val Phe Phe Lys Lys Val Ser Gln
            115                 120                 125 aac agg gag tac ttc aag atc acc ctc tac ggg aga acc aag gag ctg      432
Asn Arg Glu Tyr Phe Lys Ile Thr Leu Tyr Gly Arg Thr Lys Glu Leu
        130                 135                 140 act tcg gaa cta aag gag aac ttc atc cgc ttc tcc aaa tct ctg ggc      480
Thr Ser Glu Leu Lys Glu Asn Phe Ile Arg Phe Ser Lys Ser Leu Gly
145                 150                 155                 160 ctc cct gaa aac cac atc gtc ttc cct gtc cca atc gac cag tgt atc      528
Leu Pro Glu Asn His Ile Val Phe Pro Val Pro Ile Asp Gln Cys Ile
                165                 170                 175 gac ggc agc gct tgg tcc cac ccg cag ttc gaa aaa taa                  567
Asp Gly Ser Ala Trp Ser His Pro Gln Phe Glu Lys
                180                 185
```

<210> SEQ ID NO 63
<211> LENGTH: 188
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

```
Gln Asp Ser Thr Ser Asp Leu Ile Pro Ala Pro Pro Leu Ser Lys Val
  1               5                  10                  15

Pro Leu Gln Gln Asn Phe Gln Asp Asn Gln Phe His Gly Lys Trp Tyr
                 20                  25                  30

Val Val Gly Leu Ala Gly Asn Ala Ile Leu Arg Glu Asp Lys Asp Pro
             35                  40                  45

Gln Lys Met Tyr Ala Thr Ile Tyr Glu Leu Lys Glu Asp Lys Ser Tyr
 50                  55                  60

Asn Val Thr Ser Val Leu Phe Arg Lys Lys Lys Cys Asp Tyr Trp Ile
 65                  70                  75                  80

Arg Thr Phe Val Pro Gly Ser Gln Pro Gly Glu Phe Thr Leu Gly Asn
                 85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe Glu Lys
                180                 185
```

-continued

```
<210> SEQ ID NO 64
<211> LENGTH: 404
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (2)..(403)
<220> FEATURE:
<221> NAME/KEY: modified_base
<222> LOCATION: (32)..(34)
<223> OTHER INFORMATION: a, c, t or g; this region may not encompass a
      stop codon
<220> FEATURE:
<221> NAME/KEY: modified_base
<222> LOCATION: (44)..(49)
<223> OTHER INFORMATION: a, c, t or g; this region may not encompass a
      stop codon
<220> FEATURE:
<221> NAME/KEY: modified_base
<222> LOCATION: (71)..(73)
<223> OTHER INFORMATION: a, c, t or g; this region may not encompass a
      stop codon
<220> FEATURE:
<221> NAME/KEY: modified_base
<222> LOCATION: (80)..(82)
<223> OTHER INFORMATION: a, c, t or g; this region may not encompass a
      stop codon
<220> FEATURE:
<221> NAME/KEY: modified_base
<222> LOCATION: (128)..(130)
<223> OTHER INFORMATION: a, c, t or g; this region may not encompass a
      stop codon
<220> FEATURE:
<221> NAME/KEY: modified_base
<222> LOCATION: (134)..(136)
<223> OTHER INFORMATION: a, c, t or g; this region may not encompass a
      stop codon
<220> FEATURE:
<221> NAME/KEY: modified_base
<222> LOCATION: (140)..(145)
<223> OTHER INFORMATION: a, c, t or g; this region may not encompass a
      stop codon
<220> FEATURE:
<221> NAME/KEY: modified_base
<222> LOCATION: (155)..(157)
<223> OTHER INFORMATION: a, c, t or g; this region may not encompass a
      stop codon
<220> FEATURE:
<221> NAME/KEY: modified_base
<222> LOCATION: (161)..(163)
<223> OTHER INFORMATION: a, c, t or g; this region may not encompass a
      stop codon
<220> FEATURE:
<221> NAME/KEY: modified_base
<222> LOCATION: (167)..(169)
<223> OTHER INFORMATION: a, c, t or g; this region may not encompass a
      stop codon
<220> FEATURE:
<221> NAME/KEY: modified_base
<222> LOCATION: (212)..(214)
<223> OTHER INFORMATION: a, c, t or g; this region may not encompass a
      stop codon
<220> FEATURE:
<221> NAME/KEY: modified_base
<222> LOCATION: (224)..(226)
<223> OTHER INFORMATION: a, c, t or g; this region may not encompass a
      stop codon
<220> FEATURE:
<221> NAME/KEY: modified_base
<222> LOCATION: (233)..(235)
<223> OTHER INFORMATION: a, c, t or g; this region may not encompass a
      stop codon
<220> FEATURE:
<221> NAME/KEY: modified_base
<222> LOCATION: (242)..(244)
<223> OTHER INFORMATION: a, c, t or g; this region may not encompass a
```

```
stop codon
<220> FEATURE:
<221> NAME/KEY: modified_base
<222> LOCATION: (299)..(301)
<223> OTHER INFORMATION: a, c, t or g; this region may not encompass a
      stop codon
<220> FEATURE:
<221> NAME/KEY: modified_base
<222> LOCATION: (305)..(307)
<223> OTHER INFORMATION: a, c, t or g; this region may not encompass a
      stop codon
<220> FEATURE:
<221> NAME/KEY: modified_base
<222> LOCATION: (320)..(322)
<223> OTHER INFORMATION: a, c, t or g; this region may not encompass a
      stop codon
<220> FEATURE:
<221> NAME/KEY: modified_base
<222> LOCATION: (326)..(328)
<223> OTHER INFORMATION: a, c, t or g; this region may not encompass a
      stop codon

<400> SEQUENCE: 64 c caa ttc cat ggg aaa tgg tat gtc gtg ggc nnn gcc gga aat nnn nnn      49
  Gln Phe His Gly Lys Trp Tyr Val Val Gly Xaa Ala Gly Asn Xaa Xaa
  1               5                  10                  15 ctg cgt gag gat aag gat ccg nnn aaa atg nnn gcg acc att tac gag        97
Leu Arg Glu Asp Lys Asp Pro Xaa Lys Met Xaa Ala Thr Ile Tyr Glu
             20                  25                  30 ttg aaa gaa gat aaa tca tat aac gtc acc nnn gtg nnn ttt nnn nnn       145
Leu Lys Glu Asp Lys Ser Tyr Asn Val Thr Xaa Val Xaa Phe Xaa Xaa
         35                  40                  45 aag aaa tgc nnn tac nnn att nnn acc ttt gtg ccg ggg agc cag ccg       193
Lys Lys Cys Xaa Tyr Xaa Ile Xaa Thr Phe Val Pro Gly Ser Gln Pro
 50                  55                  60 ggc gag ttt act tta ggc nnn att aaa agt nnn ccg ggc nnn aca tca       241
Gly Glu Phe Thr Leu Gly Xaa Ile Lys Ser Xaa Pro Gly Xaa Thr Ser
 65                  70                  75                  80 nnn ttg gtc cgc gtc gtg agc acc aac tac aac cag cat gcc atg gtg       289
Xaa Leu Val Arg Val Val Ser Thr Asn Tyr Asn Gln His Ala Met Val
                 85                  90                  95 ttc ttc aag nnn gtg nnn cag aac cgc gag nnn ttt nnn atc aca ctg       337
Phe Phe Lys Xaa Val Xaa Gln Asn Arg Glu Xaa Phe Xaa Ile Thr Leu
            100                 105                 110 tac ggg cgc acg aaa gaa ctg aca agc gag ctg aag gaa aat ttt atc       385
Tyr Gly Arg Thr Lys Glu Leu Thr Ser Glu Leu Lys Glu Asn Phe Ile
        115                 120                 125 cgc ttt tcc aaa tct ctg g                                             404
Arg Phe Ser Lys Ser Leu
    130

<210> SEQ ID NO 65
<211> LENGTH: 404
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65
ccagagattt ggaaaagcgg ataaaatttt ccttcagctc gcttgtcagt tctttcgtgc      60
gcccgtacag tgtgatctta agtactcgc ggttctggga cactttcttg aagaacacca     120
tggcatgctg gttgtagttg gtgctcacga cgcggaccaa gtatgatgtc aggcccgggt    180 aactttttaat gttgcctaaa gtaaactcgc ccggctggct ccccggcaca aagtacgaa    240
```

```
tccagtagtc gcatttcttt ttgcgaaaca acacggaggt gacgttatat gatttatctt    300
ctttcaactc gtaaatggtc gcatacattt tctgcggatc cttatcctca cgcagaatgg    360
catttccggc caggcccacg acataccatt tcccatggaa ttgg                     404
```

```
<210> SEQ ID NO 66
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (15)..(16)
<223> OTHER INFORMATION: Any amino acid
<220> FEATURE:
<221> NAME/KEY: MOD_RES
<222> LOCATION: (24)..(24)
<223> OTHER INFORMATION: Any amino acid
<220> FEATURE:
<221> NAME/KEY: MOD_RES
<222> LOCATION: (27)..(27)
<223> OTHER INFORMATION: Any amino acid
<220> FEATURE:
<221> NAME/KEY: MOD_RES
<222> LOCATION: (43)..(43)
<223> OTHER INFORMATION: Any amino acid
<220> FEATURE:
<221> NAME/KEY: MOD_RES
<222> LOCATION: (45)..(45)
<223> OTHER INFORMATION: Any amino acid
<220> FEATURE:
<221> NAME/KEY: MOD_RES
<222> LOCATION: (47)..(48)
<223> OTHER INFORMATION: Any amino acid
<220> FEATURE:
<221> NAME/KEY: MOD_RES
<222> LOCATION: (52)..(52)
<223> OTHER INFORMATION: Any amino acid
<220> FEATURE:
<221> NAME/KEY: MOD_RES
<222> LOCATION: (54)..(54)
<223> OTHER INFORMATION: Any amino acid
<220> FEATURE:
<221> NAME/KEY: MOD_RES
<222> LOCATION: (56)..(56)
<223> OTHER INFORMATION: Any amino acid
<220> FEATURE:
<221> NAME/KEY: MOD_RES
<222> LOCATION: (71)..(71)
<223> OTHER INFORMATION: Any amino acid
<220> FEATURE:
<221> NAME/KEY: MOD_RES
<222> LOCATION: (75)..(75)
<223> OTHER INFORMATION: Any amino acid
<220> FEATURE:
<221> NAME/KEY: MOD_RES
<222> LOCATION: (78)..(78)
<223> OTHER INFORMATION: Any amino acid
<220> FEATURE:
<221> NAME/KEY: MOD_RES
<222> LOCATION: (81)..(81)
<223> OTHER INFORMATION: Any amino acid
<220> FEATURE:
<221> NAME/KEY: MOD_RES
<222> LOCATION: (100)..(100)
<223> OTHER INFORMATION: Any amino acid
<220> FEATURE:
<221> NAME/KEY: MOD_RES
<222> LOCATION: (102)..(102)
<223> OTHER INFORMATION: Any amino acid
<220> FEATURE:
```

<221> NAME/KEY: MOD_RES
<222> LOCATION: (107)..(107)
<223> OTHER INFORMATION: Any amino acid
<220> FEATURE:
<221> NAME/KEY: MOD_RES
<222> LOCATION: (109)..(109)
<223> OTHER INFORMATION: Any amino acid

<400> SEQUENCE: 66

```
Gln Phe His Gly Lys Trp Tyr Val Val Gly Xaa Ala Gly Asn Xaa Xaa
1               5                   10                  15

Leu Arg Glu Asp Lys Asp Pro Xaa Lys Met Xaa Ala Thr Ile Tyr Glu
            20                  25                  30

Leu Lys Glu Asp Lys Ser Tyr Asn Val Thr Xaa Val Xaa Phe Xaa Xaa
            35                  40                  45

Lys Lys Cys Xaa Tyr Xaa Ile Xaa Thr Phe Val Pro Gly Ser Gln Pro
    50                  55                  60

Gly Glu Phe Thr Leu Gly Xaa Ile Lys Ser Xaa Pro Gly Xaa Thr Ser
65                  70                  75                  80

Xaa Leu Val Arg Val Val Ser Thr Asn Tyr Asn Gln His Ala Met Val
                85                  90                  95

Phe Phe Lys Xaa Val Xaa Gln Asn Arg Glu Xaa Phe Xaa Ile Thr Leu
                100                 105                 110

Tyr Gly Arg Thr Lys Glu Leu Thr Ser Glu Leu Lys Glu Asn Phe Ile
            115                 120                 125

Arg Phe Ser Lys Ser Leu
            130
```

<210> SEQ ID NO 67
<211> LENGTH: 178
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (36)..(36)
<223> OTHER INFORMATION: Any amino acid
<220> FEATURE:
<221> NAME/KEY: MOD_RES
<222> LOCATION: (40)..(41)
<223> OTHER INFORMATION: Any amino acid
<220> FEATURE:
<221> NAME/KEY: MOD_RES
<222> LOCATION: (49)..(49)
<223> OTHER INFORMATION: Any amino acid
<220> FEATURE:
<221> NAME/KEY: MOD_RES
<222> LOCATION: (52)..(52)
<223> OTHER INFORMATION: Any amino acid
<220> FEATURE:
<221> NAME/KEY: MOD_RES
<222> LOCATION: (68)..(68)
<223> OTHER INFORMATION: Any amino acid
<220> FEATURE:
<221> NAME/KEY: MOD_RES
<222> LOCATION: (70)..(70)
<223> OTHER INFORMATION: Any amino acid
<220> FEATURE:
<221> NAME/KEY: MOD_RES
<222> LOCATION: (72)..(73)
<223> OTHER INFORMATION: Any amino acid
<220> FEATURE:
<221> NAME/KEY: MOD_RES
<222> LOCATION: (77)..(77)
<223> OTHER INFORMATION: Any amino acid
<220> FEATURE:
<221> NAME/KEY: MOD_RES

```
<222> LOCATION: (79)..(79)
<223> OTHER INFORMATION: Any amino acid
<220> FEATURE:
<221> NAME/KEY: MOD_RES
<222> LOCATION: (81)..(81)
<223> OTHER INFORMATION: Any amino acid
<220> FEATURE:
<221> NAME/KEY: MOD_RES
<222> LOCATION: (96)..(96)
<223> OTHER INFORMATION: Any amino acid
<220> FEATURE:
<221> NAME/KEY: MOD_RES
<222> LOCATION: (100)..(100)
<223> OTHER INFORMATION: Any amino acid
<220> FEATURE:
<221> NAME/KEY: MOD_RES
<222> LOCATION: (103)..(103)
<223> OTHER INFORMATION: Any amino acid
<220> FEATURE:
<221> NAME/KEY: MOD_RES
<222> LOCATION: (106)..(106)
<223> OTHER INFORMATION: Any amino acid
<220> FEATURE:
<221> NAME/KEY: MOD_RES
<222> LOCATION: (125)..(125)
<223> OTHER INFORMATION: Any amino acid
<220> FEATURE:
<221> NAME/KEY: MOD_RES
<222> LOCATION: (127)..(127)
<223> OTHER INFORMATION: Any amino acid
<220> FEATURE:
<221> NAME/KEY: MOD_RES
<222> LOCATION: (132)..(132)
<223> OTHER INFORMATION: Any amino acid
<220> FEATURE:
<221> NAME/KEY: MOD_RES
<222> LOCATION: (134)..(134)
<223> OTHER INFORMATION: Any amino acid

<400> SEQUENCE: 67

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Xaa Ala Gly Asn Xaa Xaa Leu Arg Glu Asp Lys Asp Pro
        35                  40                  45

Xaa Lys Met Xaa Ala Thr Ile Tyr Glu Leu Lys Glu Asp Lys Ser Tyr
    50                  55                  60

Asn Val Thr Xaa Val Xaa Phe Xaa Xaa Lys Lys Cys Xaa Tyr Xaa Ile
65                  70                  75                  80

Xaa Thr Phe Val Pro Gly Ser Gln Pro Gly Glu Phe Thr Leu Gly Xaa
                85                  90                  95

Ile Lys Ser Xaa Pro Gly Xaa Thr Ser Xaa Leu Val Arg Val Val Ser
            100                 105                 110

Thr Asn Tyr Asn Gln His Ala Met Val Phe Phe Lys Xaa Val Xaa Gln
        115                 120                 125

Asn Arg Glu Xaa Phe Xaa Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```